(12) United States Patent
Anryu et al.

(10) Patent No.: US 10,359,700 B2
(45) Date of Patent: Jul. 23, 2019

(54) SALT, ACID GENERATOR, PHOTORESIST COMPOSITION AND PROCESS OF PRODUCING PHOTORESIST PATTERN

(71) Applicant: SUMITOMO CHEMICAL COMPANY, LIMITED, Tokyo (JP)

(72) Inventors: Yukako Anryu, Osaka (JP); Satoshi Yamamoto, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/714,812

(22) Filed: May 18, 2015

(65) Prior Publication Data
US 2015/0338735 A1 Nov. 26, 2015

(30) Foreign Application Priority Data

May 20, 2014 (JP) .................................. 2014-104038

(51) Int. Cl.
| | |
|---|---|
| *G03F 7/039* | (2006.01) |
| *G03F 7/004* | (2006.01) |
| *G03F 7/20* | (2006.01) |
| *G03F 7/32* | (2006.01) |
| *G03F 7/38* | (2006.01) |
| *C07C 309/17* | (2006.01) |
| *C07D 411/06* | (2006.01) |
| *C07D 295/26* | (2006.01) |
| *C07D 339/08* | (2006.01) |
| *C07D 321/00* | (2006.01) |
| *C07D 417/06* | (2006.01) |
| *C07D 307/33* | (2006.01) |
| *C07D 321/10* | (2006.01) |
| *C07D 319/08* | (2006.01) |
| *C07D 327/06* | (2006.01) |

(52) U.S. Cl.
CPC .......... *G03F 7/0397* (2013.01); *C07C 309/17* (2013.01); *C07D 295/26* (2013.01); *C07D 307/33* (2013.01); *C07D 319/08* (2013.01); *C07D 321/00* (2013.01); *C07D 321/10* (2013.01); *C07D 327/06* (2013.01); *C07D 339/08* (2013.01); *C07D 411/06* (2013.01); *C07D 417/06* (2013.01); *G03F 7/0045* (2013.01); *G03F 7/0046* (2013.01); *G03F 7/2041* (2013.01); *G03F 7/322* (2013.01); *G03F 7/325* (2013.01); *G03F 7/38* (2013.01); *C07C 2601/14* (2017.05); *C07C 2603/74* (2017.05)

(58) Field of Classification Search
None
See application file for complete search history.

(56) References Cited

U.S. PATENT DOCUMENTS

| 8,367,298 B2 | 2/2013 | Ichikawa et al. |
| 8,431,326 B2 | 4/2013 | Ichikawa et al. |
| 8,652,754 B2 | 2/2014 | Ichikawa et al. |

(Continued)

FOREIGN PATENT DOCUMENTS

| JP | 2006-257078 | * | 9/2006 |
| JP | 2011-37837 A | | 2/2011 |

(Continued)

OTHER PUBLICATIONS

Japanese Office Action for Japanese Application No. 2015-101607, dated Nov. 20, 2018, with English translation.

*Primary Examiner* — Sin J Lee
(74) *Attorney, Agent, or Firm* — Birch, Stewart, Kolasch & Birch, LLP

(57) ABSTRACT

A salt represented by formula (I):

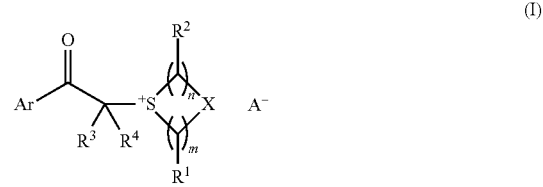

in which X represents an oxygen atom, a sulfur atom or —N(SO$_2$R$^5$)—;

R$^5$ represents a C1-C12 alkyl group which can have a fluorine atom and in which a methylene group can be replaced by an oxygen atom or a carbonyl group, a C3-C12 cycloalkyl group which can have a fluorine atom, or a C6-C12 aromatic hydrocarbon group which can have a fluorine atom;

Ar represents a C6-C36 aromatic hydrocarbon group which can have a substituent or a C4-C36 heteroaromatic hydrocarbon group which can have a substituent;

R$^1$ and R$^2$ each independently represent a hydrogen atom, a hydroxy group, or a C1-C12 hydrocarbon group in which a methylene group can be replaced by an oxygen atom or a carbonyl group;

"m" and "n" each independently represent 1 or 2;

R$^3$ and R$^4$ each independently represent a hydrogen atom or a C1-C12 hydrocarbon group, R$^3$ and R$^4$ may be bonded to form a ring, or R$^3$ or R$^4$ may form a ring together with Ar; and A$^-$ represents an organic anion which has an acid-labile group, an organic anion which has a base-labile group, or an organic anion which has an acid-labile group and a base-labile group.

4 Claims, No Drawings

(56) References Cited

U.S. PATENT DOCUMENTS

| | | | |
|---|---|---|---|
| 8,709,699 B2 | 4/2014 | Ichikawa et al. | |
| 2003/0224290 A1 | 12/2003 | Kobayashi et al. | |
| 2011/0014568 A1* | 1/2011 | Ichikawa | C07C 25/18 430/270.1 |
| 2012/0088190 A1* | 4/2012 | Ichikawa | C07D 321/10 430/281.1 |
| 2014/0186767 A1* | 7/2014 | Thackeray | G03F 7/0045 430/281.1 |
| 2014/0248562 A1 | 9/2014 | Shibuya et al. | |

FOREIGN PATENT DOCUMENTS

| | | |
|---|---|---|
| JP | 2012-97074 A | 5/2012 |
| JP | 2012-226331 A | 11/2012 |
| JP | 2013-41245 A | 2/2013 |
| JP | 2013-41246 A | 2/2013 |
| JP | 2013-235250 A | 11/2013 |
| JP | 2013-235253 A | 11/2013 |
| JP | 2013-257536 A | 12/2013 |
| WO | WO 2013/0697753 A1 * | 5/2013 |

* cited by examiner

SALT, ACID GENERATOR, PHOTORESIST COMPOSITION AND PROCESS OF PRODUCING PHOTORESIST PATTERN

This nonprovisional application claims priority under 35 U.S.C. § 119(a) on Patent Application No. 2014-104038 filed in JAPAN on May 20, 2014, the entire contents of which are hereby incorporated by reference.

TECHNICAL FIELD

The present disclosure relates to a salt, an acid generator, a photoresist composition and a process of producing photoresist pattern.

BACKGROUND ART

At to semiconductor microfabrication, US2003/224290 (A1) mentions a salt for an acid generator, represented as follow.

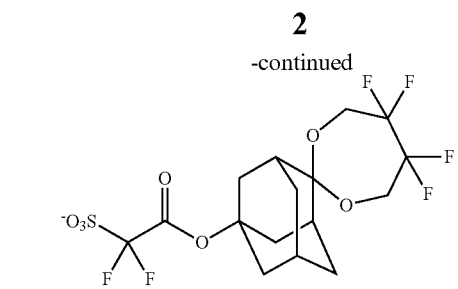

US2014/248562A1 mentions a salt for an acid generator, represented as follow.

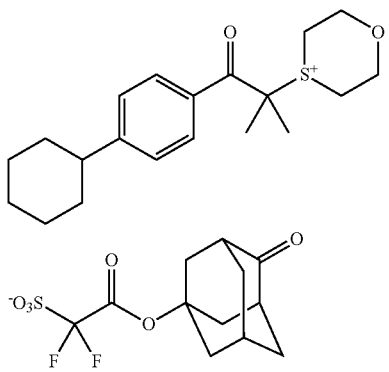

US2012/088190 (A1) mentions a salt for an acid generator, represented as follow.

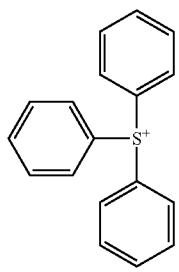

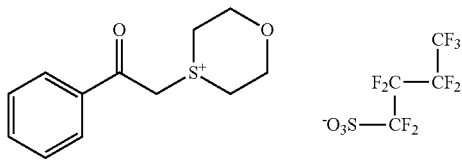

SUMMARY OF THE DISCLOSURE

The present invention relates to the followings:

[1] A salt represented by formula (I):

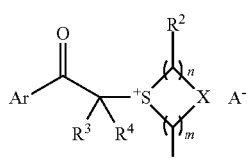

in which X represents an oxygen atom, a sulfur atom or $-N(SO_2R^5)-$;

$R^5$ represents a C1-C12 alkyl group which can have a fluorine atom and in which a methylene group can be replaced by an oxygen atom or a carbonyl group, a C3-C12 cycloalkyl group which can have a fluorine atom, or a C6-C12 aromatic hydrocarbon group which can have a fluorine atom;

Ar represents a C6-C36 aromatic hydrocarbon group which can have a substituent or a C4-C36 heteroaromatic hydrocarbon group which can have a substituent;

$R^1$ and $R^2$ each independently represent a hydrogen atom, a hydroxy group, or a C1-C12 hydrocarbon group in which a methylene group can be replaced by an oxygen atom or a carbonyl group;

"m" and "n" each independently represent 1 or 2;

$R^3$ and $R^4$ each independently represent a hydrogen atom or a C1-C12 hydrocarbon group, $R^3$ and $R^4$ may be bonded to form a ring, or $R^3$ or $R^4$ may form a ring together with Ar; and $A^-$ represents an organic anion which has an acid-labile group, an organic anion which has a base-labile group, or an organic anion which has an acid-labile group and a base-labile group.

[2] An acid generator which comprises the salt according to [1].

[3] A photoresist composition comprising:
the acid generator according to [2] and a resin having an acid-labile group.

[4] A process for producing a photoresist pattern comprising the following steps (1) to (5):

(1) a step of applying the photoresist composition according [3] on a substrate.

(2) a step of forming a composition film by conducting drying, (3) a step of exposing the composition film to radiation, (4) a step of baking the exposed composition film, and (5) a step of developing the baked composition film.

DESCRIPTION OF PREFERRED EMBODIMENTS

<Salt of Formula (I)>
The salt of the disclosure is represented by formula (I):

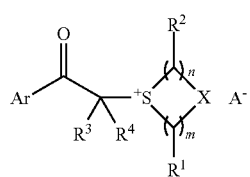

(I)

In the formula, X represents an oxygen atom, a sulfur atom or —N(SO$_2$R$^5$)—.

R$^5$ represents a C1-C12 alkyl group which can have a fluorine atom and in which a methylene group can be replaced by an oxygen atom or a carbonyl group, a C3-C12 cycloalkyl group which can have a fluorine atom, or a C6-C12 aromatic hydrocarbon group which can have a fluorine atom.

For R$^5$, examples of the alkyl group include a methyl group, an ethyl group, an n-propyl group, an isopropyl group, an n-butyl group, an isobutyl group, a tert-butyl group, a pentyl group, a hexyl group, an octyl group, a nonyl group, a decyl group, an undecyl group and a dodecyl group.

Examples of the cycloalkyl group include a cyclopentyl group, a cyclohexyl group, a cycloheptyl group, a cyclooctyl group, a cyclononyl group and a cyclododecyl group.

Examples of the aromatic hydrocarbon group include a phenyl group and a naphthyl group.

Ar represents a C6-C36 aromatic hydrocarbon group which can have a substituent or a C4-C36, preferably C6-C36, heteroaromatic hydrocarbon group which can have a substituent.

For Ar, the aromatic hydrocarbon group has preferably 6 to 24, more preferably 6 to 18, carbon atoms, and the heteroaromatic hydrocarbon group has preferably 4 to 24, more preferably 4 to 18, carbon atoms.

For Ar, examples of the aromatic hydrocarbon group include a phenyl group, a naphthyl group, an anthracenyl group, a phenanthryl group, a tolyl group, a xylyl group, a dimethylphenyl group, a trimethylphenyl group, an ethylphenyl group, a propylphenyl group, a butylphenyl group, a biphenyl group, a triphenyl group, an indenyl group, and a tetrahydronaphthyl group.

Examples of the heteroatom for the heteroaromatic hydrocarbon group include a nitrogen atom, an oxygen atom and a sulfur atom.

Examples of the heteroaromatic hydrocarbon group include a furyl group and a thienyl group.

Examples of the substituent for the aromatic hydrocarbon group and the heteroaromatic hydrocarbon group include a hydroxy group, a C1-C12 alkoxy group in which a methylene group can be replaced by an oxygen atom, a C2-C18 alkylcarbonyloxy group, a C7-C18 arylcarbonyloxy group, and a C2-C18 alkoxycarbonyloxy group.

The substituent is preferably a hydroxy group.

Examples of the alkoxy groups include a methoxy group, an ethoxy group, a propoxy group, a butoxy group, a pentyloxy group, a hexyloxy group, a heptyloxy group, an octyloxy group, a decyloxy group and a dodecyloxy group, preferably a C1-C6 alkoxy group, and more preferably a methoxy group.

Examples of the alkylcarbonyl oxy group include a methylcarbonyloxy group, an ethylcarbonyloxy group, an n-propylcarbonyloxy group, an isopropylcarbonyloxy group, an n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group, preferably a C2-C12 alkylcarbonyloxy group, more preferably a methylcarbonyloxy group.

Examples of the arylcarbonyloxy group include a phenylcarbonyloxy group and a tosyl carbonyloxy group, preferably a C7-C12 arylcarbonyloxy group, and more preferably a phenylcarbonyloxy group.

Examples of the alkoxycarbonyloxy group include a methoxycarbonyloxy group, an ethoxycarbonyloxy group, an n-propoxycarbonyloxy group, an isopropoxycarbonyloxy group, an n-butoxycarbonyloxy group, a sec-butoxycarbonyloxy group, a tert-butoxycarbonyloxy group, a pentyloxycarbonyloxy group, a hexyloxycarbonyloxy group, an octyloxycarbonyloxy group and a 2-ethyl hexyloxycarbonyloxy group, preferably one in which the alkyl moiety has 2 to 8 carbon atoms, more preferably a tert-butyloxycarbonyloxy group.

R$^1$ and R$^2$ each independently represent a hydrogen atom, a hydroxy group, or a C1-C12 hydrocarbon group in which a methylene group can be replaced by an oxygen atom or a carbonyl group;

For R$^1$ and R$^2$, examples of the hydrocarbon group include an alkyl group, an alicyclic hydrocarbon group, an aromatic hydrocarbon group and any combination of them.

Examples of the alkyl group include a methyl group, an ethyl group, an n-propyl group, an isopropyl group, an n-butyl group, an isobutyl group, a tert-butyl group, a pentyl group, a hexyl group, an octyl group, a nonyl group, a decyl group, an undecyl group and a dodecyl group.

The alicyclic hydrocarbon group may be monocyclic or polycyclic one. Examples of the monocyclic alicyclic hydrocarbon group include a C3-C12 cycloalkyl group such as a cyclopropyl group, a cyclobutyl group, a cyclopentyl group, a cyclohexyl group, a cycloheptyl group, a cyclooctyl group, a cyclononyl group and a cyclododecyl group.

Examples of the polycyclic alicyclic hydrocarbon group include a decahydronaphthyl group, an adamantyl group, a 2-alkyladamantane-2-yl group, 1-(adamantane-1-yl)alkane-1-yl group, a norbornyl group, a methylnorbornyl group and an isobornyl group.

Examples of the aromatic hydrocarbon group include a phenyl group and a naphthyl group.

Examples of any combination as mentioned above include an aralkyl group such as a benzyl group and a phenethyl group.

Examples of the hydrocarbon group in which a methylene group has been replaced by an oxygen atom or a carbonyl group include a methoxy group, an ethoxy group, a butoxy group, an acetyl group, a methoxycarbonyl group, an acetyloxy group, a butoxycarbonyloxy group and a benzoyloxy group.

R$^3$ and R$^4$ each independently represent a hydrogen atom or a C1-C12 hydrocarbon group in which a methylene group can be replaced by an oxygen atom or a carbonyl group, R$^3$ and R$^4$ may be bonded to form a ring, or R$^3$ or R$^4$ may form a ring together with Ar.

For R$^3$ and R$^4$, examples of the hydrocarbon group include the same as those referring to R$^1$ and R$^2$.

Examples of the ring corresponding to the combination of R$^3$ and R$^4$ include a C3-C12 cycloalkyl group such as a cyclopropyl group, a cyclobutyl group, a cyclopentyl group or a cyclohexyl group, preferably a C3-C8 cycloalkyl group, and more preferably a cyclopentyl group and a cyclohexyl group.

The ring formed by bonding $R^3$ or $R^4$ together with Ar has a structure *¹-Ar—CO—C—*² where *1 and *2 represent a binding site to a carbon atom at each end of $R^3$ or $R^4$ respectively.

In formula (I), "m" and "n" each independently represent 1 or 2. The "m" represents preferably 2. The "n" represents preferably 2. Preferably, at least one of "m" and "n" represents 2, and more preferably both of "m" and "n" represent 2.

$R^1$ represents preferably a hydrogen atom.

$R^2$ represents preferably a hydrogen atom.

$R^1$ and $R^2$ represent preferably the same group as each other, more preferably a hydrogen atom.

$R^3$ represents preferably a hydrogen atom or a C1-C6 alkyl group.

$R^4$ represents preferably a hydrogen atom or a C1-C6 alkyl group.

Preferably at least one of $R^3$ and $R^4$ represents a hydrogen atom, and more preferably both of $R^3$ and $R^4$ represents a hydrogen atom.

Ar represents preferably a C6-C36 aromatic hydrocarbon group which can have a substituent, more preferably a C6-C18 aromatic hydrocarbon group which can have a substituent, and still more preferably a phenyl group which can have a substituent and a naphthyl group which can have a substituent. Examples of the substituent for the phenyl group and naphthyl group include a C1-C4 alkyl group, a hydroxy group, a C1-C6 alkoxy group, a C2-C4 alkylcarbonyloxy group, preferably a hydroxy group.

X represents preferably an oxygen atom.

Examples of the cation for formula (I) include the following ones, preferably those represented by formula (I-c-1), formula (I-c-2), formula (I-c-3), formula (I-c-4), formula (I-c-5), formula (I-c-6), formula (I-c-7) and formula (I-c-8).

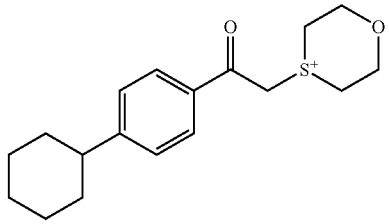

(I-c-4)

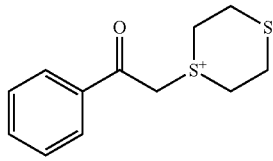

(I-c-5)

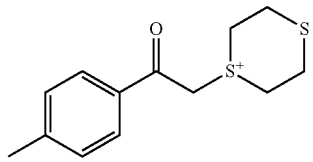

(I-c-6)

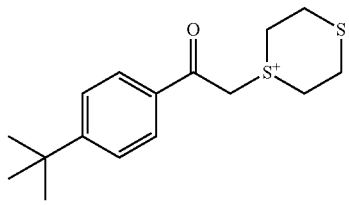

(I-c-7)

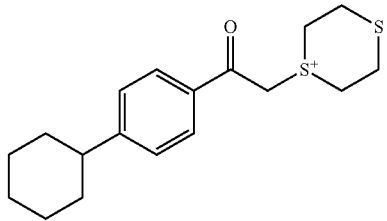

(I-c-8)

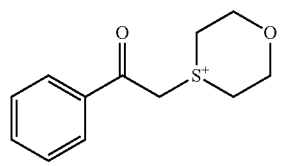

(I-c-1)

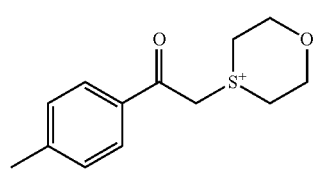

(I-c-2)

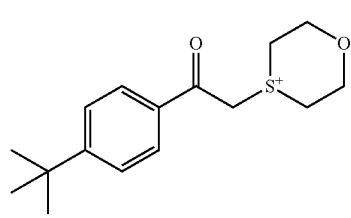

(I-c-3)

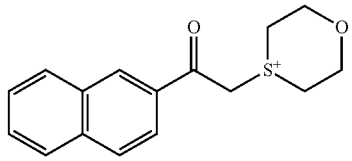

(I-c-9)

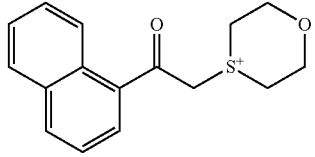

(I-c-10)

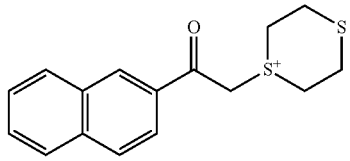

(I-c-11)

(I-c-12)
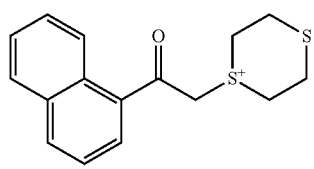
(I-c-13)
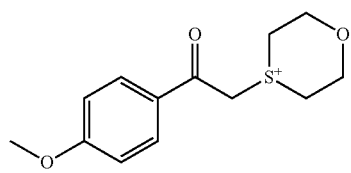
(I-c-14)
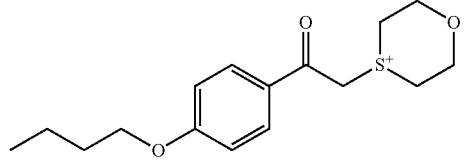
(I-c-15)
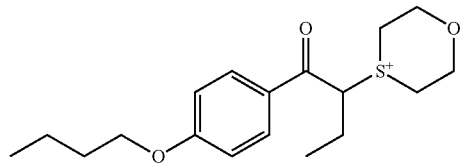
(I-c-16)
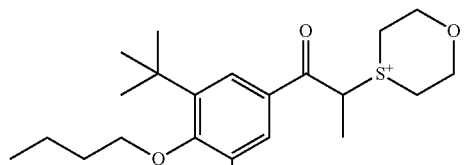
(I-c-17)
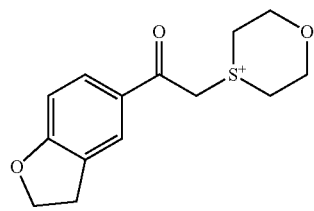
(I-c-18)
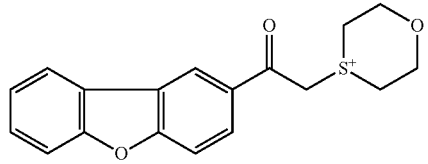
(I-c-19)
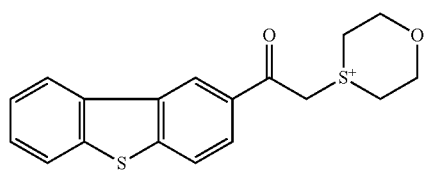
(I-c-20)
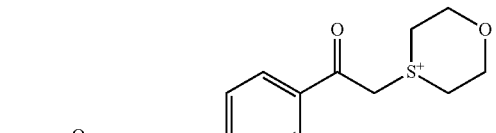
(I-c-21)
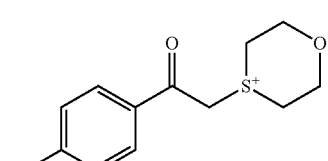
(I-c-22)
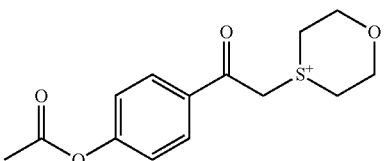
(I-c-23)
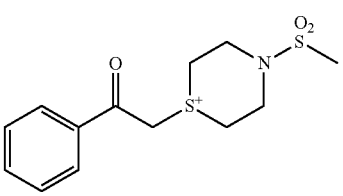
(I-c-24)
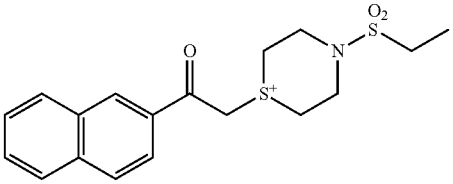
(I-c-25)
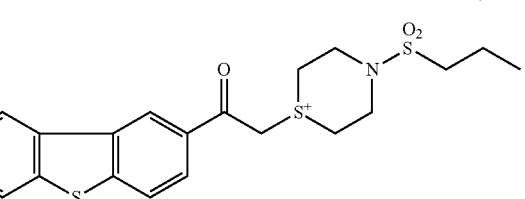
(I-c-26)
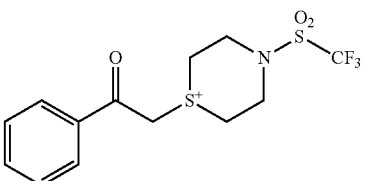
(I-c-27)
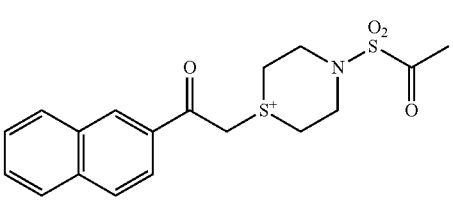

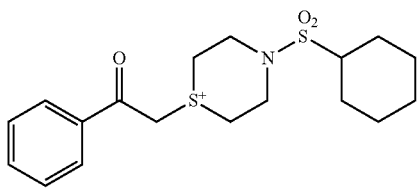

(I-c-28)

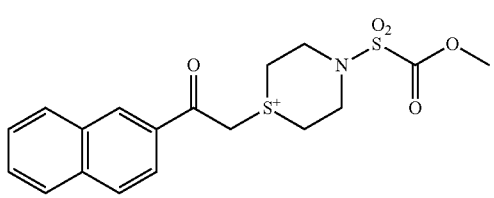

(I-c-29)

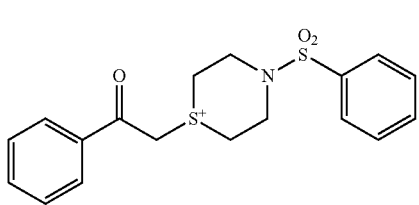

(I-c-30)

A⁻ represents an organic anion which has an acid-labile group, an organic anion which has a base-labile group, or an organic anion which has an acid-labile group and a base-labile group.

Here, the "acid-labile group" means a group which has a leaving group being removed therefrom by the action of an acid to have a hydrophilic group, such as a hydroxy group or a carboxy group. The acid for the action includes one generated from an acid generator or the salt of formula (I).

The "base-labile group" means a group which has a leaving group being removed therefrom by the action of base, such as tetramethylammonium hydroxide, to have a hydrophilic group, such as a hydroxy group or a carboxy group.

For A⁻, the organic anion may be a sulfonic acid anion, a sulfonylimide anion, a sulfonylmethide anion or a carboxylic acid anion, which has an acid-labile group, a base-labile group or both of them.

The organic anion preferably comprises a sulfo group [$SO_3^-$].

The organic anion represented by A⁻ can have two or more acid-labile groups, two or more base-labile groups, or both of an acid-labile group and a base-labile group.

The salt represented by formula (I) where A⁻ is an organic anion which has an acid-labile group is useful for a negative-type photoresist composition. The salt represented by formula (I) where A⁻ is an organic anion which has a base-labile group is useful for a positive-type photoresist composition.

Examples of the acid-labile group include a group having an acetal structure, a tertiary alcohol group which can have a substituent, and a tertiary alkoxycarbonyloxy group which can have a substituent. The "tertiary alcohol group" means an alcohol group where an oxygen atom is attached to a tertiary carbon atom.

The "tertiary alkoxycarbonyloxy group" means a group formed by binding the tertiary alcohol group to a carbonyloxy group.

For A⁻, the acid-labile group is preferably one having an acetal structure.

Preferably, the organic anion which has an acid-labile group comprises a ring structure and the ring structure comprises an acid-labile group which has an acetal structure. Here, the acetal structure includes those in which two oxygen atoms are bonded to one carbon atom, those in which one oxygen atom and one sulfur atom are bonded to one carbon atom, and those in which two sulfur atoms are bonded to one carbon atom More preferably, the organic anion which has an acid-labile group has a group represented by formula (a).

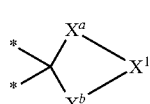

(a)

In the formula, $X^a$ and $X^b$ each independently represent an oxygen atom or a sulfur group;

$X^1$ represents a Divalent C1-C12 saturated hydrocarbon group which can have a fluorine atom; and

* represents a binding site.

$X^a$ and $X^b$ are preferably the same atom each other, more preferably an oxygen atom.

For $X^1$, the divalent saturated hydrocarbon group includes alkanediyl groups, divalent alicyclic hydrocarbon groups, and combination of them.

Specific examples of the saturated hydrocarbon group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, and an octane-1,8-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methylpropane-1,2-diyl group, a pentane-1,4-diyl group, and a 2-methylbutane-1,4-diyl group;

divalent monocyclic alicyclic saturated hydrocarbon group including C3-C12 cycloalkanediyl groups such as a cyclobutane-1,3-diyl group, a cyclopentane-1,3-diyl group, a cyclohexane-1,4-diyl group, and a cyclooctane-1,5-diyl group; and divalent polycyclic saturated hydrocarbon groups such as a norbornane-1,4-diyl group, a norbornane-2,5-diyl group, an adamantane-1,5-diyl group, and an adamantane-2,6-diyl group.

The divalent saturated hydrocarbon group for X' is preferably a C1-C12 alkanediyl group, more preferably a C1-C6 alkanediyl group.

$X^1$ has preferably a fluorine atom. The amount of fluorine in the salt of the disclosure is preferably 5% or more, more preferably 7% or more, while it is preferably 40% or less, more preferably 30% or less.

Here, the "amount of fluorine" is calculated by the following formula.

[The amount of fluorine]=100×[(The atomic weight of fluorine)×(The number of fluorine atom)]/ (The molecular weight of the salt)

$X^1$ is preferably a group represented by formula ($X^1$-1).

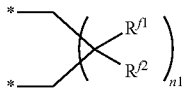
(X$^1$-1)

In the formula ($X^1$-1), $R^{f1}$ and $R^{f2}$ each independently represent a fluorine atom or a C1-C6 fluoroalkyl group, "n1" represents an integer of 1 to 10, and

* represents a binding site to $X^a$ and $X^b$.

For $R^{f1}$ and $R^{f2}$, examples of the fluoroalkyl group include a trifluoromethyl group, difluoromethyl group, a perfluoroethyl group, 1,1-difluoroethyl group, 1,1,1-trifluoroethyl group, 1,1,2,2-tetrafluoroethyl group, 2,2,3,3,3-pentafluoropropyl group, 1-(trifluoromethyl)-1,1,2,2-tetrafluoroethyl group, perfluoropropyl group, 1,1,1,2,2-pentafluoropropyl group, 1,1,1,2,2,3,3-hexafluoropropyl group, perfluorobutyl group, 1,1,2,2,3,3,4,4-octafluorobutyl group, 1,1-bis(trifluoromethyl)-2,2,2-trifluoroethyl group, 2-(perfluoropropyl)ethyl group, 1,1,1,2,2,3,3,4,4,5,5-decafluoropentyl group, perfluoropentyl group, 1,1,1,2,2,3,3,4,4-nonafluoropentyl group, 1,1,1,2,2,3,3,4,4,5,5-decafluorohexyl group, 1,1,1,2,2,3,3,4,4,5,5,6,6-dodecafluorohexyl group, perfluoro(pentylmethyl) group and a n-perfluorohexyl group, preferably a C1-C4 perfluoroalkyl group such as trifluoromethyl group, a perfluoroethyl group, perfluoropropyl group, perfluorobutyl group.

$R^{f1}$ and $R^{f2}$ are preferably identical to each other, more preferably a fluorine atom.

In formula ($X^2$-1), "n1" represents an integer of preferably 1 to 8, more preferably 1 to 6, still more preferably 1 to 4, further more preferably 1 and 2.

The divalent group of formula ($X^1$-1) is preferably one represented by formula ($X^1$-2), and more preferably one represented by formula ($X^1$-3) or formula ($X^1$-4).

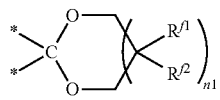
(X$^1$-2)

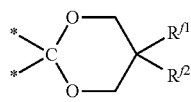
(X$^1$-3)

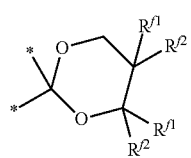
(X$^1$-4)

In formula ($X^1$-2), "n1" is as defined above. In formulae ($X^1$-2), ($X^1$-3) and ($X^1$-4), $R^{f1}$, $R^{f2}$ and * are as defined above.

The organic anion which has an acid-labile group preferably comprises a group represented by formula (a-1).

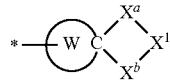
(a-1)

In formula (a-1), $X^a$, $X^b$, $X^1$ and * are as defined above; and the ring W represents a C3-C36 alicyclic hydrocarbon group in which a methyelene group can be replaced by an oxygen atom, a sulfur atom, a carbonyl group or a sulfonyl group and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of them.

Examples of the ring W include the rings represented by any one of formulae (a1-1-1) to (a1-1-11), those in which a methylene group has been replaced by an oxygen atom, a sulfur atom, a carbonyl group, a sulfonyl group and in which a hydrogen atom can be replaced by a hydroxy group, a c1-C12 alkyl group, a C1-C12 alkoxy group, a C3-C12 alicyclic hydrocarbon group, a C6-C10 aromatic hydrocarbon group or a combination of any two or more of them.

(a-1-1)

(a-1-2)

(a-1-3)

(a-1-4)

(a-1-5)

(a-1-6)

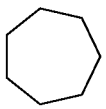
(a-1-7)

(a-1-8)

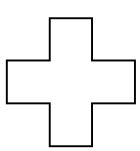
(a-1-9)

-continued

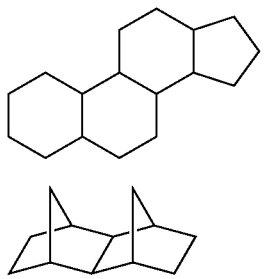

(a-1-10)

(a-1-11)

As to a group which the alicyclic hydrocarbon group of the ring W can have, the alkyl group may be a linear or branched one, examples of which include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a nonyl group, an undecyl group and a decyl group. Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. The alicyclic hydrocarbon group may be a monocyclic or polycyclic one, examples of which include the following ones.

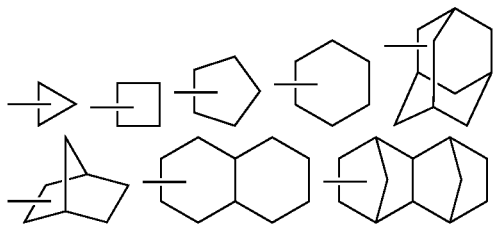

Examples of the aromatic hydrocarbon group include a phenyl group and a naphthyl group.

The ring W is preferably a C6-C18 alicyclic hydrocarbon group in which a methylene group can be replaced by an oxygen atom, a sulfur atom, a carbonyl group or a sulfonyl group and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them, and more preferably one represented by formula (a1-1-1), (a1-1-2) or (a1-1-3) and the one represented by formula (a1-1-1), (a1-1-2) or (a1-1-3) in which a methylene group has been replaced by an oxygen atom, a sulfur atom, a carbonyl group or a sulfonyl group, and in which a hydrogen atom has been replaced by a hydroxy group, a c1-C12 alkyl group, a C1-C12 alkoxy group, or a C3-C12 alicyclic hydrocarbon group.

The organic anion which has an acid-labile group is preferably an organic sulfonic acid anion, more preferably one represented by formula (a2).

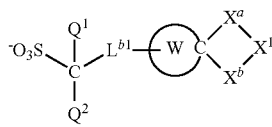

(a2)

In formula (a2), $X^a$, $X^b$, $X^1$ and the ring W are as defined above; $L^{b1}$ represents a C1-C24 divalent saturated hydrocarbon group where a methylene group can be replaced by an oxygen atom or a carbonyl group and where a hydrogen atom can be replaced by a fluorine atom or a hydroxy group; and $Q^1$ and $Q^2$ each independently represent a fluorine atom or a C1-C6 perfluoroalkyl group.

In formula (a2), $Q^1$ and $Q^2$ independently each represent a fluorine atom or a C1-C6 perfluoroalkyl group.

Examples of the C1-C6 perfluoroalkyl group represented by $Q^1$ and $Q^2$ include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

$Q^1$ and $Q^2$ independently each represent preferably a fluorine atom or a trifluoromethyl group, more preferably a fluorine atom.

$L^{b1}$ represents a C1-C24 divalent saturated hydrocarbon group where a methylene group can be replaced by an oxygen atom or a carbonyl group and where a hydrogen atom can be replaced by a fluorine atom or a hydroxy group.

Examples of the divalent saturated hydrocarbon group include a linear alkanediyl groups, branched alkanediyl groups, monocyclic or polycyclic alicyclic saturated hydrocarbon groups, and a group formed by combining two or more of them.

Specific examples of the divalent saturated hydrocarbon group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl groups; branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group; divalent monocyclic alicyclic saturated hydrocarbon group including cycloalkanediyl groups such as a cyclobutane-1,3-diyl group, a cyclopentane-1,3-diyl group, a cyclohexane-1,4-diyl group, and a cyclooctane-1,5-diyl group; and divalent polycyclic saturated hydrocarbon groups such as a norbornane-1,4-diyl group, a norbornane-2,5-diyl group, an adamantane-1,5-diyl group, an adamantane-2,6-diyl group.

Specific examples of the divalent saturated hydrocarbon group where a methylene group has been replaced by an oxygen atom or a carbonyl group include those represented by formulae (b1-1), (b1-2) and (b1-3).

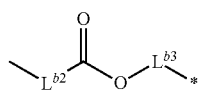

(b1-1)

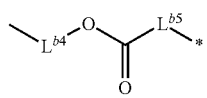

(b1-2)

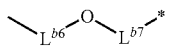  (b1-3)

In these formulae, * represents a binding site to the ring W.

In formula (b1-1), $L^{b2}$ represents a single bond or a C1-C22 divalent saturated hydrocarbon group where a hydrogen atom can be replaced by a fluorine atom;

$L^{b3}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b2}$ and $L^{b3}$ are 22 or less.

In formula (b1-2), $L^{b4}$ represents a single bond or a C1-C22 divalent saturated hydrocarbon group where a hydrogen atom can be replaced by a fluorine atom;

$L^{b5}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b4}$ and $L^{b5}$ are 22 or less.

In formula (b1-3), $L^{b6}$ represents a single bond or a C1-C23 divalent saturated hydrocarbon group where a hydrogen atom can be replaced by a fluorine atom or a hydroxy group;

$L^{b7}$ represents a single bond or a C1-C23 divalent saturated hydrocarbon group where a hydrogen atom may be replaced by a fluorine atom or a hydroxy group, and where a methylene group can be replaced by —O— or —CO—; provided that total carbon atoms in $L^{b6}$ and $L^{b7}$ are 23 or less and —CO— is not bonded to the oxygen atom between $L^{b6}$ and $L^{b7}$.

In formulae (b1-1) to (b1-3), the number of the carbon atoms in the divalent saturated hydrocarbon groups include that of the carbon atoms in the methylene groups which have been replaced by an oxygen atom or a carbonyl group.

Specific examples of the divalent saturated hydrocarbon groups for $L^{b2}$, $L^{b3}$, $L^{b4}$, $L^{b5}$, $L^{b6}$ and $L^{b7}$ include the same as referred to for $L^{b1}$.

$L^{b2}$ is preferably a single bond.
$L^{b3}$ is preferably a C1-C4 alkanediyl group.
$L^{b4}$ is preferably a C1-C8 divalent saturated hydrocarbon group where a hydrogen atom may be replaced by a fluorine atom.
$L^{b5}$ is preferably a single bond or a C1-C8 divalent saturated hydrocarbon group.
$L^{b6}$ is preferably a single bond or a C1-C4 divalent saturated hydrocarbon group where a hydrogen atom can be replaced by a fluorine atom.
$L^{b7}$ is preferably a single bond or a C1-C18 divalent saturated hydrocarbon group where a hydrogen atom can be replaced by a fluorine atom or a hydroxy group, and where a methylene group can be replaced by —O— or —CO—.

As $L^{b1}$, the divalent saturated hydrocarbon group where a methylene group has been replaced by —O— or —CO— is preferably one represented by formula (b1-1) or (b1-3).

Examples of one represented by formula (b1-1) include those represented by formulae (b1-4) to (b1-8).

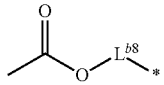  (b1-4)

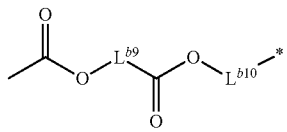  (b1-5)

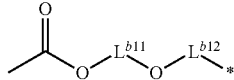  (b1-6)

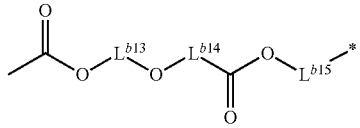  (b1-7)

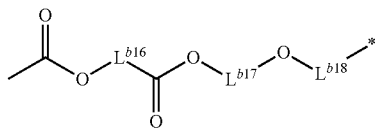  (b1-8)

In these formulae, * represents a binding site to the ring W.

In formula (b1-4), $L^{b8}$ represents a single bond or a C1-C22 divalent saturated hydrocarbon group where a hydrogen atom can be replaced by a fluorine atom or a hydroxy group.

In formula (b1-5), $L^{b9}$ represents a C1-C20 divalent saturated hydrocarbon group and $L^{b10}$ represents a single bond or a C1-C19 divalent saturated hydrocarbon group where a hydrogen atom can be replaced by a fluorine atom or a hydroxy group, provided that total carbon atoms in $L^{b9}$ and $L^{b10}$ are 20 or less.

In formula (b1-6), $L^{b11}$ represents a C1-C21 divalent saturated hydrocarbon group and $L^{b12}$ represents a single bond or a C1-C20 divalent saturated hydrocarbon group where a hydrogen atom can be replaced by a fluorine atom or a hydroxy group, provided that total carbon atoms in $L^{b11}$ and $L^{b12}$ are 21 or less.

In formula (b1-7), $L^{b13}$ represents a C1-C19 divalent saturated hydrocarbon group, $L^{b14}$ represents a single bond or a C1-C18 divalent saturated hydrocarbon group and $L^{b15}$ represents a single bond or a C1-C18 divalent saturated hydrocarbon group where a hydrogen atom can be replaced by a fluorine atom or a hydroxy group, provided that total carbon atoms in $L^{b13}$, $L^{b14}$ and $L^{b15}$ are 19 or less.

In formula (b1-8), $L^{b16}$ represents a C1-C18 divalent saturated hydrocarbon group, $L^{b17}$ represents a C1-C18 divalent saturated hydrocarbon group and $L^{b18}$ represents a single bond or a C1-C17 divalent saturated hydrocarbon group where a hydrogen atom can be replaced by a fluorine atom or a hydroxy group, provided that total carbon atoms in $L^{b16}$, $L^{b17}$ and $L^{b18}$ are 19 or less.

$L^{b8}$ is preferably a C1-C4 alkanediyl group.
$L^{b9}$ is preferably a C1-C8 divalent saturated hydrocarbon group.
$L^{b10}$ is preferably a single bond or a C1-C19 divalent saturated hydrocarbon group, more preferably a single bond or a C1-C8 divalent saturated hydrocarbon group.
$L^{b11}$ is preferably a C1-C8 divalent saturated hydrocarbon group
$L^{b12}$ is preferably a single bond or a C1-C8 divalent saturated hydrocarbon group.

$L^{b13}$ is preferably a Divalent C1-C12 saturated hydrocarbon group.

$L^{b14}$ is preferably a single bond or a C1-C6 divalent saturated hydrocarbon group.

$L^{b15}$ is preferably a single bond or a C1-C18 divalent saturated hydrocarbon group, more preferably a single bond or a C1-C8 divalent saturated hydrocarbon group.

$L^{b16}$ is preferably a Divalent C1-C12 saturated hydrocarbon group.

$L^{b17}$ is preferably a C1-C6 divalent saturated hydrocarbon group.

$L^{b18}$ is preferably a single bond or a C1-C17 divalent saturated hydrocarbon group, more preferably a single bond or a C1-C4 divalent saturated hydrocarbon group.

Examples of the group represented by formula (b1-4) include the following ones.

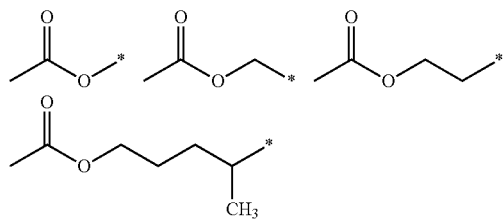

In each formula, * represents a binding site to the ring W.

Examples of the group represented by formula (b1-5) include the following ones.

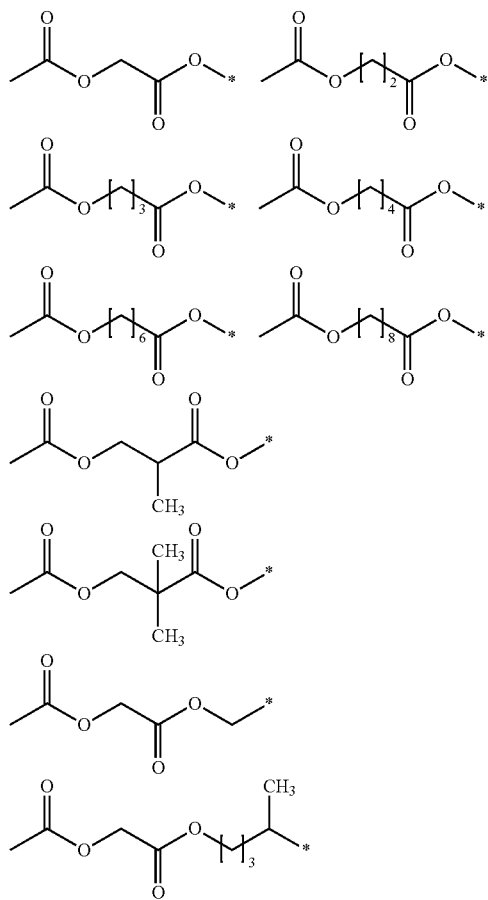

-continued

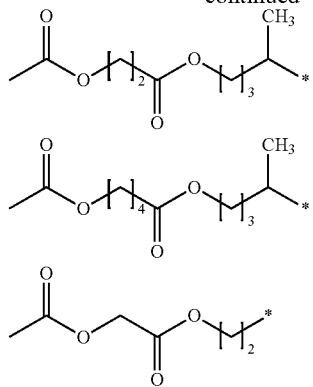

In each formula, * represents a binding site to the ring W.

Examples of the group represented by formula (b1-6) include the following ones.

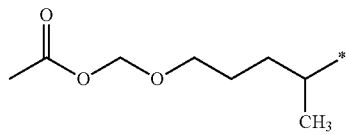

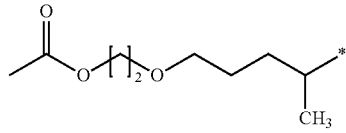

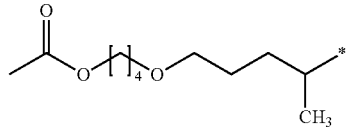

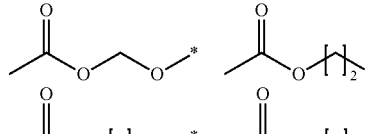

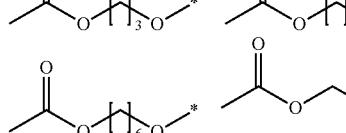

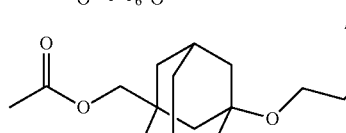

In each formula, * represents a binding site to the ring W.

Examples of the group represented by formula (b1-7) include the following ones.

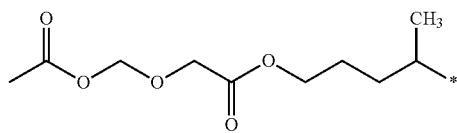

-continued

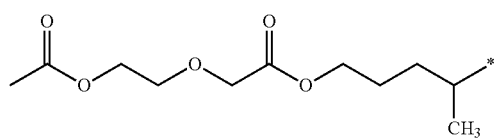

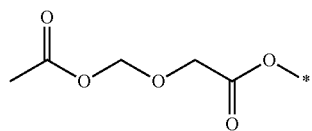

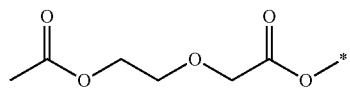

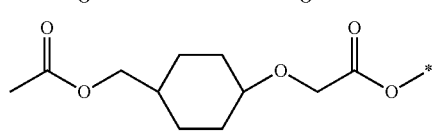

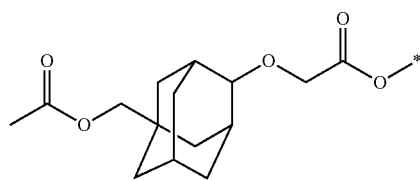

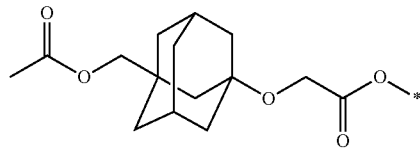

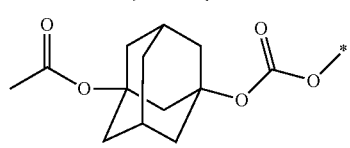

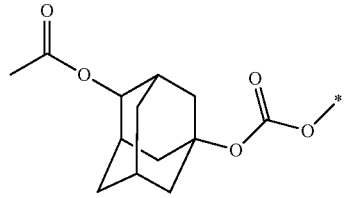

In each formula, * represents a binding site to the ring W.

Examples of the group represented by formula (b1-8) include the following ones.

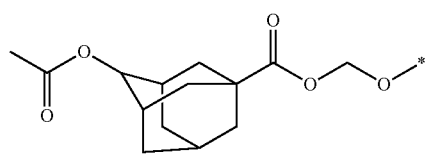

-continued

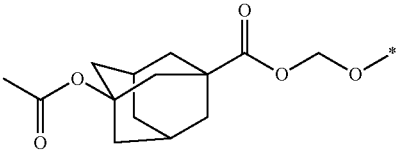

In each formula, * represents a binding site to the ring W.

Examples of the group represented by formula (b1-2) include the following ones.

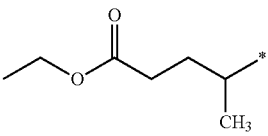

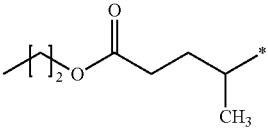

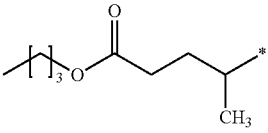

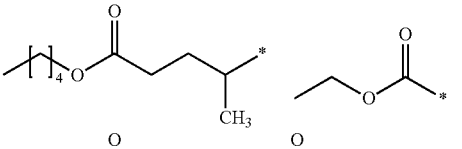

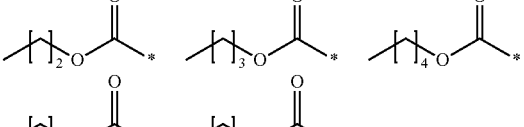

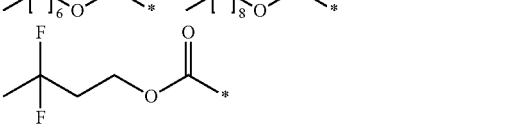

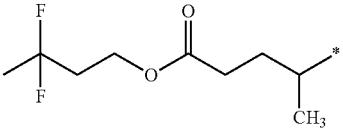

In each formula, * represents a binding site to the ring W.

Examples of one represented by formula (b1-3) include those represented by formulae (b1-9) to (b1-11).

(b1-9)

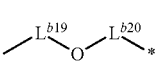

(b1-10)

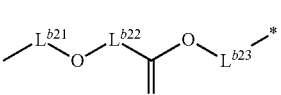

(b1-11)

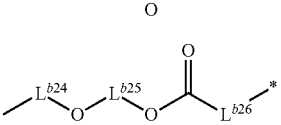

In these formulae, * represents a binding site to the ring W.

In formula (b1-9), $L^{b19}$ represents a single bond or a C1-C23 divalent saturated hydrocarbon group where a hydrogen atom can be replaced by a fluorine atom and $L^{b20}$ represents a single bond or a C1-C23 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b19}$ and $L^{b20}$ are 23 or less.

In formula (b1-10), $L^{b21}$ represents a single bond or a C1-C21 divalent saturated hydrocarbon group where a hydrogen atom can be replaced by a fluorine atom, $L^{b22}$ represents a single bond or a C1-C21 divalent saturated hydrocarbon group and $L^{b23}$ represents a single bond or a C1-C21 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b21}$, $L^{b22}$ and $L^{b23}$ are 21 or less.

In formula (b1-11), $L^{b24}$ represents a single bond or a C1-C20 divalent saturated hydrocarbon group where a hydrogen atom can be replaced by a fluorine atom, $L^{b25}$ represents a C1-C21 divalent saturated hydrocarbon group and $L^{b26}$ represents a single bond or a C1-C20 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b24}$, $L^{b25}$ and $L^{b25}$ are 21 or less.

In formulae (b1-9) to (b1-11), the number of the carbon atoms for the divalent saturated hydrocarbon groups include that of the carbon atoms in an acyloxy group, if a hydrogen atom therein has been replaced by the group.

Examples of acyloxy group include an acetyloxy group, a propionyloxy group, a butyryloxy group, a cyclohexylcarbonyloxy group, and an adamant ylcarbonyloxy group.

Examples of acyloxy group which has a substituent include an oxoadamantylcarbonyloxy group, a hydroxyadamantylcarbonyloxy group, an oxocyclohexylcarbonyloxy group, and a hydroxycyclohexylcarbonyloxy group.

Examples of the group represented by formula (b1-9) include the following ones.

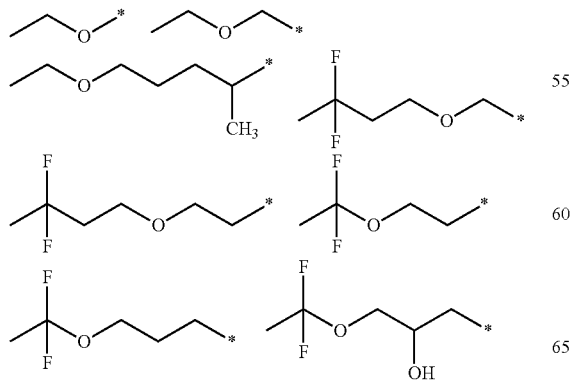

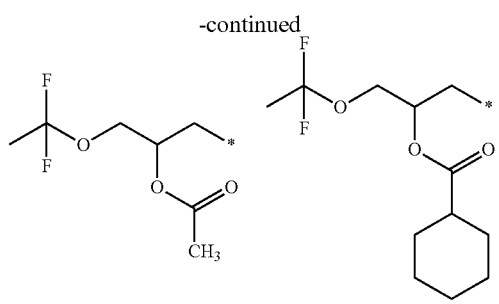

In each formula, * represents a binding site to the ring W.

Examples of the group represented by formula (b1-10) include the following ones.

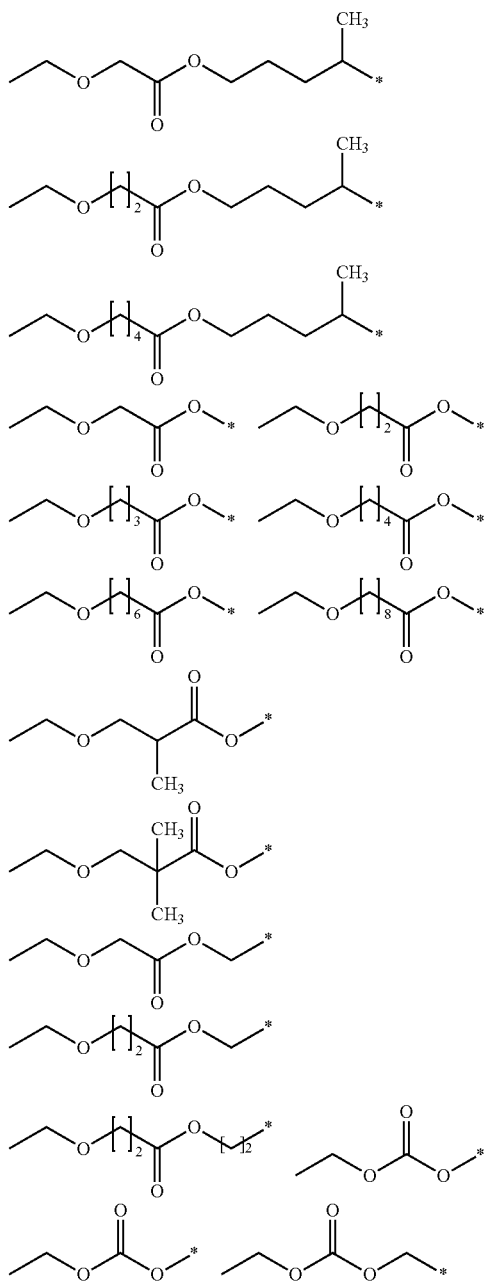

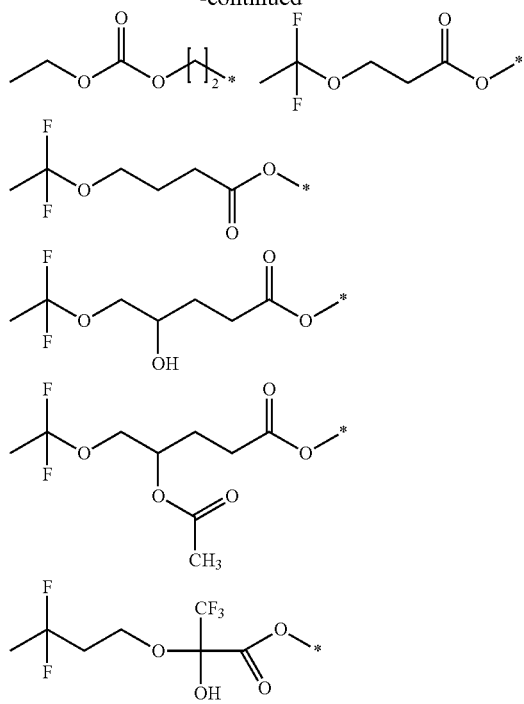
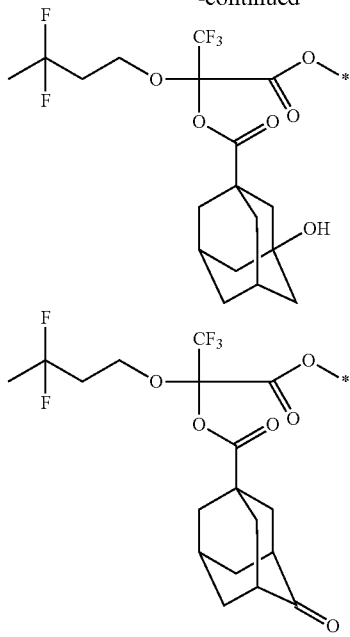
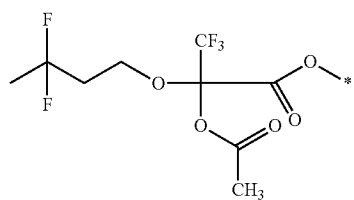
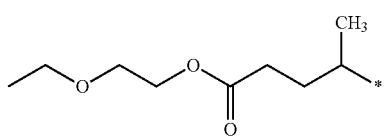
In each formula, * represents a binding site to the ring W.
Examples of the group represented by formula (b1-11) include the following ones.
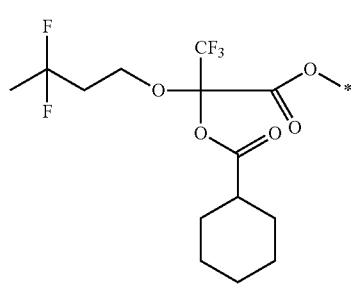
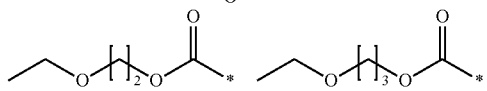
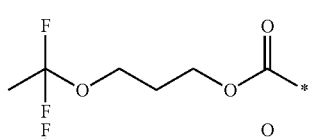
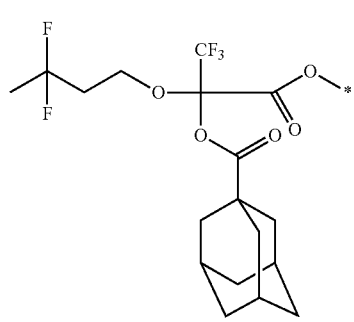
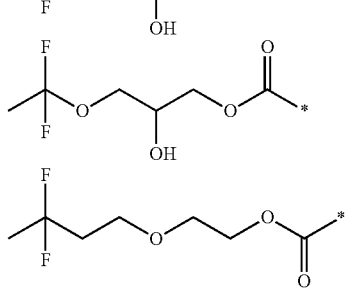

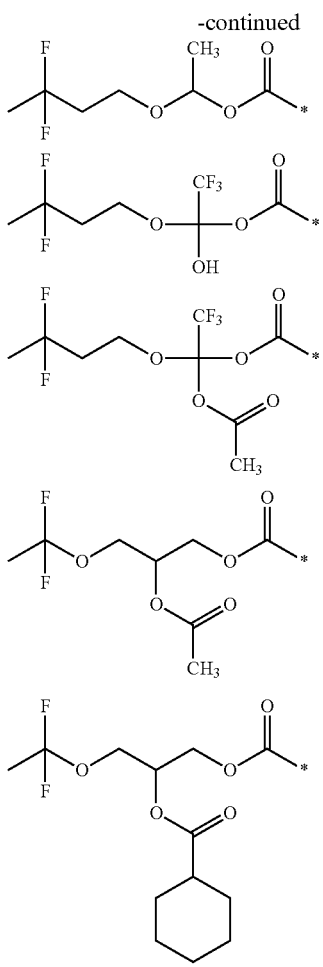

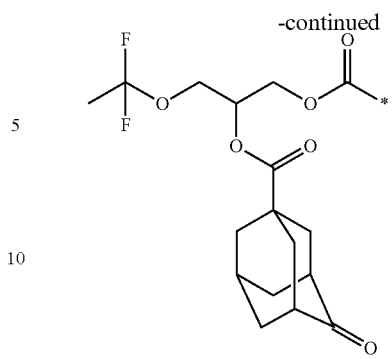

In each formula, * represents a binding site to the ring W.

$L^{b1}$ represents preferably a divalent saturated hydrocarbon group where a methylene group has been replaced by —O— or —CO—. Specifically, $L^{b1}$ represents preferably a group represented by formula (b1-1) or (b1-3), more preferably a group represented by formula (b1-4), still more preferably *—CO—O—(CH$_2$)$_t$— where t is an integer of 0 to 6 and * represents a binding site to C(Q$^1$)(Q$^2$), or *—CH$_2$—O—CO— where * represents a binding site to C(Q$^1$)(Q$^2$), and further more preferably *—CO—O—(CH$_2$)$_t$— where t is as defined above. As to $L^{b1}$, "t" is preferably an integer of 0 or 1.

As to the organic anion of A$^-$, examples of the base-labile group include one represented as follows:

$$*—X^{f1}—R^{f11} \quad (1\text{-}b)$$

in which $R^{f11}$ represents a C1-C12 fluoroalkyl group, $X^{f1}$ represents a carbonyloxy group or an oxycarbonyl group, and represents a binding site.

For $R^{f11}$, examples of the fluoroalkyl group include the same as referred for $R^{f1}$ and $R^{f2}$, preferably a C1-C6 fluoroalkyl group.

When $X^{f1}$ represents an oxycarbonyl group, i.e., when an oxygen atom is directly bonded to $R^{f11}$, $R^{f11}$ is preferably one represented by formula (1-b-1):

$$*—CH_2—R^{f12} \quad (1\text{-}b\text{-}1)$$

in which $R^{f12}$ represents a C1-C5 fluoroalkyl group.

For $R^{f12}$, examples of the fluoroalkyl group include a trifluoromethyl group, difluoromethyl group, a perfluoroethyl group, 2,2,2-trifluoroethyl group, heptafluoropropyl group, 1,1,1,2,3,3,3-heptafluoroisopropyl group, 1,1,1,3,3,3-hexafluoroisopropyl group, perfluoropropyl group, 2,2,3,3,3-pentafluoropropyl group, 3,3,3-trifluoropropyl group, perfluorobutyl group, 2,2,3,3,3,4,4-pentafluorobutyl group, 4,4,4-trifluorobutyl group, 5,5,5-trifluoropentyl group, 4,4,5,5,5-pentafluoropentyl group, 2,2,3,3,4,4,5,5,5-nonafluoropentyl group, perfluoropentyl group, and 1,1,1,2,2,3,3,4,4-nonafluoropentyl group, preferably a C1-C5 perfluoroalkyl group, and more preferably a C1-C3 perfluoroalkyl group.

The base-labile group is preferably one represented by formula (Ba) or formula (Bb):

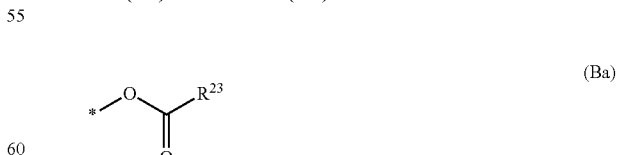

(Ba)

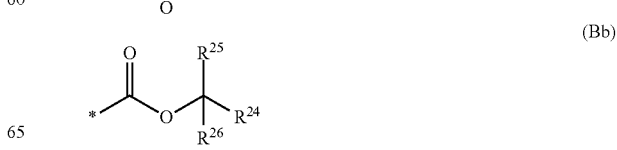

(Bb)

in which $R^{23}$ represents a C1-C6 fluoroalkyl group, $R^{24}$ represents a C1-C5 fluoroalkyl group, $R^{25}$ and $R^{26}$ each independently represent a hydrogen atom or a fluorine atom.

For $R^{23}$, examples of the fluoroalkyl group include preferably a trifluoromethyl group, a perfluoroethyl group, 1,1,1,2,2-pentafluoropropyl group, perfluoropropyl group, 1,1,1,2,3,3,3,4,4-heptafluorobutyl group, perfluorobutyl group, 1,1,1,2,2,3,3,3,4,4-nonafluoropentyl group, perfluoropentyl group and perfluorohexyl group.

For $R^{24}$, examples of the fluoroalkyl group include preferably a trifluoromethyl group, a perfluoroethyl group, 1,1,1,2,2-pentafluoropropyl group, perfluoropropyl group, 1,1,1,2,3,3,3,4,4-heptafluorobutyl group, perfluorobutyl group, 1,1,1,2,2,3,3,3,4,4-nonafluoropentyl group and perfluoropentyl group.

The group represented by formula (Ba) is usually converted to a hydroxy group when it is decomposed by action of an alkali, as shown below. The group represented by formula (Bb) is usually converted to a carboxy group when it is decomposed by action of an alkali, as shown below.

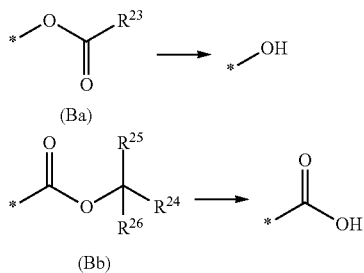

(Ba)

(Bb)

Whether a salt has a base-labile group or not can be determined by the method as follows:

First the acid generator is dissolved in a solvent such as dimethylformamide or other organic solvents, followed by adding thereto an alkaline solution such as tetramethylammonium hydroxide solution. Then the resulting mixture is heated to thereby convert a base-labile group to an alkaline-soluble group such as a hydroxy group or a carboxy group. In the method, the presence of the alkaline-soluble group can be determined by measuring acidity, or by NMR or MS measurement.

The organic anion which has a base-labile group is an anion represented by formula (I-Ba) or formula (I-Bb):

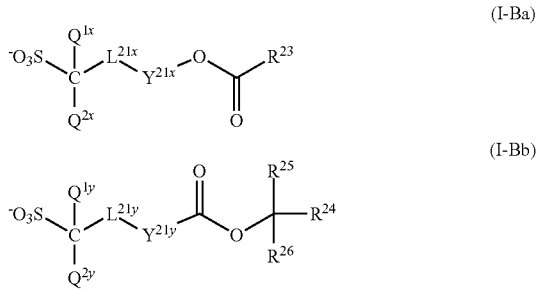

(I-Ba)

(I-Bb)

in which $Q^{1x}$, $Q^{2x}$, $Q^{1y}$ and $Q^{2y}$ each independently represent a fluorine atom or a C1-C6 perfluroalkyl group;

$L^{21x}$ and $L^{21y}$ each independently represent a single bond or a C1-C17 alkanediyl group in which a methyelene group can be replaced by an oxygen atom or a carbonyl group;

$Y^{21x}$ and $Y^{21y}$ each independently represent a C3-C18 divalent alicyclic hydrocarbon group in which a methyelene group can be replaced by an oxygen atom or a carbonyl group; and $R^{23}$, $R^{24}$, $R^{25}$ and $R^{26}$ are as defined above.

For $Q^{1x}$, $Q^{2x}$, $Q^{1y}$ and $Q^{2y}$, examples of the perfluroalkyl group include the same as those referring for $Q^1$ and $Q^2$.

Each of $Q^{1x}$, $Q^{2x}$, $Q^{1y}$ and $Q^{2y}$ is preferably a trifluoromethyl group or a fluorine atom, more preferably a fluorine atom.

For $L^{21x}$ and $L^{21y}$, examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group. For $L^{21x}$ and $L^{21y}$, specific examples of the alkandiyl group where a methylene group has been replaced by an oxygen atom or a carbonyl group include those which have 17 or less carbon atoms and are represented by formulae (b1-1) to (b1-11).

$L^{21x}$ and $L^{21y}$ represents preferably those which have 17 or less carbon atoms and are represented by formula (b1-1) or (b1-3), more preferably those which have 17 or less carbon atoms and are represented by formula (b1-4), still more preferably formula (b1-4) where $L^{b4}$ is a single bond or a C1-C6 alkanediyl group.

As to $L^{21x}$ and $L^{21y}$, specifically preferred is *—CO—O—(CH$_2$)$_u$— where u is an integer of 0 to 6 and * represents a binding site to $C(Q^{1x})(Q^{2x})$ or $C(Q^{1y})(Q^{2y})$, and specifically more preferred are *—CO—O—CH$_2$— and *—CO—O— where * is as defined above.

For $Y^{21x}$ and $Y^{21y}$, examples of the divalent alicyclic hydrocarbon group include divalent monocyclic alicyclic saturated hydrocarbon groups including cycloalkanediyl groups such as a cyclobutane-1,3-diyl group, a cyclopentane-1,3-diyl group, a cyclohexane-1,4-diyl group, and a cyclooctane-1,5-diyl group; and divalent polycyclic saturated hydrocarbon groups such as a norbornane-1,4-diyl group, a norbornane-2,5-diyl group, an adamantane-1,5-diyl group, an adamantane-2,6-diyl group.

Specific examples of the divalent alicyclic hydrocarbon group include the following ones.

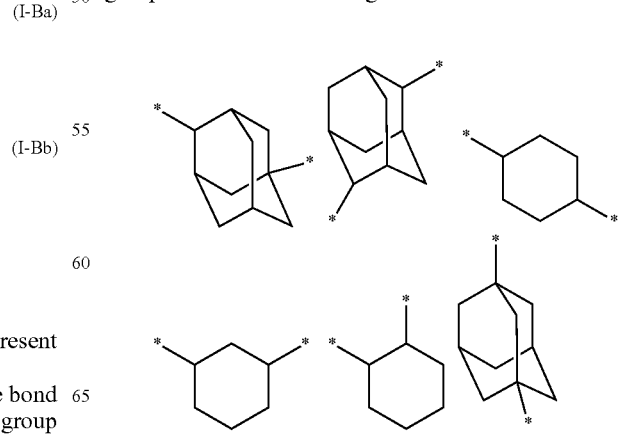

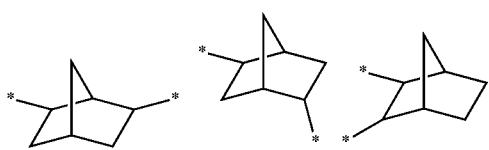

Specific examples of the divalent alicyclic hydrocarbon group in which a methyelene group can be replaced by an oxygen atom or a carbonyl group include the following ones.

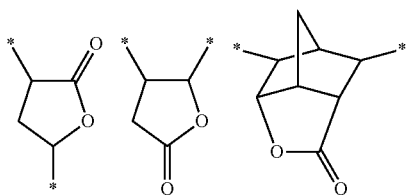

Each of $Y^{21x}$ and $Y^{21y}$ is preferably a divalent polycyclic saturated hydrocarbon group, more preferably a divalent polycyclic saturated hydrocarbon group comprising an adamantane ring, and still more preferably an adamantanediyl group.

Specific examples of the anion represented by $A^-$ include the followings.

(Ia-2-1)
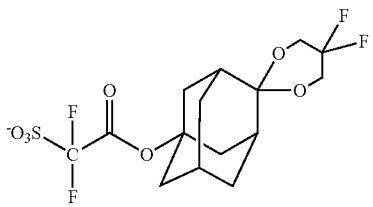

(Ia-2-2)
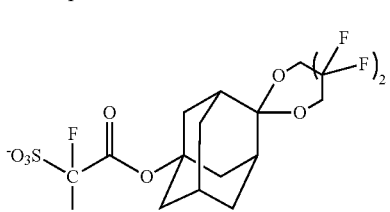

(Ia-2-3)
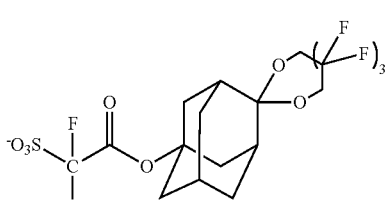

(Ia-2-4)
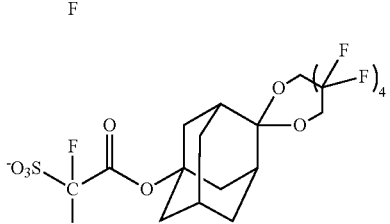

(Ia-2-5)
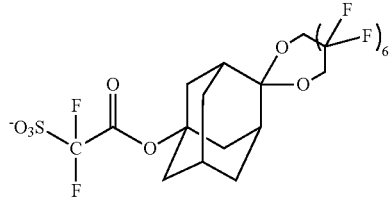

(Ia-2-6)
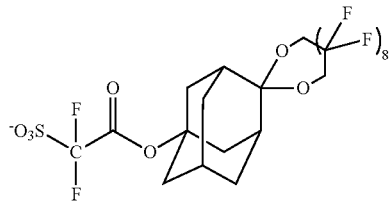

(Ia-2-7)
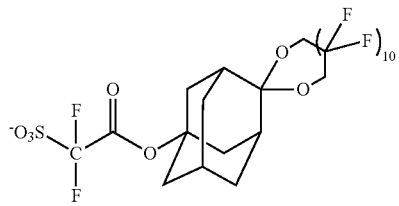

(Ia-2-8)
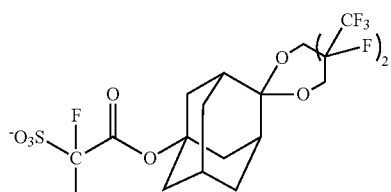

(Ia-2-9)
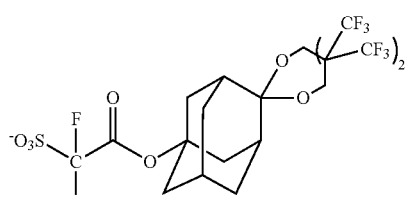

(Ia-2-10)
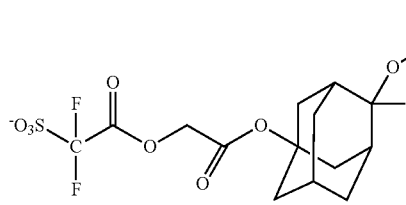

(Ia-2-11)
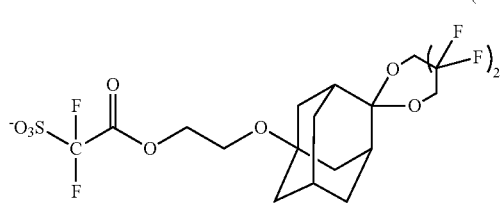

(Ia-2-12)
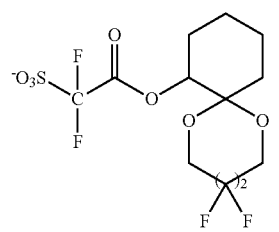

(Ia-2-13)
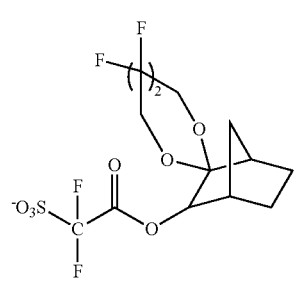

(Ia-2-14)
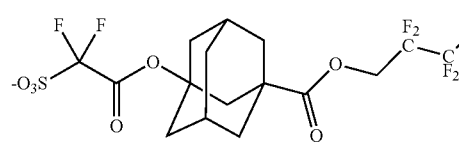

(Ia-2-15)
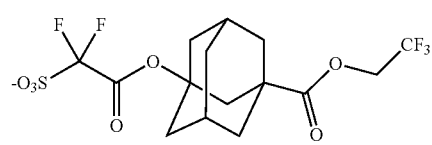

(Ia-2-16)

(Ia-2-17)
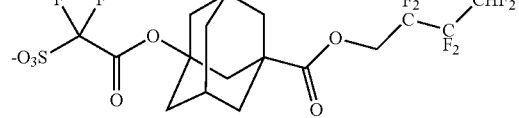

(Ia-2-18)
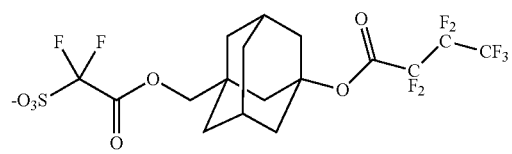

(Ia-2-19)
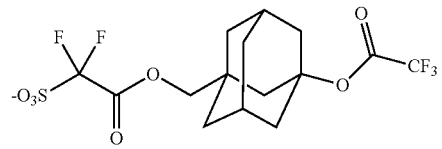

(Ia-2-20)
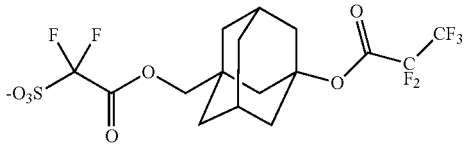

(Ia-2-21)
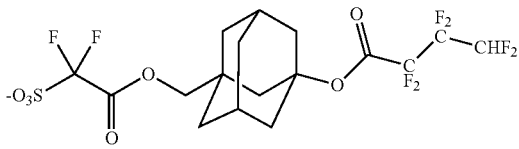

(Ia-2-22)
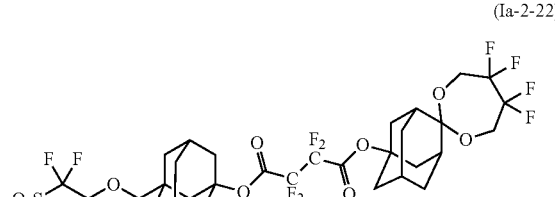

(Ia-2-23)
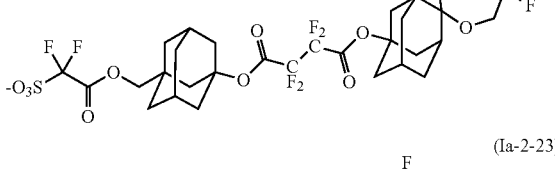

(Ia-2-24)
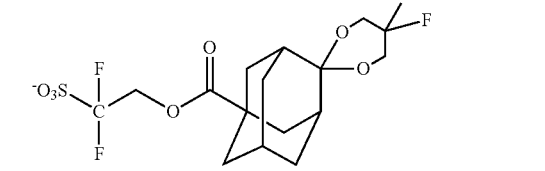

(Ia-2-25)
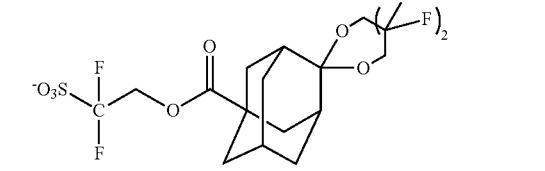

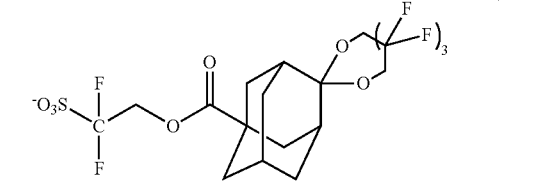

Among the specific examples, as to the organic anion which has an acid-labile group, A⁻ is preferably one represented by formulae (Ia-2-1) to (Ia-2-9).

Among the specific examples, as to the organic anion which has a base-labile group, A⁻ is preferably one represented by formulae (Ia-2-14) and (Ia-2-18).

Specific examples of the salt represented by formula (I) include those as listed in Tables 1 to 3.

In the Tables, a symbol in each column represents the symbol of the formula which represents one anion or cation as mentioned above.

For example, the salt referred to as "(I-1)" represents the following one.

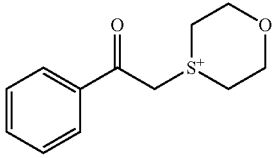

(I-1)

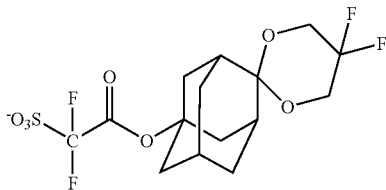

TABLE 1

| Salt | anion | cation |
|---|---|---|
| (I-1) | (Ia-2-1) | (I-c-1) |
| (I-2) | (Ia-2-2) | (I-c-1) |
| (I-3) | (Ia-2-3) | (I-c-1) |
| (I-4) | (Ia-2-4) | (I-c-1) |
| (I-5) | (Ia-2-1) | (I-c-2) |
| (I-6) | (Ia-2-2) | (I-c-2) |
| (I-7) | (Ia-2-3) | (I-c-2) |
| (I-8) | (Ia-2-4) | (I-c-2) |
| (I-9) | (Ia-2-1) | (I-c-3) |
| (I-10) | (Ia-2-2) | (I-c-3) |
| (I-11) | (Ia-2-3) | (I-c-3) |
| (I-12) | (Ia-2-4) | (I-c-3) |
| (I-13) | (Ia-2-1) | (I-c-4) |
| (I-14) | (Ia-2-2) | (I-c-4) |
| (I-15) | (Ia-2-3) | (I-c-4) |
| (I-16) | (Ia-2-4) | (I-c-4) |
| (I-17) | (Ia-2-1) | (I-c-5) |
| (I-18) | (Ia-2-2) | (I-c-5) |
| (I-19) | (Ia-2-3) | (I-c-5) |
| (I-20) | (Ia-2-4) | (I-c-5) |
| (I-21) | (Ia-2-1) | (I-c-6) |
| (I-22) | (Ia-2-2) | (I-c-6) |
| (I-23) | (Ia-2-3) | (I-c-6) |
| (I-24) | (Ia-2-4) | (I-c-6) |

TABLE 2

| Salt | anion | cation |
|---|---|---|
| (I-25) | (Ia-2-1) | (I-c-7) |
| (I-26) | (Ia-2-2) | (I-c-7) |
| (I-27) | (Ia-2-3) | (I-c-7) |
| (I-28) | (Ia-2-4) | (I-c-7) |
| (I-29) | (Ia-2-1) | (I-c-8) |
| (I-30) | (Ia-2-2) | (I-c-8) |
| (I-31) | (Ia-2-3) | (I-c-8) |
| (I-32) | (Ia-2-4) | (I-c-8) |
| (I-33) | (Ia-2-5) | (I-c-1) |
| (I-34) | (Ia-2-6) | (I-c-1) |
| (I-35) | (Ia-2-7) | (I-c-1) |
| (I-36) | (Ia-2-8) | (I-c-1) |
| (I-37) | (Ia-2-9) | (I-c-1) |
| (I-38) | (Ia-2-5) | (I-c-5) |
| (I-39) | (Ia-2-6) | (I-c-5) |
| (I-40) | (Ia-2-7) | (I-c-5) |
| (I-41) | (Ia-2-8) | (I-c-5) |
| (I-42) | (Ia-2-9) | (I-c-5) |
| (I-43) | (Ia-2-16) | (I-c-1) |
| (I-44) | (Ia-2-17) | (I-c-1) |
| (I-45) | (Ia-2-20) | (I-c-1) |
| (I-46) | (Ia-2-21) | (I-c-1) |
| (I-47) | (Ia-2-16) | (I-c-2) |
| (I-48) | (Ia-2-17) | (I-c-2) |
| (I-49) | (Ia-2-20) | (I-c-2) |

TABLE 2-continued

| Salt | anion | cation |
|---|---|---|
| (I-50) | (Ia-2-21) | (I-c-2) |
| (I-51) | (Ia-2-16) | (I-c-3) |
| (I-52) | (Ia-2-17) | (I-c-3) |
| (I-53) | (Ia-2-20) | (I-c-3) |
| (I-54) | (Ia-2-21) | (I-c-4) |
| (I-55) | (Ia-2-14) | (I-c-1) |
| (I-56) | (Ia-2-14) | (I-c-2) |
| (I-57) | (Ia-2-14) | (I-c-3) |
| (I-58) | (Ia-2-14) | (I-c-4) |
| (I-59) | (Ia-2-14) | (I-c-5) |
| (I-60) | (Ia-2-14) | (I-c-6) |
| (I-61) | (Ia-2-14) | (I-c-7) |
| (I-62) | (Ia-2-14) | (I-c-8) |
| (I-63) | (Ia-2-18) | (I-c-1) |
| (I-64) | (Ia-2-18) | (I-c-2) |
| (I-65) | (Ia-2-18) | (I-c-3) |
| (I-66) | (Ia-2-18) | (I-c-4) |
| (I-67) | (Ia-2-18) | (I-c-5) |
| (I-68) | (Ia-2-18) | (I-c-6) |

TABLE 3

| Salt | anion | cation |
|---|---|---|
| (I-69) | (Ia-2-18) | (I-c-7) |
| (I-70) | (Ia-2-18) | (I-c-8) |
| (I-71) | (Ia-2-24) | (I-c-1) |
| (I-72) | (Ia-2-24) | (I-c-2) |
| (I-73) | (Ia-2-24) | (I-c-3) |
| (I-74) | (Ia-2-24) | (I-c-4) |
| (I-75) | (Ia-2-24) | (I-c-5) |
| (I-76) | (Ia-2-24) | (I-c-6) |
| (I-77) | (Ia-2-24) | (I-c-7) |
| (I-78) | (Ia-2-24) | (I-c-8) |

The salt represented by formula (I) is preferably represented by (I-2), (I-3), (I-6), (I-7), (I-10), (I-11), (I-14), (I-15), (I-18), (I-19), (I-23), (I-24), (I-26), (I-27), (I-30), (I-31), (I-55), (I-56), (I-57), (I-58), (I-59), (I-63), (I-64), (I-65), (I-66), (I-67), (I-71), (I-72), (I-73), (I-74) or (I-75), more preferably by (I-2), (I-3), (I-6), (I-7), (I-10), (I-11), (I-14), (I-15), (I-18), (I-19), (I-23), (I-24), (I-26), (I-27), (I-30) or (I-31).

The compound represented by formula (I) can be produced by reacting the compound of formula (IA-a) and the compound of formula (IA-b) in a solvent such as chloroform.

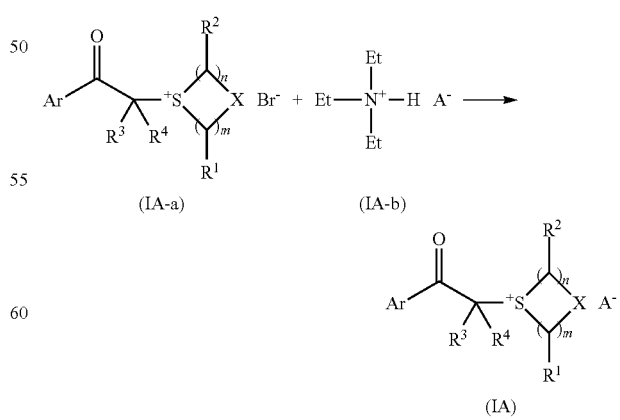

In the formulae, $R^1$, $R^2$, $R^3$, $R^4$, X, Ar, $A^-$, m and n are as defined above.

The reaction can be conducted at temperature of preferably 10° C. to 60° C., for 0.5 to 12 hours.

The compound of formula (IA-a) can be prepared by reacting the compound of formula (IA-c) and the compound of formula (IA-d), in a solvent such as acetone:

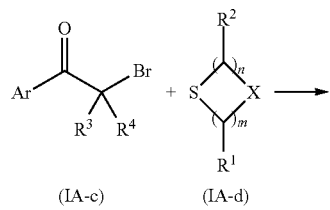

(IA-c)   (IA-d)

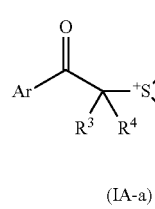

(IA-a)

in which $R^1$, $R^2$, $R^3$, $R^4$, Ar, X, m and n are as defined above.

The reaction can be conducted at temperature of preferably 10° C. to 60° C., for 0.5 to 120 hours.

Examples of the compound of formula (IA-c) include the following one.

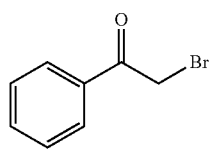

The compound of formulae (IA-c) is available on the market.

Examples of the compound of formula (IA-d) include the following one.

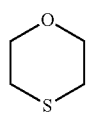

The compound of formula (IA-d) is available on the market.

When $A^-$ represents the anion of formula (a-2), the compound of formula (IA-b) can be prepared by reacting the compound of formula (IA-e) and the compound of formula (IA-f), in the presence of an acid catalyst such as sulfonic acid or p-toluenesulfonic acid, in a solvent such as chloroform, acetonitrile or dimethylformamide:

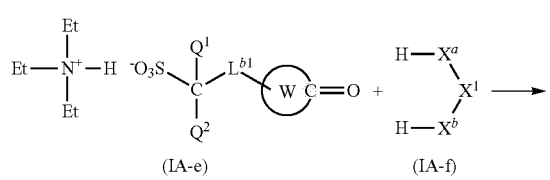

(IA-e)   (IA-f)

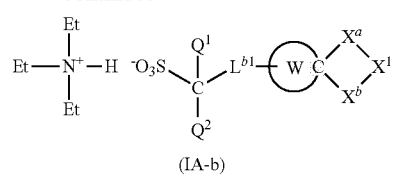

(IA-b)

in which $L^{b1}$, W, $Q^1$, $Q^2$, $X^a$, $X^b$ and $X^1$ are as defined above.

Examples of the compound of formula (IA-e) include the following ones.

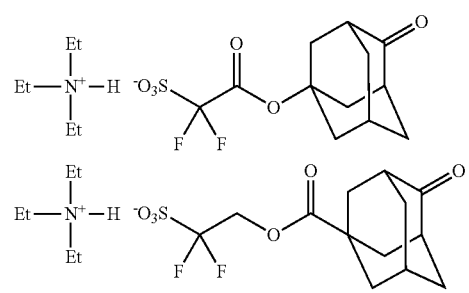

The compound of formula (IA-e) is available on the market and can be prepared according to a method recited in Examples of JP2011-116747A1.

Examples of the compound of formula (IA-f) include the following one.

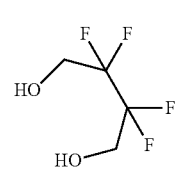

When $A^-$ represents the anion of formula (I-Ba), the compound of formula (IA-b) can be prepared by reacting the compound of formula (IA-g) and the compound of formula (IA-h), in the presence of a basic catalyst such as N-methylpyroridine, in a solvent such as chloroform:

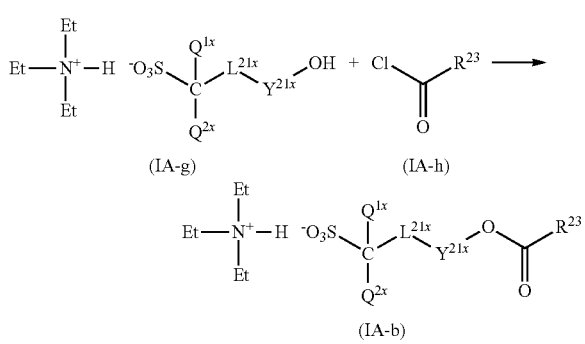

in which $L^{21x}$, $Q^{1x}$, $Q^{2x}$, $Y^{21x}$ and $R^{23}$ are as defined above.

Examples of the compound of formula (IA-g) include the following one.

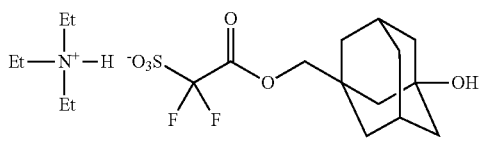

The compound of formula (IA-g) is available on the market and can be prepared according to a method recited in Examples of JP2011-116747A1.

Examples of the compound of formula (IA-h) include heptafluorobutylchloride.

<Acid Generator>

The salt of the formula (I) can be used as an acid generator for photoresist compositions.

In this disclosure, an acid generator which comprises the salt of the formula (I) is one aspect of the invention.

The acid generator of the disclosure may further comprise another salt than the salt of the formula (I).

The another salt may be one known as an acid generator in the art of photoresist compositions, which may be a noionic or ionic salt.

The acid generator known in the art includes those described as acid generators in JP63-26653 A, JP 55-164824 A, JP 62-69263 A, JP 63-146038 A, JP63-163452A, JP62-153853 A, JP63-146029 A, U.S. Pat. No. 3,779,778, U.S. Pat. No. 3,849,137, DE Patent No. 3914407 and EP Patent No. 126,712, JP2013-68914A, JP2013-3155A, and JP2013-11905A, preferably JP2013-68914A, JP2013-3155A, and JP2013-11905A.

The acid generator known in the art is preferably a fluorine-containing acid generator.

Preferable examples of the acid generator known in the art include a salt which comprises an organic sulfonic anion and an organic sulfonium cation.

Preferred examples of the organic organic sulfonium cation include the organic cations represented by the formulae (b2-1), (b2-2), (b2-3) and (b2-4):

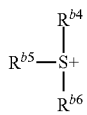
(b2-1)

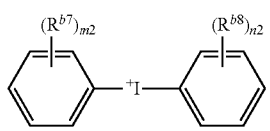
(b2-2)

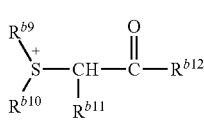
(b2-3)

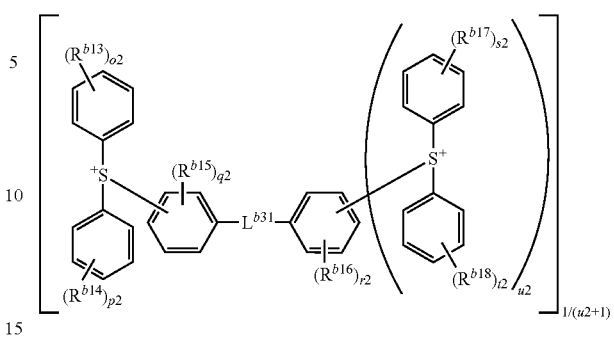
(b2-4)

In the formulae (b2-1) to (b2-4), $R^{b4}$, $R^{b5}$ and $R^{b6}$ independently represent a C1-C30 aliphatic hydrocarbon group, a C3-C36 alicyclic hydrocarbon group and a C6-C36 aromatic hydrocarbon group.

The aliphatic hydrocarbon group can have a substituent selected from the group consisting of a hydroxy group, a C1-C12 alkoxy group, a C3-C12 alicyclic hydrocarbon group and a C6-C18 aromatic hydrocarbon group. The alicyclic hydrocarbon group can have a substituent selected from the group consisting of a C1-C18 aliphatic hydrocarbon group, a C2-C4 acyl group and a glycidyloxy group. The aromatic hydrocarbon group can have a substituent selected from the group consisting of a hydroxy group, a C1-C18 aliphatic hydrocarbon group and a C1-C12 alkoxy group.

$R^{b4}$ and $R^{b5}$ can be bonded to form a ring together with the adjacent $S^+$, and a methylene group in the ring may be replaced by —CO—, —O— or —SO—.

$R^{b7}$ and $R^{b8}$ are independently in each occurrence a hydroxy group, a C1-C12 alkyl group or a C1-C12 alkoxy group, m2 and n2 independently represents an integer of 0 to 5.

$R^{b9}$ and $R^{b10}$ independently represent a C1-C36 aliphatic hydrocarbon group or a C3-C36 alicyclic hydrocarbon group.

$R^{b9}$ and $R^{b10}$ can be bonded to form a ring together with the adjacent $S^+$, and a methylene group in the divalent acyclic hydrocarbon group may be replaced by —CO—, —O— or —SO—.

$R^{b11}$ represents a hydrogen atom, a C1-C36 aliphatic hydrocarbon group, a C3-C36 alicyclic hydrocarbon group or a C6-C18 aromatic hydrocarbon group.

$R^{b12}$ represents a C1-C12 aliphatic hydrocarbon group in which a hydrogen atom can be replaced by a C6-C18 aromatic hydrocarbon group, a C3-C18 saturated cyclic hydrocarbon group and a C6-C18 aromatic hydrocarbon group in which a hydrogen atom can be replaced by a C1-C12 alkoxy group or a (C1-C12 alkyl) carbonyloxy group.

$R^{b11}$ and $R^{b12}$ can be bonded each other to form a C1-C10 divalent acyclic hydrocarbon group which forms a 2-oxocycloalkyl group together with the adjacent —CHCO—, and a methylene group in the divalent acyclic hydrocarbon group may be replaced by —CO—, —O— or —SO—.

$R^{b13}$, $R^{b14}$, $R^{b15}$, $R^{b16}$, $R^{b17}$ and $R^{b18}$ independently represent a hydroxy group, a C1-C12 aliphatic hydrocarbon group or a C1-C12 alkoxy group.

$L^{b31}$ represents —S— or —O— and o2, p2, s2 and t2 each independently represents an integer of 0 to 5, q2 and r2 each independently represents an integer of 0 to 4, and u2 represents 0 or 1.

Preferred examples of the aliphatic hydrocarbon group represented by $R^{b4}$ to $R^{b12}$ include an alkyl group such as a methyl group, an ethyl group, a propyl group, an isopropyl group, a butyl group, a sec-butyl group, a tert-butyl group, a pentyl group, a hexyl group, an octyl group and a 2-ethylhexyl group. The aliphatic hydrocarbon group represented by $R^{b9}$, $R^{b10}$, $R^{b11}$ and $R^{b12}$ has preferably 1 to 12 carbon atoms, more preferably 4 to 12 carbon atoms.

The alicyclic hydrocarbon group may be monocyclic or polycyclic. Preferred examples thereof include a cycloalkyl group such as a cyclopentyl group, a cyclohexyl group, a methylcyclohexyl group, a dimethylcyclohexyl group, a cycloheptyl group and a cyclooctyl group, a group obtained by hydrogenating a condensed aromatic hydrocarbon group such as a hydronaphthyl group, abridged cyclic hydrocarbon group such as an adamantyl group, a norbornyl group and a decahydronaphtyl group, and the following groups.

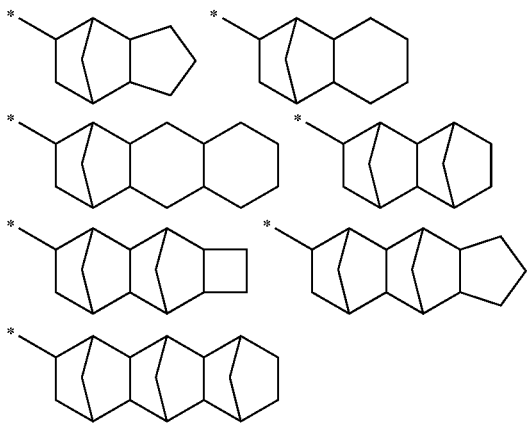

The alicyclic hydrocarbon group represented by $R^{b9}$, $R^{b10}$, $R^{b11}$ and $R^{b12}$ has preferably 3 to 18 carbon atoms, more preferably 4 to 12 carbon atoms.

Examples of the alicyclic hydrocarbon group in which a hydrogen atom has been replaced by an aliphatic hydrocarbon group include a methylcyclohexyl group, a dimethylcyclohexyl group, a methylnorbornyl group, and an isonorbornyl group.

The alicyclic hydrocarbon group in which a hydrogen atom has been replaced by an aliphatic hydrocarbon group has preferably 20 or less carbon atoms in total.

Examples of the aromatic hydrocarbon group include an aryl group such as a phenyl group, tolyl group, xylyl group, cumenyl group, mesityl group, p-ethylphenyl group, p-tert-butylphenyl group, p-adamantylphenyl group, a biphenylyl group, a naphthyl group, a phenanthryl group, a 2,6-diethylphenyl group, a 2-methyl-6-ethylphenyl group.

When the aromatic hydrocarbon group has an alicyclic hydrocarbon group or an aliphatic hydrocarbon group, it is preferred that the alicyclic hydrocarbon group and the aliphatic hydrocarbon group have respectively 1 to 18 carbon atoms and 3 to 18 carbon atoms.

Examples of the aromatic hydrocarbon group in which a hydrogen atom has been replaced by an alkoxy group include p-methoxyphenyl group.

Examples of the aliphatic hydrocarbon group in which a hydrogen atom has been replaced by an aromatic hydrocarbon group include a benzyl group, a phenethyl group, a phenylpropyl group, trityl group, naphthylmethyl group, and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the acyl group include an acetyl group, a propyonyl group and a butyryl group.

Examples of alkylcarbonyloxy group include a methylcarbonyloxy group, an ethylcarbonyloxy group, a n-propylcarbonyloxy group, an isopropylcarbonyloxy group, a n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethyl hexylcarbonyloxy group.

The ring group formed by bonding $R^{b4}$ and $R^{b5}$ together with the adjacent $S^+$ may be monocyclic or polycyclic, saturated or unsaturated, aromatic or nonaromatic group. The ring is generally a 3 to 12-membered, preferably 3 to 7-membered one. Examples of the ring include the following ones.

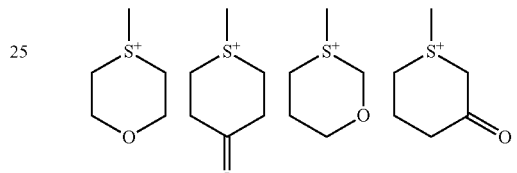

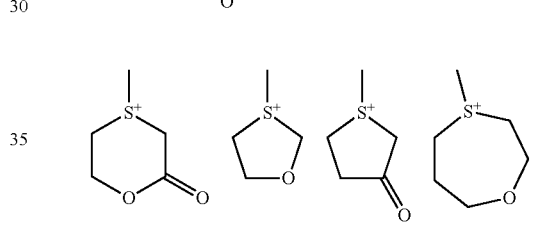

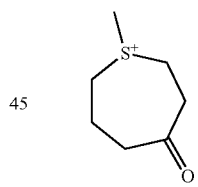

The ring group formed by bonding $R^{b9}$ and $R^{b10}$ together with the adjacent $S^+$ may be monocyclic or polycyclic, saturated or unsaturated, aromatic or nonaromatic group. The ring has generally C3-C12, preferably C3-C7 carbon atoms. Examples of the ring include a thiolan-1-ium ring (tetrahydrothiphenium ring), a thian-1-ium ring and a 1,4-oxathian-4-ium ring.

The ring group formed by bonding $R^{b11}$ and $R^{b12}$ together with —CH—CO— may be monocyclic or polycyclic, saturated or unsaturated, aromatic or nonaromatic group. The ring has generally C3-C12, preferably C3-C7 carbon atoms. Examples of the ring include an oxocycloheptane ring, an oxocyclohexane ring, an oxonorbornane ring, and an oxoadamantane ring.

Preferred examples of the cation for Salt (a) include an arylsulfonium cation, specifically a cation of formula (b2-1), and more specifically a phenylsulfonium cation.

Examples of the sulfonic acid include one represented by formula (B1):

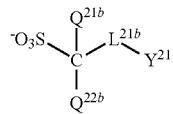
(B1)

wherein $Q^{21b}$ and $Q^{22b}$ independently each represent a fluorine atom or a C1-C6 perfluoroalkyl group;

$L^{21b}$ represents a C1-C24 divalent hydrocarbon group where a methylene group can be replaced by an oxygen atom or a carbonyl group and where a hydrogen atom can be replaced by a fluorine atom or a hydroxy group; and $Y^{21}$ represents a methyl group or a C3-C18 alicyclic hydrocarbon group where a methylene group can be replaced by an oxygen atom, a carbonyl group or a sulfonyl group and where a hydrogen atom can be replaced by a substituent such as a fluorine atom or a hydroxy group.

Specific examples of the acid generator include the following salts represented by formulae (B1-1) to (B1-28). Among them, the salts represented by formulae (B1-1), (B1-2), (B1-3), (B1-6), (B1-7), (B1-11), (B1-12), (B1-13), (B1-14), (B1-20), (B1-21), (B1-22), (B1-23), (B1-24), (B1-25) and (B1-26) are preferred, and the salts represented by formulae (B1-1), (B1-2), (B1-3), (B1-5), (B1-6), (B1-7), (B1-11), (B1-12), (B1-13), (B1-14), (B1-20), (B1-21), (B1-22), (B1-23) and (B1-24) are more preferred.

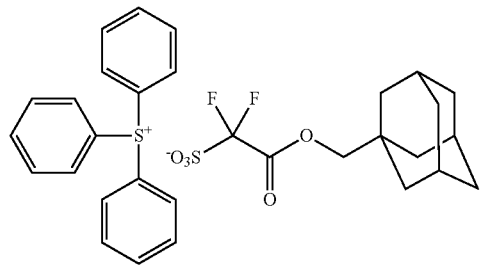
(B1-1)

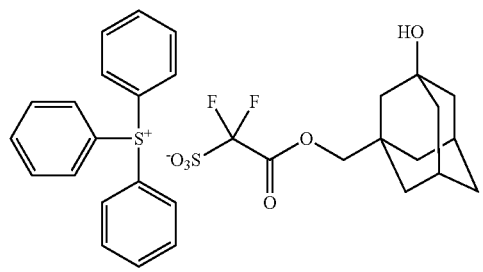
(B1-2)

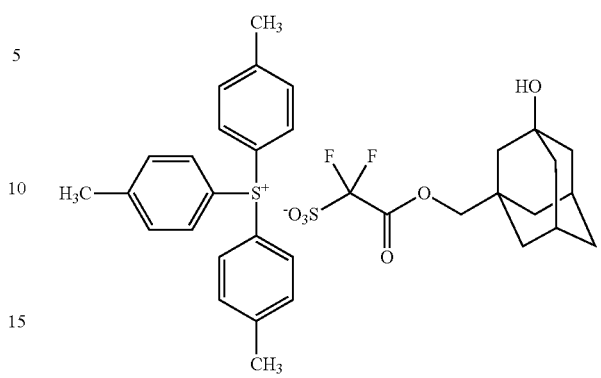
(B1-3)

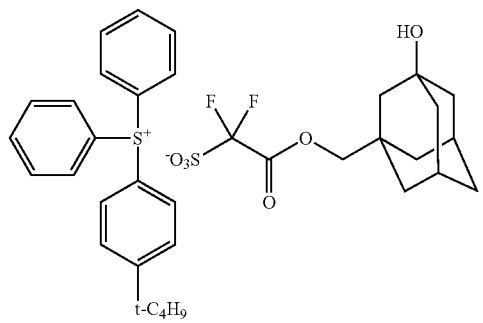
(B1-4)

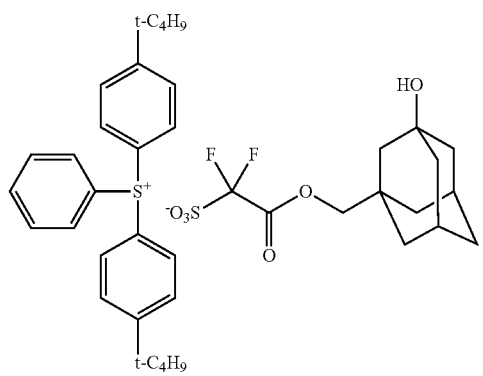
(B1-5)

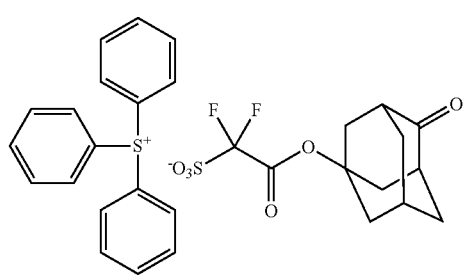
(B1-16)

(B1-7)
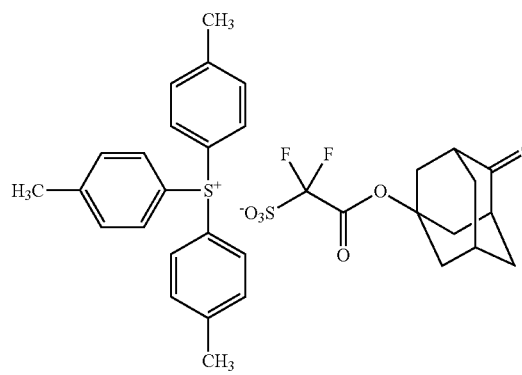
(B1-8)
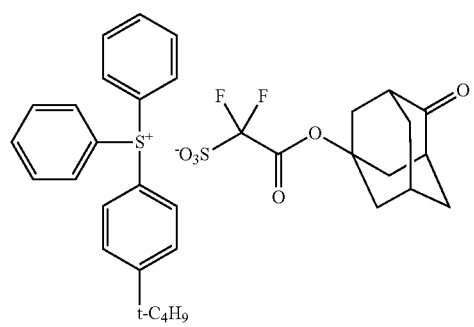
(B1-9)
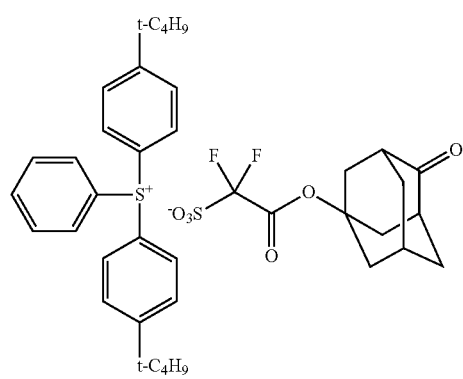
(B1-10)
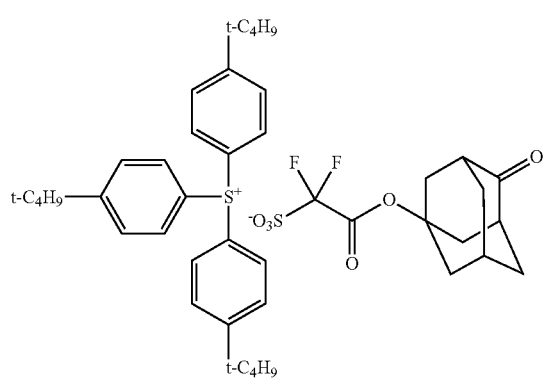
(B1-11)
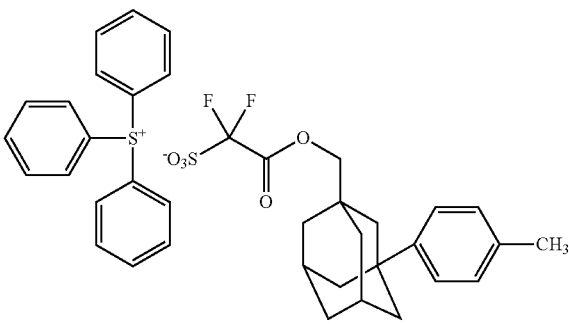
(B1-12)
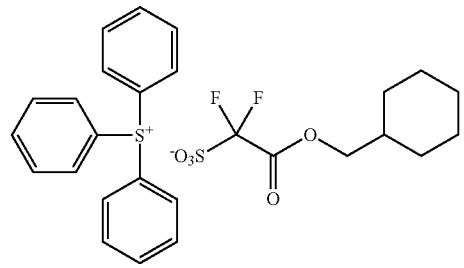
(B1-13)
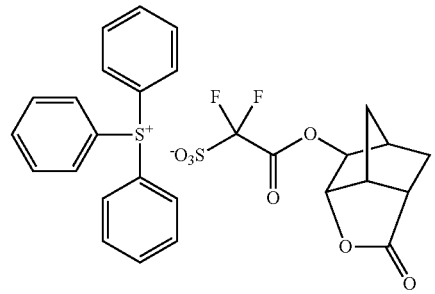
(B1-14)
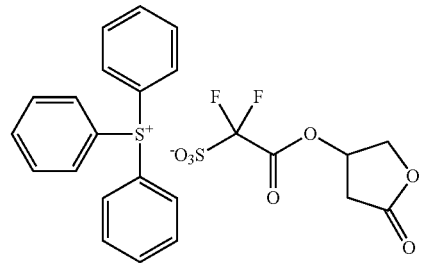
(B1-15)
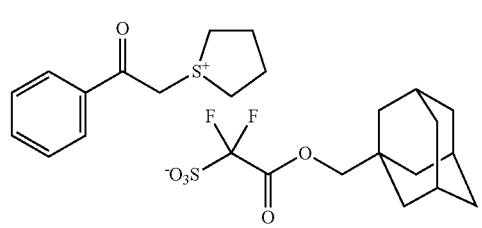

-continued
(B1-16)
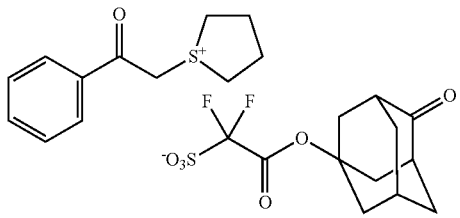
(B1-17)
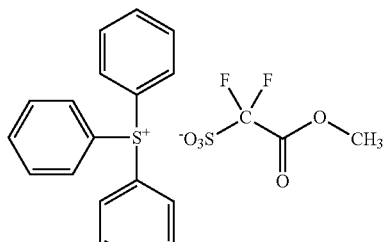
(B1-18)
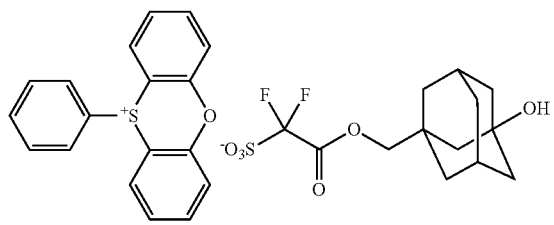
(B1-19)
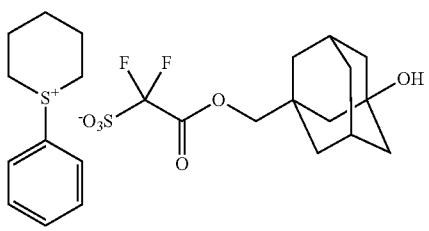
(B1-20)
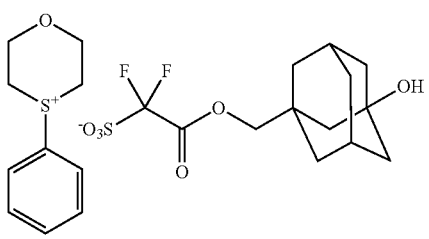
(B1-21)
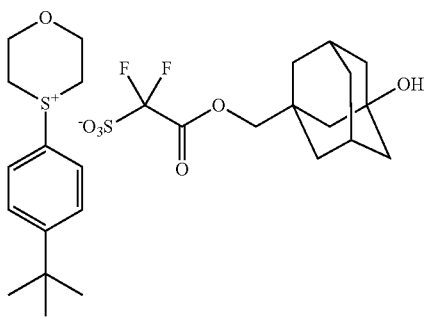
-continued
(B1-22)
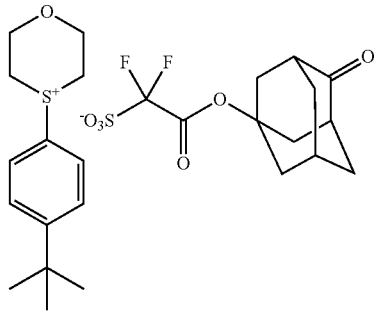
(B1-23)
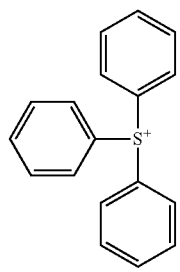
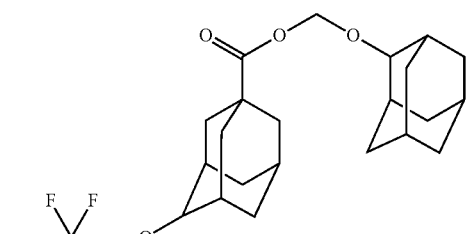
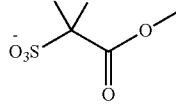
(B1-24)
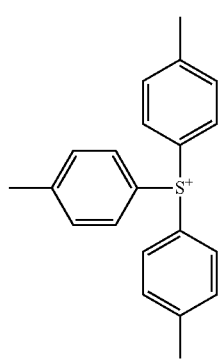
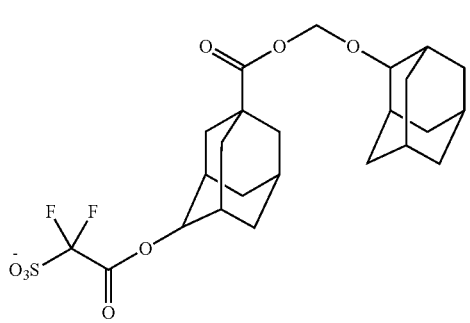

-continued (B1-25)
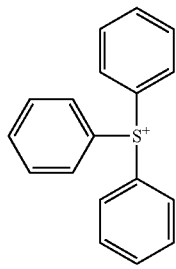

(B1-26)
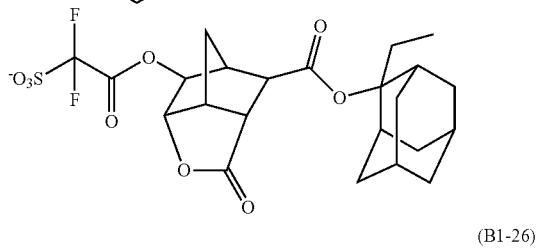

(B1-27)
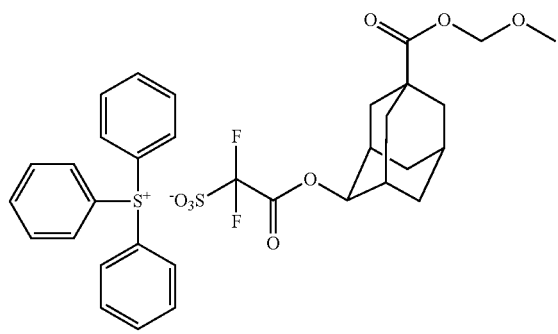

(B1-28)
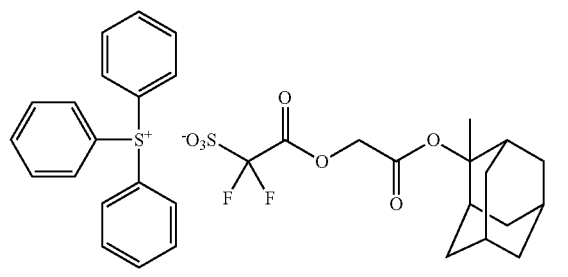

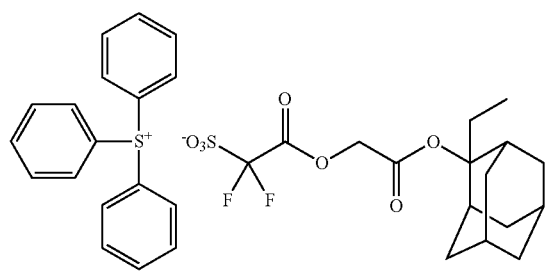

When the acid generator further comprises another salt, the content of the salt represented by formula (I) is preferably 1 to 100 parts by mass, more preferably 20 to 100 parts by mass, relative to 100 parts by mass of the acid generator.

<Photoresist Composition>

In this disclosure, a photoresist composition which comprises the acid generator as mentioned above and a resin having an acid-labile group is also one aspect of the invention.

In the photoresist composition, the total amount of the acid generator is preferably 1.5 to 40 parts by mass, more preferably 3 to 35 parts by mass, relative to 100 parts by mass of the resin having an acid-labile group.

In the photoresist composition, the content of the salt represented by formula (I) is preferably 1 to 20 parts by mass, more preferably 2 to 15 parts by mass, relative to 100 parts by mass of the resin having an acid-labile group.

In the photoresist composition, the content of another salt is preferably 1 to 20 parts by mass, more preferably 3 to 15 parts by mass, relative to 100 parts by mass of the resin having an acid-labile group.

The resin having an acid-labile group, which is sometimes referred to as "Resin (A)", usually comprises a structural unit having an acid-labile group and no fluorine atom. Hereinafter, the structural unit is sometimes referred to as "structural unit (a1)".

Preferably Resin (A) further comprises another structural unit than the structural unit (a1), i.e. a structural unit having no acid-labile group, which is sometimes referred to as "structural unit (s)".

The structural unit (a1) is derived from a compound having an acid-labile group which compound is sometimes referred to as "Monomer (a1)".

Herein, "an acid-labile group" means a group which has a hydrophilic group, such as a hydroxy group or a carboxy group, resulting from removing a leaving group therefrom by the action of an acid.

For Resin (A), the acid-labile groups represented by formulae (1) and (2) are preferred:

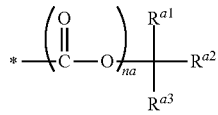

(1)

In formula (1), $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C2-C20 divalent hydrocarbon group, na represents an integer of 0 or 1, and * represents a binding site.

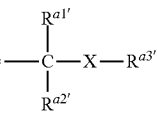

(2)

In formula (2), $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C2-C20 divalent hydrocarbon group, and one or more —CH$_2$— in the hydrocarbon group and the divalent hydrocarbon group can be replaced by —O— or —S—, X represents an oxygen atom or a sulfur atom, and represents a binding site.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

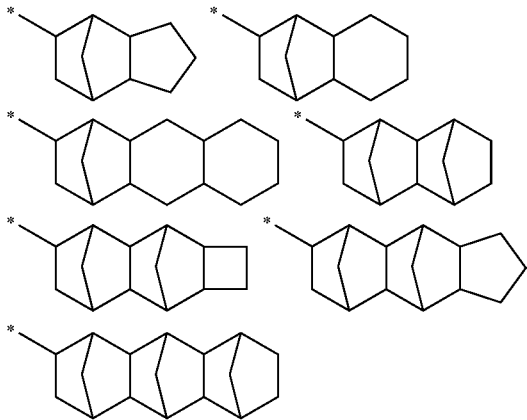

in which * represents a binding site.

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent hydrocarbon group is formed by bonding $R^{a1}$ and $R^{a2}$ each other, examples of the moiety —C($R^{a1}$)($R^{a2}$)($R^{a3}$) include the following groups and the divalent hydrocarbon group preferably has 3 to 12 carbon atoms.

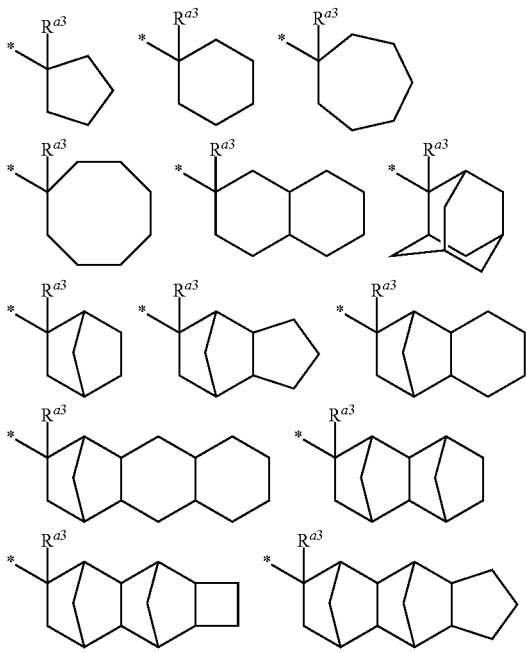

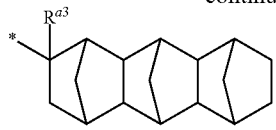

wherein $R^{a3}$ is the same as defined above and * represents a binding site.

The group represented by formula (1) wherein $R^{a1}$, $R^{a2}$ and $R^{a3}$ independently each represent a C1-C8 alkyl group such as a tert-butyl group, the group represented by formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferred.

For formula (2), examples of the hydrocarbon group include an alkyl group, an alicyclic hydrocarbon group, an aromatic hydrocarbon group and a group consisting of two or more of them.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

Examples of the divalent hydrocarbon group formed by bonding $R^{a2'}$ and $R^{a3'}$ each other include those formed by removing a hydrogen atom from the hydrocarbon group represented by $R^{a1'}$, $R^{a2'}$ and $R^{a3'}$.

It is preferred that at least one of $R^{a1'}$ and $R^{a2'}$ is a hydrogen atom.

Examples of the group represented by formula (2) include the following.

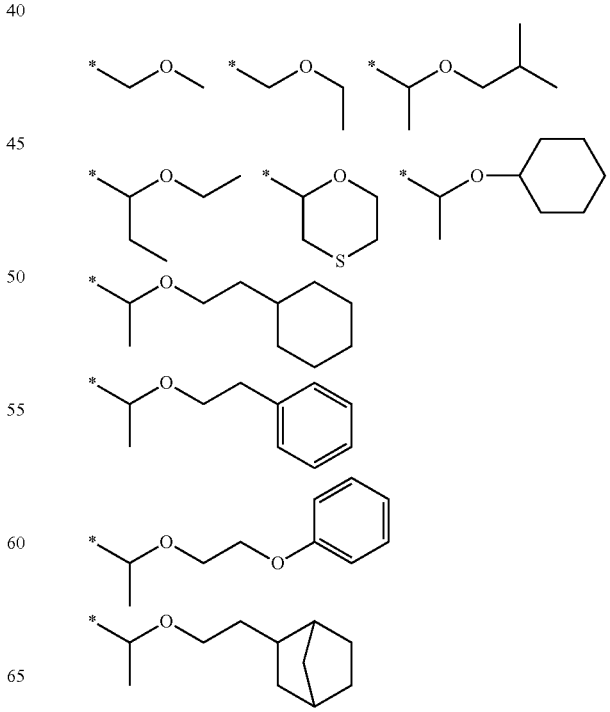

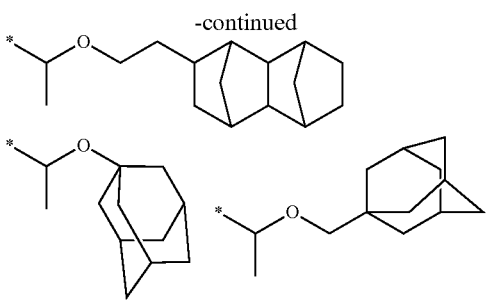

Monomer (a1) is preferably a monomer having an acid-labile group in its side chain and an ethylenic unsaturated group, more preferably a (meth)acrylate monomer having an acid-labile group in its side chain, and still more preferably a (meth)acrylate monomer having the group represented by formula (1) or (2).

The (meth)acrylate monomer having an acid-labile group in its side chain is preferably those which comprise a C5-C20 alicyclic hydrocarbon group. The resin which comprises a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2).

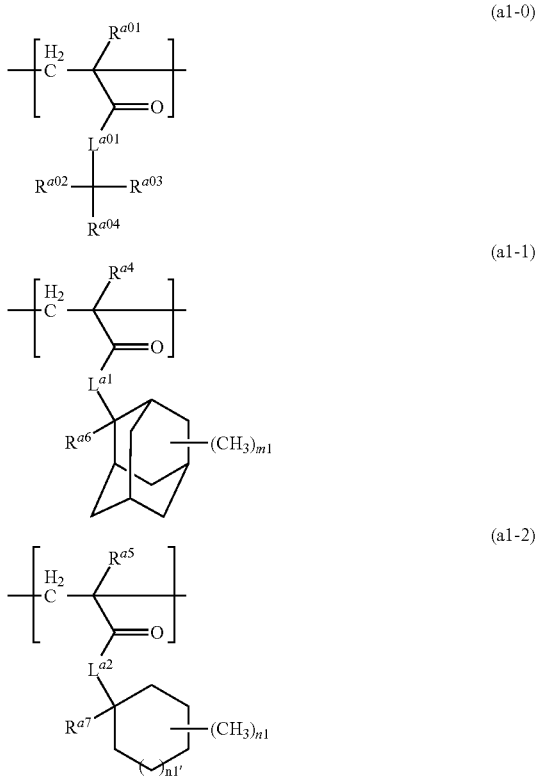

In each formula, $L^{a01}$, $L^{a1}$ and $L^{a2}$ each independently represent —O— or *—O—(CH$_2$)$_{k1}$—CO—O— in which k1 represents an integer of 1 to 7 and * represents a binding site to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C18 alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may comprise two or more of such structural units.

$L^{a01}$ is preferably *—O— or *—O—(CH$_2$)$_{f1}$—CO—O— in which * represents a binding site to —CO—, and f1 represents an integer of 1 to 4, and is more preferably *—O— or *—O—CH$_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group.

Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—(CH$_2$)$_{f1}$—CO—O— in which represents a binding site to —CO—, and f1 is the same as defined above, and is more preferably *—O— or *—O—CH$_2$—CO—O— and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following.

For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group.

The alicyclic hydrocarbon group represented by $R^{a6}$ and $R^{a7}$ is preferably a C3-C8 alicyclic hydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12), preferably those represented by formulae (a1-0-1) to (a1-0-10).
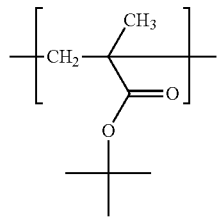
(a1-0-1)
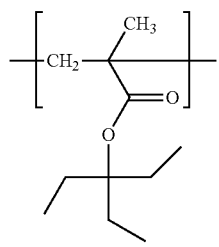
(a1-0-2)
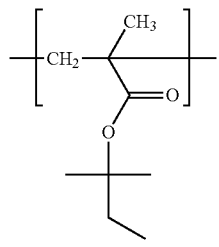
(a1-0-3)
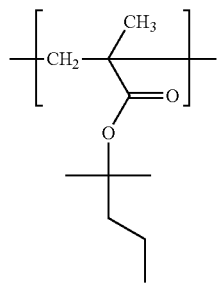
(a1-0-4)
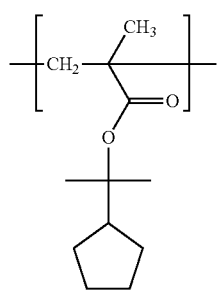
(a1-0-5)
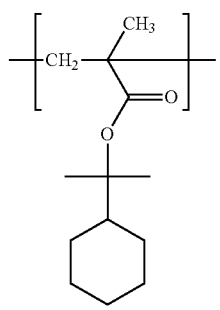
(a1-0-6)
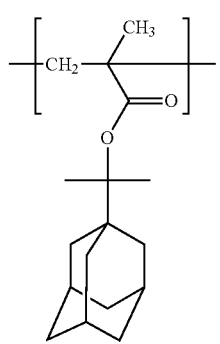
(a1-0-7)
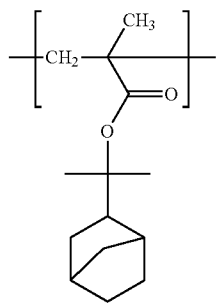
(a1-0-8)
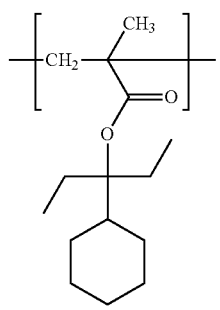
(a1-0-9)
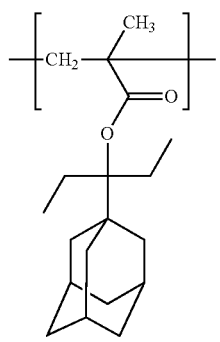
(a1-0-10)

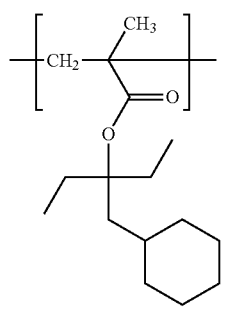
(a1-0-11)

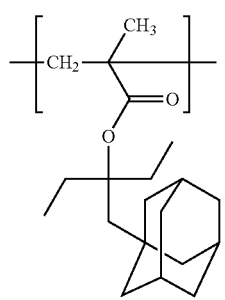
(a1-0-12)

Examples of the structural unit (a1-0) further include such groups that a methyl group has been replaced by a hydrogen atom in any one of formulae (a1-0-1) to (a1-0-12).

Examples of the monomer from which the structural unit (a1-1) is derived include the monomers described in JP2010-204646A1, and the following monomers represented by the formulae (a1-1-1) to (a1-1-8), preferably the following monomers represented by the formulae (a1-1-1) to (a1-1-4).

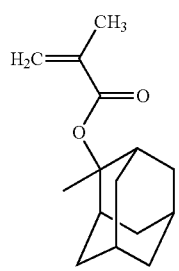
(a1-1-1)

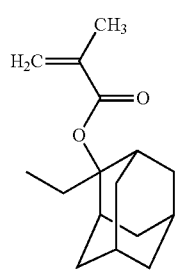
(a1-1-2)

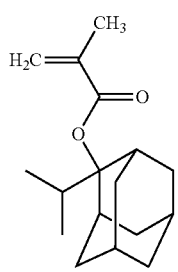
(a1-1-3)

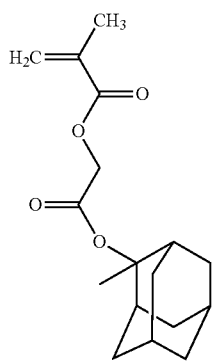
(a1-1-4)

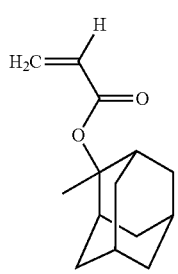
(a1-1-5)

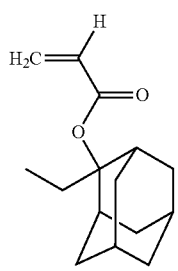
(a1-1-6)

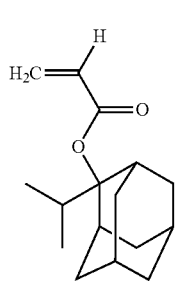
(a1-1-7)

(a1-1-8)

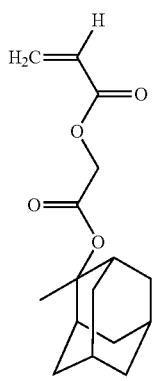

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by formulae (a1-2-1) to (a1-2-12), more preferably the monomers represented by formulae (a1-2-3), (a1-2-4), (a1-2-9) and (a1-2-10), still more preferably the monomers represented by formulae (a1-2-3) and (a1-2-9).

(a1-2-1)

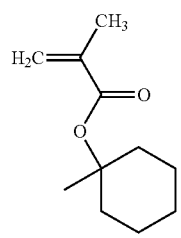

(a1-2-2)

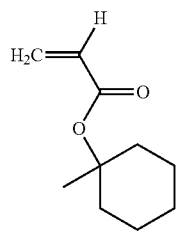

(a1-2-3)

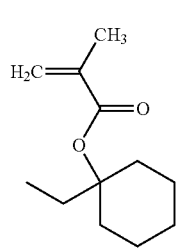

(a1-2-4)

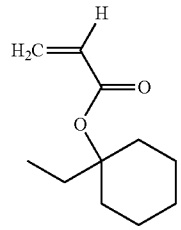

(a1-2-5)

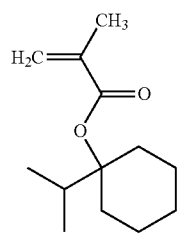

(a1-2-6)

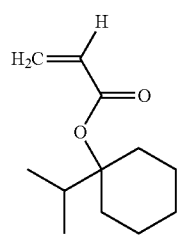

(a1-2-7)

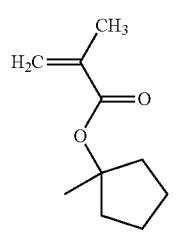

(a1-2-8)

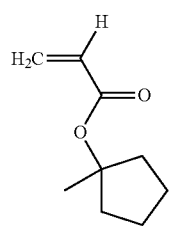

(a1-2-9)

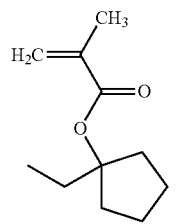

(a1-2-10)

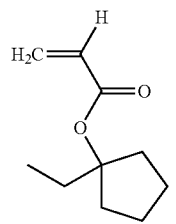

-continued

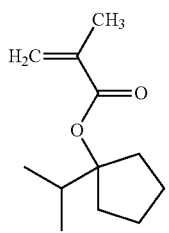

(a1-2-11)

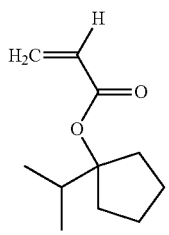

(a1-2-12)

The content of the structural unit having an acid-labile group in the resin is usually 10 to 95% by mole, preferably 15 to 90% by mole and more preferably 20 to 85% by mole based on 100% by mole of all the structural units of the resin. The content of the structural unit having an acid-labile group in the resin can be adjusted by adjusting the amount of the monomer having an acid-labile group based on the total amount of the monomers used for producing the resin.

When the resin comprises one or more of the structural units represented by formulae (a1-0), (a1-1) and (a1-2), the total content of the structural units is usually 10 to 95% by mole, preferably 15 to 90% by mole and more preferably 15 to 90% by mole and still more preferably 20 to 85% by mole based on 100% by mole of all the structural units of the resin.

Other examples of the structural unit (a1) having a group represented by formula (1) include a structural unit represented by formula (a1-3):

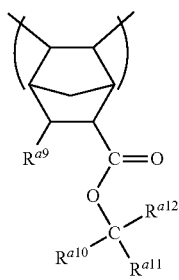

(a1-3)

wherein $R^{a9}$ represents a hydrogen atom, a carboxyl group, a cyano group, a C1-C3 aliphatic hydrocarbon group which can have a hydroxy group, or a group represented by —COOR$^{a13}$ group in which $R^{a13}$ represents a C1-C8 alkyl group or a C3-C20 alicyclic hydrocarbon group, and a group composed of a C1-C8 aliphatic hydrocarbon group and a C3-C20 alicyclic hydrocarbon group, and the aliphatic hydrocarbon group and the alicyclic hydrocarbon group can have a hydroxy group, and a methylene in the alkyl group and the alicyclic hydrocarbon group can be replaced by —O— or —CO—, $R^{a10}$, $R^{a11}$ and $R^{a12}$ each independently represent a C1-C12 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have a hydroxy group, and a methylene group in alkyl group and the alicyclic hydrocarbon group can be replaced by —O— or —CO—.

As $R^{a9}$, examples of the alkyl group which can have a hydroxy group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group, a propyl group.

Examples of the alicylic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group.

Examples of the alkyl group represented by $R^{a10}$, $R^{a11}$ and $R^{a12}$ include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group.

The alicylic hydrocarbon group represented by $R^{a10}$, $R^{a11}$ and $R^{a12}$, which may be a monocyclic or polycyclic group. Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group, a cycloheptyl group, a cyclodecyl group. Examples of the polycyclic alicyclic hydrocarbon group include a hydronaphthyl group, an adamantyl group, a 2-alkyladamantane-2-yl group, a 1-(adamantane-1-yl)alkane-1-yl group, a norbornyl group, a methylnorbornyl group, and an isobornyl group.

When the divalent hydrocarbon group is formed by bonding $R^{a10}$ and $R^{a11}$, examples of —C($R^{a10}$)($R^{a11}$)($R^{a12}$) include the following ones;

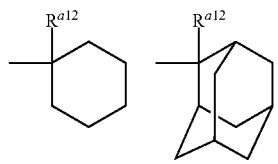

where $R^{a12}$ is as defined above.

Examples of the monomer from which the structural unit represented by formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit represented by formula (a1-3), the photoresist composition having excellent resolution and higher dry-etching resistance tends to be obtained.

When Resin (A) comprises the structural unit represented by formula (a1-3), the content of the structural unit is usually 10 to 95% by mole and preferably 15 to 90% by mole and more preferably 20 to 85% by mole based on total molar of all the structural units of the resin.

Other examples of the structural unit (a1) having a group represented by formula (2) include one represented by formula (a1-4):

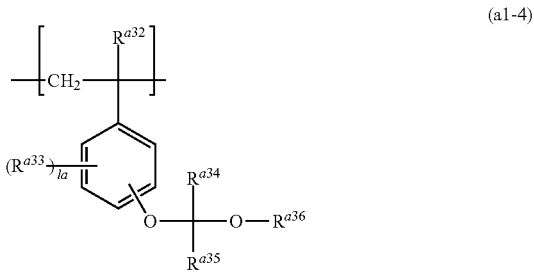

(a1-4)

wherein $R^{a32}$ represents a hydrogen atom, a halogen atom other than a fluorine atom, a C1-C6 alkyl group or a C1-C6 halogenated alkyl group, $R^{a33}$ is independently in each occurrence a halogen atom other than a fluorine atom, a hydroxy group, a C1-C6 alkyl group, a C1-C6 alkoxy group, a C2-C4 acyl group, a C2-C4 acyloxy group, an acryloyl group or a methacryloyl group, $l^a$ represents an integer of 0 to 4, $R^{a34}$ and $R^{a35}$ each independently represent a hydrogen atom or a C1-C12 hydrocarbon group, $R^{a36}$ represents a C1-C20 aliphatic hydrocarbon group in which a methylene group can be replaced by —O— or —S—, and $R^{a35}$ and $R^{a36}$ are bonded to each other to jointly represent a C2-C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1-C4 alkyl group, more preferably a methyl group and an ethyl group, and still more preferably a methyl group.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of halogen atom represented by $R^{a32}$ and $R^{a33}$ include a chlorine atom and a bromine atom.

Examples of the groups represented by $R^{a34}$ and $R^{a35}$ include those as referred to for $R^{a1'}$ and $R^{a2'}$.

Examples of the groups represented by $R^{a36}$ include those as referred to for $R^{a3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "la" preferably represents 0 or 1, more preferably 1.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1-C18 alkyl group, a C3-C18 monovalent alicyclic hydrocarbon group, a C6-C18 monovalent aromatic hydrocarbon group, and any combination of them, and preferably a C1-C18 alkyl group, a C3-C18 monovalent alicyclic hydrocarbon group and a C7-C18 aralkyl group. These groups may be unsubstituted or substituted. The alkyl group and the monovalent alicyclic hydrocarbon group are preferably unsubstituted. As the substituent for the monovalent aromatic hydrocarbon group, a C6-C10 aryloxy group is preferred.

Examples of the monomer from which the structural unit (a1-4) is derived include monomers recited in JP2010-204646A1. Among them, the monomers represented by formulae (a1-4-1), (a1-4-2), (a1-4-3), (a1-4-4), (a1-4-5), (a1-4-6) and (a1-4-7) are preferred, and the monomers represented by formulae (a1-4-1), (a1-4-2), (a1-4-3), (a1-4-4) and (a1-4-5) are more preferred.

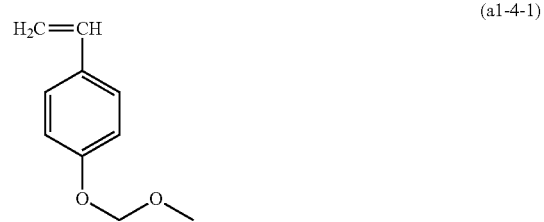

(a1-4-1)

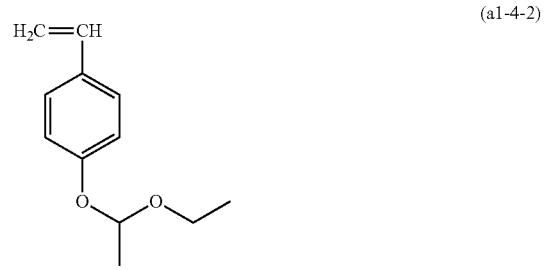

(a1-4-2)

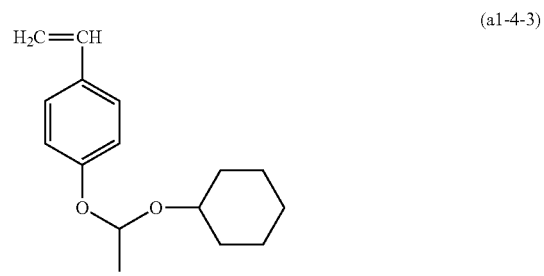

(a1-4-3)

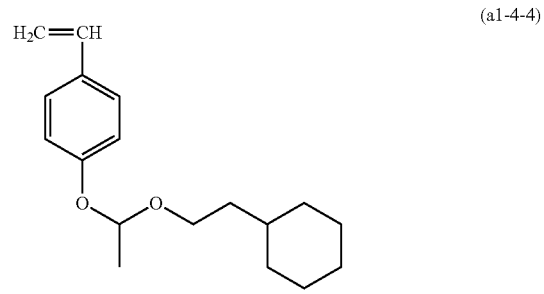

(a1-4-4)

-continued (a1-4-5)
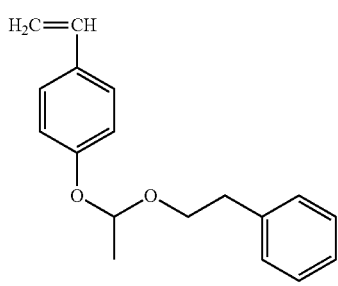

(a1-4-6)
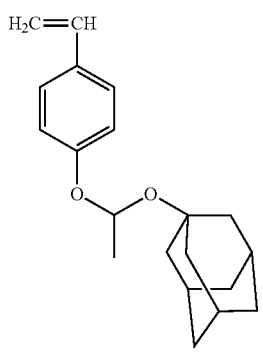

(a1-4-7)
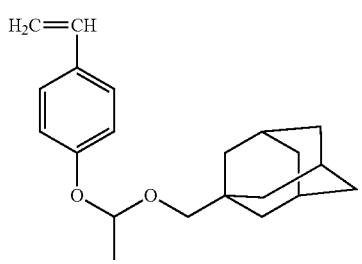

When Resin (A) comprises a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by formula (a1-5):

(a1-5)
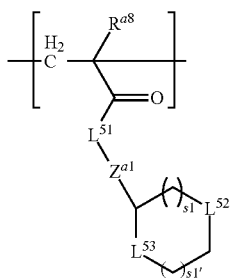

In formula (a1-5), $R^{a8}$ represents a hydrogen atom, a halogen atom other than a fluorine atom, or a C1-C6 alkyl group which can have a halogen atom other than a fluorine atom, $Z^{a1}$ represents a single bond or *—$(CH_2)_{k1}$—CO-$L^{54}$- in which k1 represents an integer of 1 to 4 and * represents a binding site to $L^{54}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a1-5) is sometimes referred to as "structural unit (a1-5)".

Examples of halogen atoms include a chlorine atom.

Examples of the alkyl group include a methyl group, an ethyl group, n-propyl group, an isopropyl group, n-butyl group, sec-butyl group, tert-butyl group, a pentyl group, a hexyl group, a heptyl group, a 2-ethylhexyl group, and an octyl group.

In the formula (a1-5), $R^{a8}$ preferably represents a hydrogen atom, or a methyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2. $Z^{a1}$ preferably represents a single bond or *—$CH_2$—CO—O— wherein * represents a binding site to $L^{51}$.

Examples of the monomer from which the structural unit (a1-5) is derived include one mentioned in JP2010-61117A1 and the following ones:

(a1-5-1)
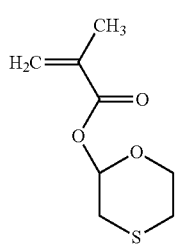

(a1-5-2)
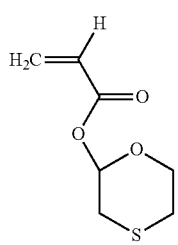

(a1-5-3)
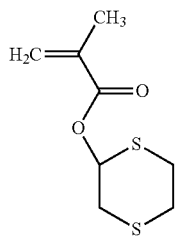

(a1-5-4)
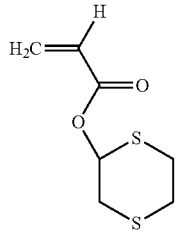

When Resin (A) comprises a structural unit (a1-5), its content is usually 1 to 50% by mole, preferably 3 to 45% by mole and more preferably 5 to 40% by mole based on 100% by mole of all the structural units of the resin.

Resin (A) comprises preferably one or more of the structural units (a1-0), (a1-1), (a1-2) and (a1-5), more preferably at least one of the structural units (a1-1), (a1-2) and (a1-5), still more preferably two or more of the structural units (a1-1), (a1-2) and (a1-5), and further more preferably the structural units (a1-1) and (a1-2) or the structural units (a1-1) and (a1-5).

Resin (A) comprises preferably the structural unit (a1-1).

The structural unit (s) is derived from a monomer having no acid-labile group.

As to the monomer having no acid-labile group, monomers which have been known to in the art can be used as such monomer, and they are not limited to any specific one provided that it has no acid-labile group.

The structural unit having no acid-labile group preferably has a hydroxy group or a lactone ring. When the resin comprises the structural unit derived from the monomer having no acid-labile group and having a hydroxy group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet is used as an exposure system, the resin which comprises the structural unit (a2) having a phenolic hydroxy group is preferred. When ArF excimer laser (wavelength: 193 nm) is used as an exposure system, the resin which comprises the structural unit (a2) having an alcoholic hydroxy group is preferred and the resin which comprises the structural unit (a2-1) described later is more preferred.

Resin (A) may comprise one or more of the structural units (a2).

Examples of the structural unit (a2) having a phenolic hydroxy group include one represented by formula (a2-0):

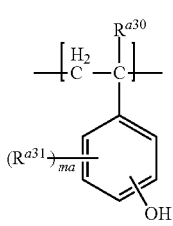

(a2-0)

In formula (a2-0), $R^{a30}$ represents a hydrogen atom, a halogen atom, or a C1-C6 alkyl group, $R^{a31}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred. Examples of the C2-C4 acyl group include an acetyl group, a propyonyl group and a butyryl group, and examples of the C2-C4 acyloxy group include an acetyloxy group, a propyonyloxy group and a butyryloxy group. In the formula (a2-0), ma is preferably 0, 1 or 2, and is more preferably 0 or 1, and especially preferably 0.

Among them, the structural units represented by formulae (a2-0-1), (a2-0-2), (a2-0-3) and (a2-0-4) are preferred as the structural unit (a2-0), and those represented by formulae (a2-0-1) and (a2-0-2) are more preferred.

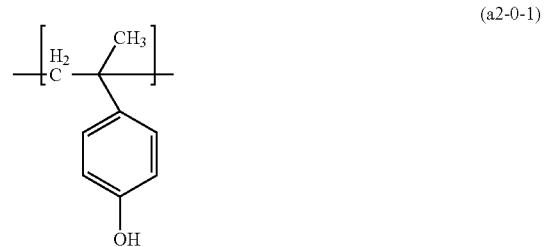

(a2-0-1)

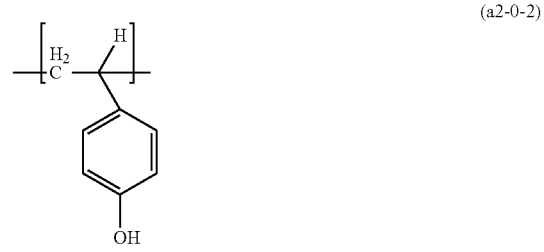

(a2-0-2)

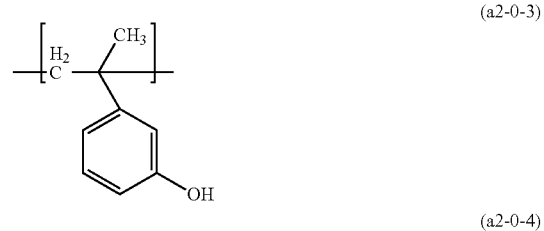

(a2-0-3)

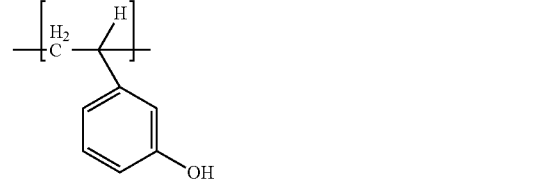

(a2-0-4)

Resin (A) which comprises a structural unit represented by formula (a2-0) can be produced, for example, by polymerizing a monomer where its phenolic hydroxy group has been protected with a suitable protecting group, followed by deprotection. Examples of the protecting group for a phenolic hydroxy group include an acetyl group.

When Resin (A) comprises the structural unit represented by formula (a2-0), its content is usually 5 to 95% by mole and preferably 10 to 80% by mole and more preferably 15 to 80% by mole based on total molar of all the structural units of the resin.

Examples of the structural unit (a2) having an alcoholic hydroxy group include one represented by formula (a2-1):

(a2-1)

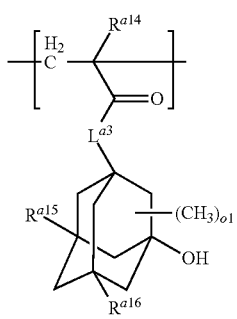

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding site to —CO—, and k2 represents an integer of 1 to 7, and o1 represents an integer of 0 to 10.

Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxy group. $L^{a3}$ is preferably *—O— or *—O—$(CH_2)_{f2}$—CO—O— in which * represents a binding site to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of monomers from which the structural unit (a2-1) is derived include compounds mentioned in JP2010-204646A.

Preferred examples of the structural unit (a2-1) include those represented by formulae (a2-1-1) to (a2-1-6).

(a2-1-1)

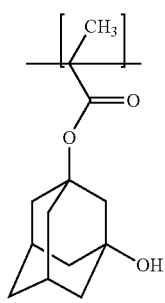

(a2-1-2)

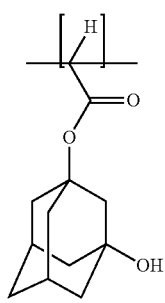

(a2-1-3)

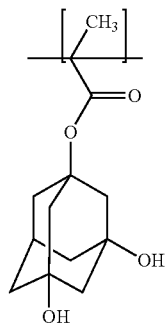

(a2-1-4)

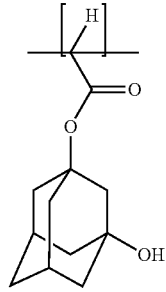

(a2-1-5)

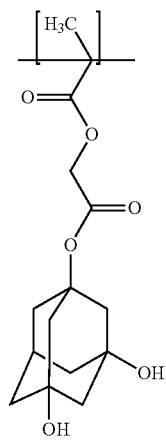

(a2-1-6)

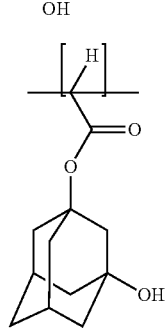

Among them, more preferred are the structural units represented by formulae (a2-1-1), (a2-1-2), (a2-1-3) and (a2-1-4), still more preferred are the structural units represented by formulae (a2-1-1) and (a2-1-3).

When Resin (A) comprises the structural unit (a2-1), its content is usually 1 to 45% by mole, preferably 1 to 40% by mole, and more preferably 1 to 35% by mole, and especially preferably 2 to 20% by mole, based on total molar of all the structural units of the resin.

Examples of the lactone ring of the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring, an adamantanelactone ring and a condensed lactone ring formed from γ-butyrolactone ring and the other ring.

Preferred examples of the structural unit (a3) include those represented by formulae (a3-1), (a3-2), (a3-3) and (a3-4):

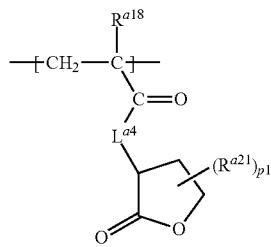

(a3-1)

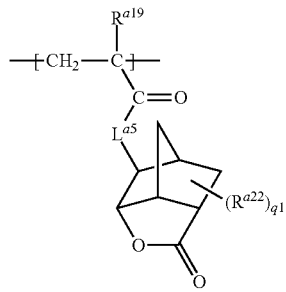

(a3-2)

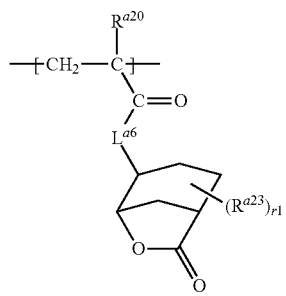

(a3-3)

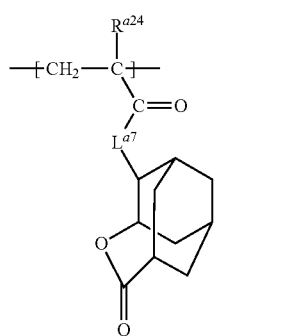

(a3-4)

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 monovalent aliphatic hydrocarbon group, $R^{a22}$ and $R^{a23}$ are independently in each occurrence a carboxyl group, a cyano group or a C1-C4 monovalent aliphatic hydrocarbon group, $R^{a24}$ each independently represent a hydrogen atom, a halogen atom other than a fluorine atom, or a C1-C6 alkyl group which can have a halogen atom other than a fluorine atom, $L^{a7}$ represents a single bond, $*^1$-$L^{a8}$-O—, $*^1$-$L^{a8}$-CO—O—, $*^1$-$L^{a8}$-CO—O-$L^{a9}$-CO—O— or $*^1$-$L^{a8}$-CO—O-$L^{a9}$-O— or in which $L^{a8}$ and $L^{a9}$ each independently represent C1-C6 divalent alkanediyl group, $*^1$ represents a binding site to —O—, and p1 represents an integer of 0 to 5, q1 and r1 independently each represent an integer of 0 to 3.

Examples of halogen atom represented by $R^{a24}$ include a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group which has an halogen atom include a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that $L^{a4}$, $L^{a5}$ and $L^{a6}$ each independently represent *—O— or *—O—$(CH_2)_{d1}$—CO—O— in which * represents a binding site to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or $*^1$-$L^{a8}$-CO—O—, more preferably a single bond, $*^1$—$CH_2$—CO—O— or $*^1$—$C_2H_4$—CO—O—.

Examples of the structural unit (a3) include the following ones.

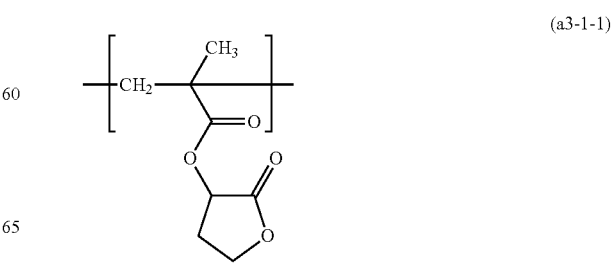

(a3-1-1)

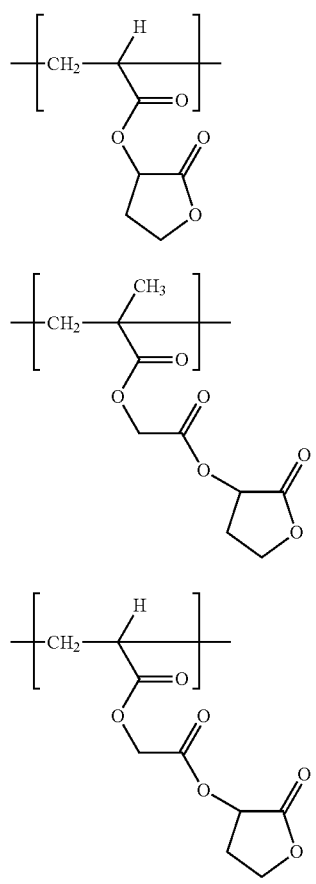
(a3-1-2)
(a3-1-3)
(a3-1-4)
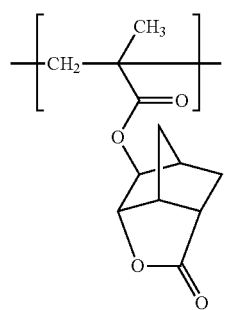
(a3-2-1)
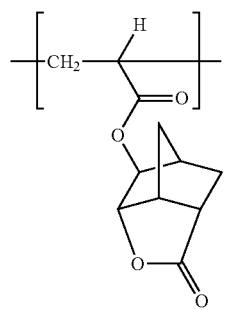
(a3-2-2)
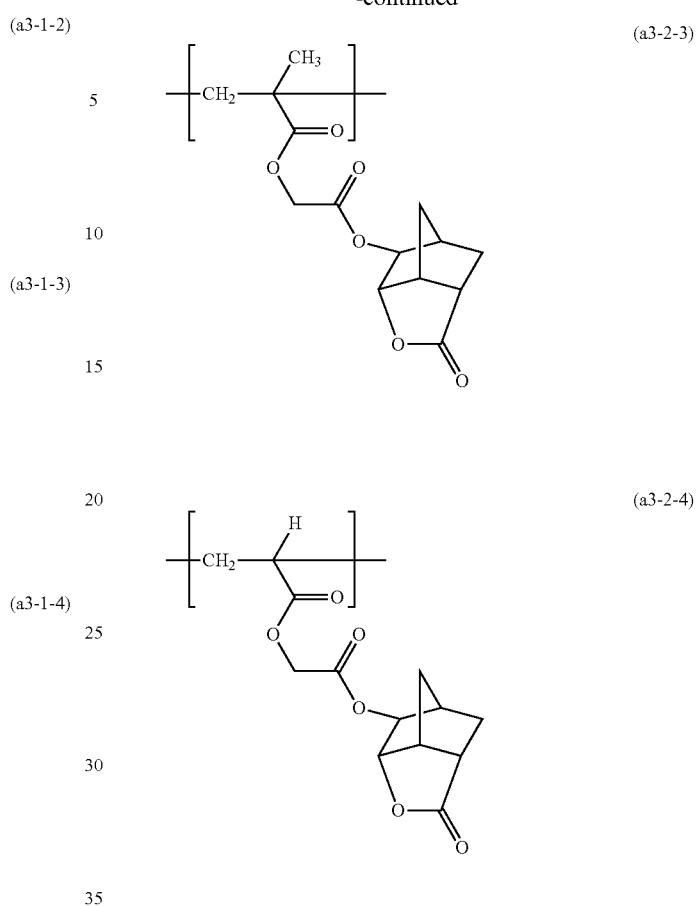
(a3-2-3)
(a3-2-4)
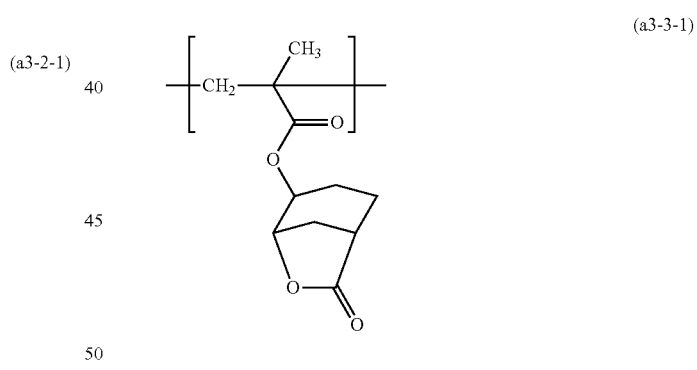
(a3-3-1)
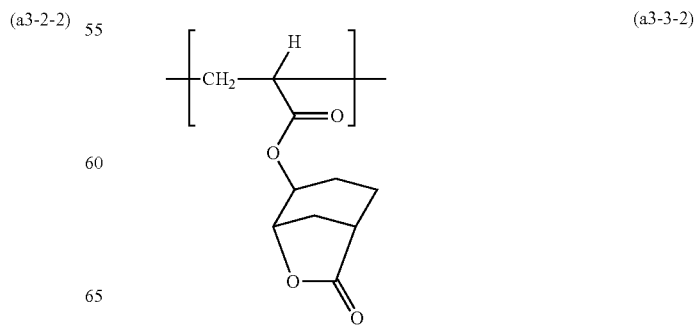
(a3-3-2)

(a3-3-3)
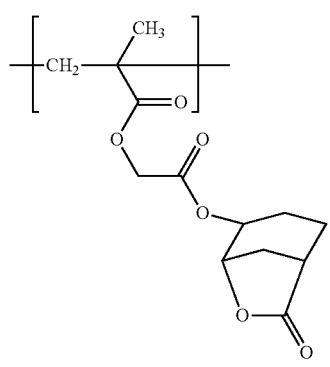
(a3-3-4)
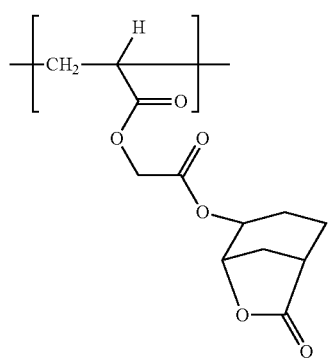
(a3-4-1)
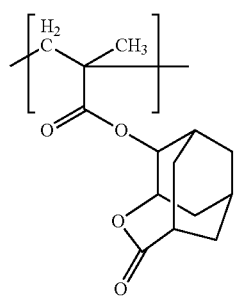
(a3-4-2)
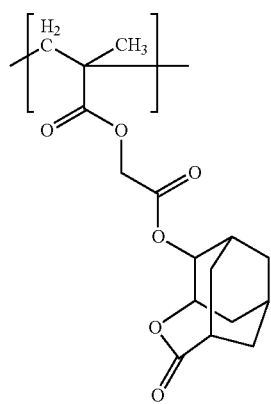
(a3-4-3)
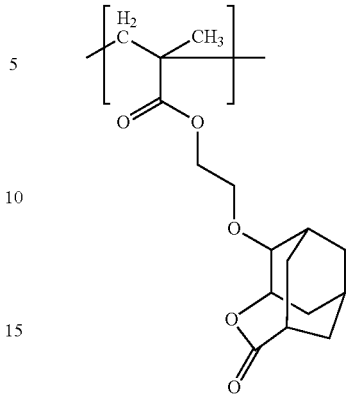
(a3-4-4)
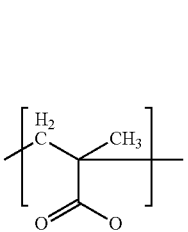
(a3-4-5)
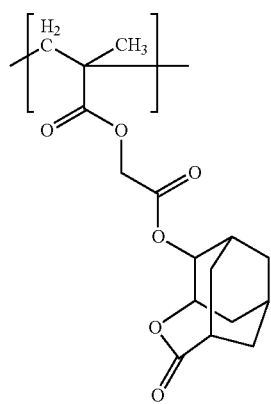

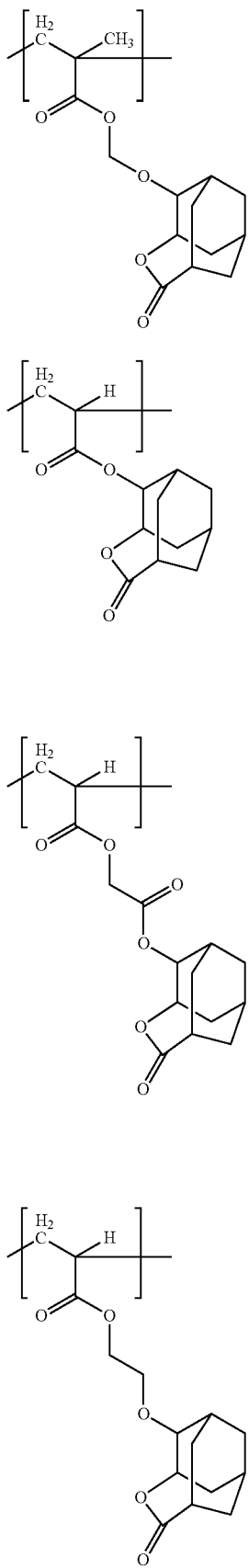
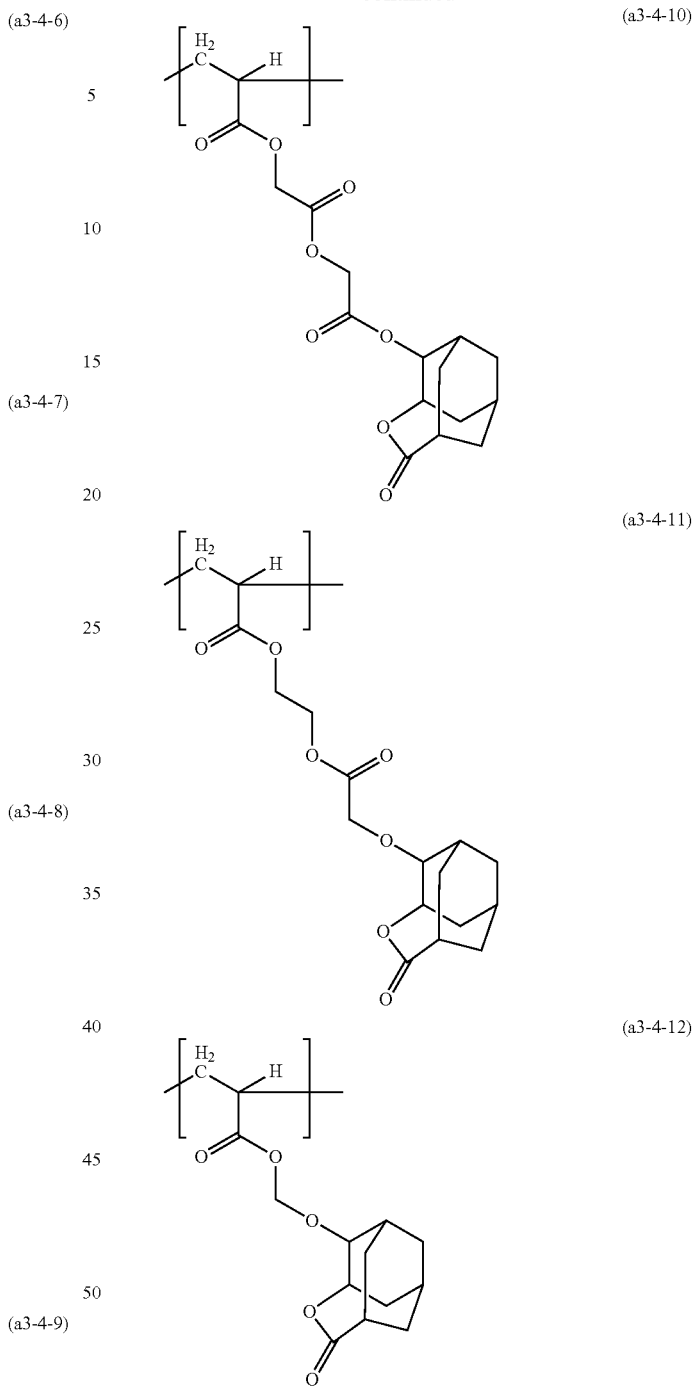

The structural unit (a3) is preferably one of formulae (a3-1-1) to (a3-1-4), formulae (a3-2-1) to (a3-2-4), formulae (a3-3-1) to (a3-3-4) and formulae (a3-4-1) to (a3-4-6), more preferably one of formulae (a3-1-1), formula (a3-1-2), formulae (a3-2-3) to (a3-2-4) and formulae (a3-4-1) to (a3-4-2), and still more preferably one of formulae (a3-1-1), (a3-2-3) and (a3-4-2).

Examples of the monomer from which the structural unit (a3) is derived include those mentioned in US2010/203446A1, US2002/098441A1 and US2013/143157A1.

When Resin (A) comprises the structural unit (a3), its content thereof is preferably 5 to 70% by mole, and more preferably 10 to 65% by mole and more preferably 10 to 60% by mole, based on total molar of all the structural units of the resin.

Examples of another structural unit having no acid-labile group include a structural unit having a halogen atom and a structural unit which has a hydrocarbon not being removed therefrom by action of an acid.

Examples of the structural unit having a halogen atom include the following one.

Hereinafter, the structural unit having no acid-labile group but having a halogen atom is referred to as "structural unit (a4)". Halogen atoms for the structural unit (a4) may be a fluorine atom, a chlorine atom, a bromine atom, or an iodine atom. The structural unit (a4) has preferably a fluorine atom.

Examples of the structural unit (a4) include one represented by formula (a4-0):

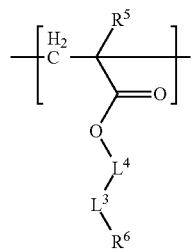

(a4-0)

wherein $R^5$ represents a hydrogen atom or a methyl group;
$L^4$ represents a single bond or a C1-C4 aliphatic saturated hydrocarbon group, preferably a C1-C4 aliphatic saturated hydrocarbon group;
$L^3$ represents a C1-C8 perfluoroalkanediyl group or a C3-C12 alicyclic perfluorohydrocarbon group; and
$R^6$ represents a hydrogen atom or a fluorine atom.

Examples of the perfluoroalkanediyl group for $L^3$ include a difluoromethylene group, a perfluoroethylene group, a (perfluoroethyl)fluoromethylene group, a perfluoropropane-1,3-diyl group, a perfluoropropane-1,2-diyl group, a perfluorobutane-1,4-diyl group, a perfluoropentane-1,5-diyl group, a perfluorohexane-1,6-diyl group, a perfluoroheptane-1,7-diyl group, and a perfluorooctane-1,8-diyl group.

Examples of the alicyclic perfluorohydrocarbon group for $L^3$ include a perfluoroadamantandiyl group.

$L^4$ is preferably a methylene group or an ethylene group, more preferably a methylene group.

$L^3$ is preferably a C1-C6 perfluoroalkanediyl group, more preferably a C1-C3 perfluoroalkanediyl group.

Examples of the structural unit represented by formula (a4-0) include the following ones and those in which a methyl group has been replaced by a hydrogen atom in each of the following formulae.

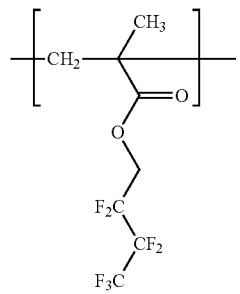

(a4-0-1)

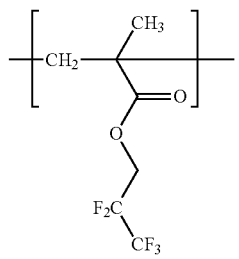

(a4-0-2)

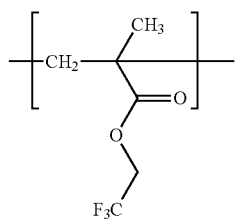

(a4-0-3)

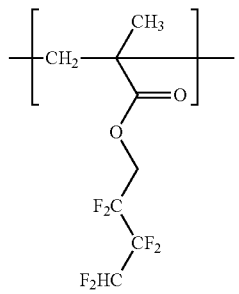

(a4-0-4)

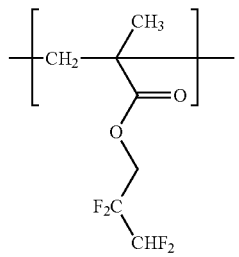

(a4-0-5)

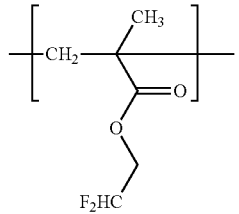

(a4-0-6)

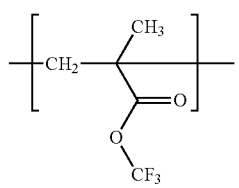

(a4-0-7)

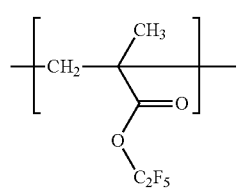
(a4-0-8)
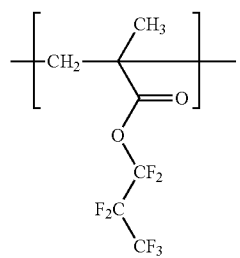
(a4-0-9)
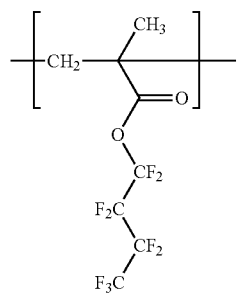
(a4-0-10)
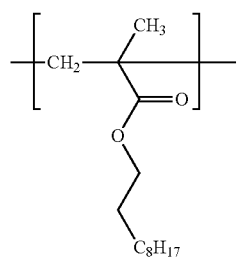
(a4-0-11)
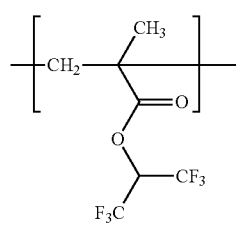
(a4-0-12)
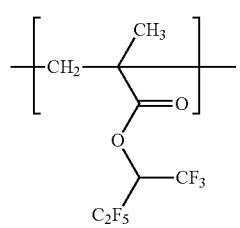
(a4-0-13)
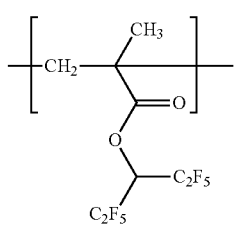
(a4-0-14)
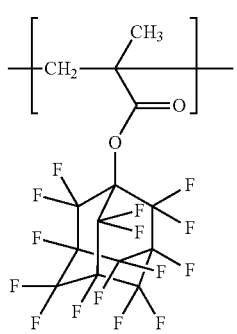
(a4-0-15)
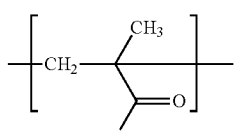
(a4-0-16)
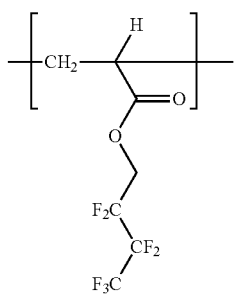
(a4-0-17)
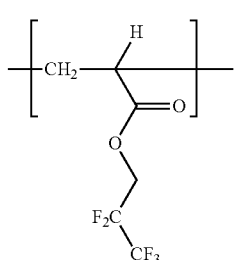
(a4-0-18)
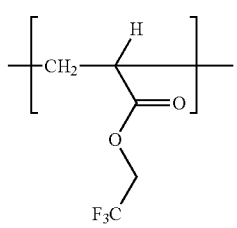
(a4-0-19)

(a4-0-20)
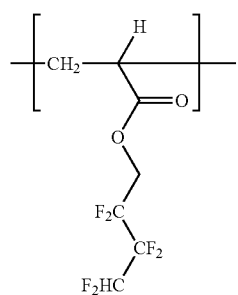
(a4-0-21)
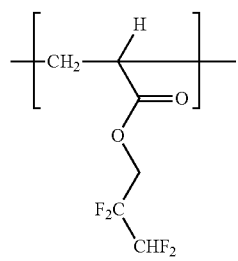
(a4-0-22)
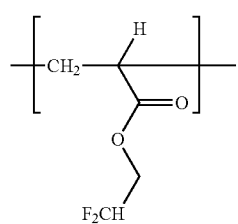
(a4-0-23)
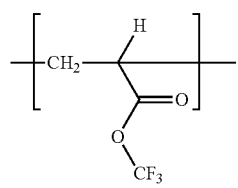
(a4-0-24)
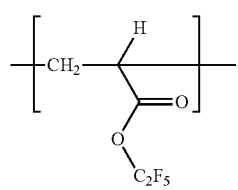
(a4-0-25)
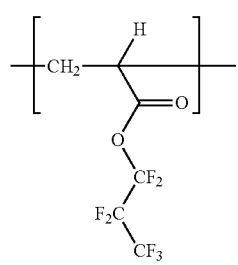
(a4-0-26)
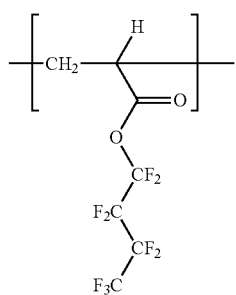
(a4-0-27)
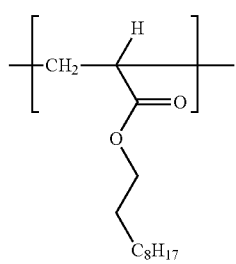
(a4-0-28)
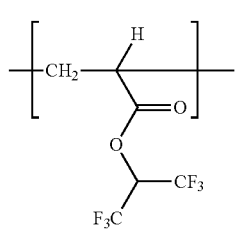
(a4-0-29)
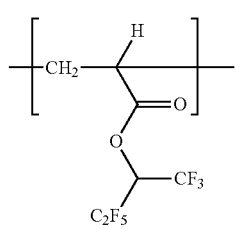
(a4-0-30)
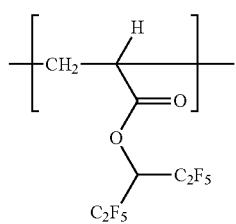
(a4-0-31)
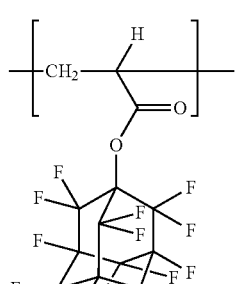

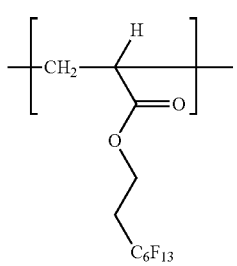

(a4-0-32)

Examples of the structural unit (a4) include one represented by formula (a4-1):

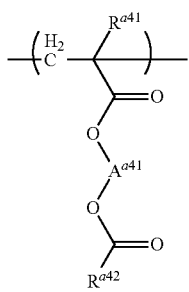

(a4-1)

wherein $R^{a41}$ represents a hydrogen atom or a methyl group;

$A^{a41}$ represents a C1-C6 divalent alkanediyl group which can have a substituent or a moiety represented by formula (a-g1):

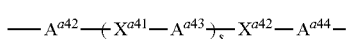

(a-g1)

in which s represents an integer of 0 to 1, $A^{a42}$ and $A^{a44}$ respectively represent a C1-C5 divalent hydrocarbon group which can have a substituent, $A^{a43}$ represents a single bond or a C1-C5 divalent hydrocarbon group which can have a substituent, $X^{a41}$ and $X^{a42}$ respectively represent —O—, —CO—, —CO—O—, or —O—CO—, provided that the sum of carbon atoms of $A^{a42}$, $A^{a43}$, $A^{a44}$, $X^{a41}$ and $X^{a42}$ is 6 or less;

$R^{a42}$ represents a C1-C20 monovalent hydrocarbon group which can have a substituent, provided that each or both of $A^{a41}$ and $R^{a42}$ have a halogen atom; and $A^{a44}$ is bonded to —O—CO—$R^{a42}$.

Examples of halogen atom for formula (a4-1) include a fluorine atom, a chlorine atom, a bromine atom and an iodine atom.

The divalent hydrocarbon group is preferably a divalent saturated hydrocarbon group while it can have a carbon-carbon double bond.

Examples of the divalent saturated hydrocarbon group include alkanediyl groups which may be a linear or branched one, divalent alicyclic hydrocarbon groups, and combination of them.

Examples of the monovalent hydrocarbon group for $R^{a42}$ include monovalent chain or cyclic saturated hydrocarbon groups, a monovalent aromatic hydrocarbon group, and combination of them.

Examples of monovalent chain hydrocarbon group include a methyl group, an ethyl group, a propyl group, a butyl group, a pentyl group, a hexyl group, a heptyl group, an octyl group, a decyl group, a dodecyl group, a hexadecyl group, a pentadecyl group, a hexyldecyl group, heptadecyl group and an octadecyl group.

Examples of monovalent cyclic hydrocarbons include cycloalkyl groups such as a cyclopentyl group, a cyclohexyl group, a cycloheptyl group and a cyclooctyl group; and monovalent polycyclic hydrocarbon groups such as a decahyrdonaphthyl group, an adamantyl group, a norbornyl group, and the following groups where * represents a binding site.

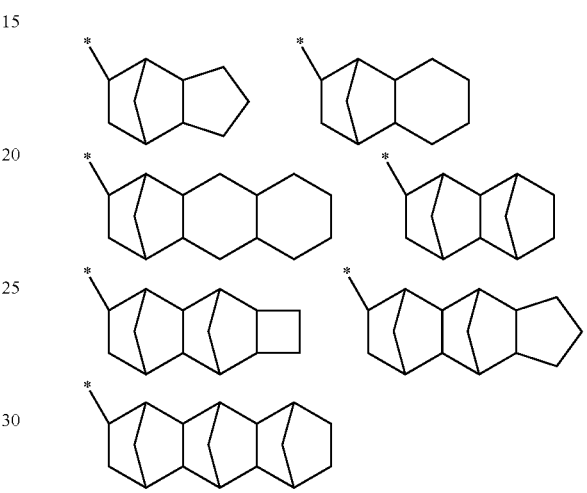

Examples of monovalent aromatic hydrocarbon groups include a phenyl group, a naphthyl group, an anthryl group, a biphenylyl group, a phenanthryl group and a fluorenyl group.

The monovalent hydrocarbon group for $R^{a42}$ is preferably monovalent chain and cyclic hydrocarbon groups and combination of them, which can have a carbon-carbon double bond, and more preferably a monovalent chain hydrocarbon group and cyclic hydrocarbon group and combination of them.

$R^{a42}$ is preferably a monovalent aliphatic hydrocarbon group which has a substituent, more preferably a monovalent aliphatic hydrocarbon group which has a halogen atom and/or a group represented by formula (a-g3).

(a-g3)

in which $X^{a43}$ represents an oxygen atom, a carbonyl group, a carbonyloxy group or an oxycarbonyl group, $A^{a45}$ represents a C3-C17 monovalent saturated hydrocarbon group which can have a fluorine atom.

When $R^{a42}$ is a monovalent saturated hydrocarbon group which has a group represented by formula (a-g3), $R^{a42}$ has preferably 15 or less carbon atoms, more preferably 12 or less carbon atoms in total including the carbon atoms of formula (a-g3). If $R^{a42}$ has a group represented by formula (a-g3), the number of the group is preferably 1.

The monovalent saturated hydrocarbon group which has a group represented by formula (a-g3) is preferably a compound represented by formula (a-g2):

(a-g2)

in which $A^{a46}$ represents a C3-C17 divalent saturated hydrocarbon group which can have a fluorine atom, $X^{a44}$ represents a carbonyloxy group or an oxycarbonyl group, and $A^{a47}$ represents a C3-C17 divalent saturated hydrocarbon group which can have a fluorine atom, provided that $A^{a46}$, $A^{a47}$ and $X^{a44}$ have 18 or less of carbon atoms in total and one or both of $A^{a46}$ and $A^{a47}$ have a fluorine atom.

The halogen-containing saturated hydrocarbon group represented by $R^{a42}$ is preferably a monovalent fluorine-containing saturated hydrocarbon group, more preferably a perfluoroalkyl group or a perfluorocycloalkyl group, still more preferably a C1-C6 perfluoroalkyl group, and further more preferably a C1-C3 perfluoroalkyl group.

Examples of perfluoroalkyl group include a perfluoromethyl group, a perfluoroethyl group, a perfluoropropyl group, a perfluorobutyl group, a perfluoropentyl group, a perfluorohexyl group, a perfluoroheptyl group, and a perfluorooctyl group. Examples of the perfluorocycloalkyl group include perfluorocyclohexyl group.

The divalent saturated hydrocarbon group represented by $A^{a46}$ has preferably 1 to 6, more preferably 1 to 3 carbon atoms.

The monovalent saturated hydrocarbon group represented by $A^{a47}$ has preferably 4 to 15, more preferably 5 to 12 carbon atoms. $A^{a47}$ is more preferably a cyclohexyl group or an adamantyl group.

Examples of the moiety represented by $-A^{a46}-X^{a44}-A^{a47}$ include the following ones.

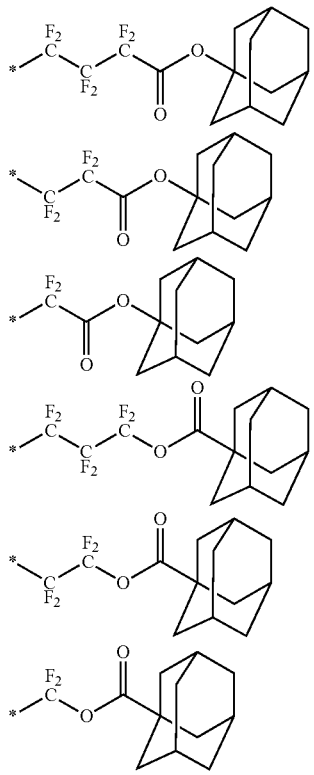

In each formula, * represents a binding site to a carbonyl group.

Examples of $A^{a41}$ typically include a C1-C6 alkanediyl group which may be a linear chain or branched chain. Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,2-diyl group, a butane-1,3-diyl group, a 1-methylbutane-1,2-diyl group, or a 2-methylbutane-1,4-diyl group. Examples of the substituents which such alkanediyl group can have include a hydroxy group or a C1-C6 alkoxy group.

$A^{a41}$ is preferably a C1-C4 alkanediyl group, more preferably a C2-C4 alkanediyl group, and still more preferably an ethylene group.

Examples of the alkanediyl group represented by $A^{a42}$, $A^{a43}$ and $A^{a44}$ include a methylene group, an ethylene group, a propane-1,3-diyl group, a butane-1,4-diyl group, a 2-methylpropane-1,3-diyl group, or a 2-methylbutane-1,4-diyl group. Examples of the substituents which such alkanediyl group can have include a hydroxy group or a C1-C6 alkoxy group.

$X^{a42}$ represents —O—, —CO—, —CO—O—, or —O—CO—.

Examples of the moiety represented by formula (a-g1) where $X^{a42}$ is an oxygen atom, a carbonyl group, a carbonyloxy group or an oxycarbonyl group include the following ones:

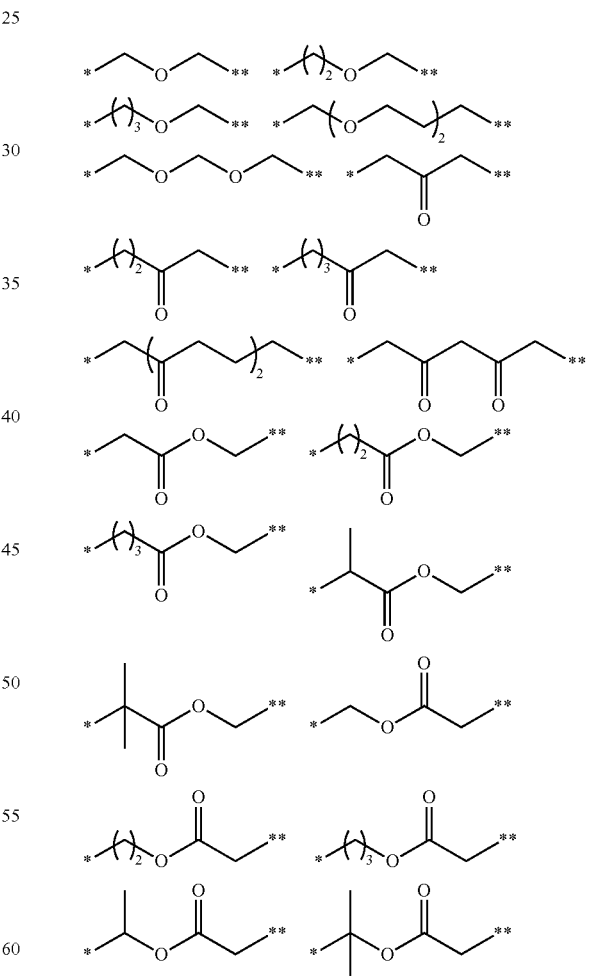

in which * and  represent binding sites, and  represents a binding site to —O—CO—$R^{a42}$.

The structural unit represented by formula (a4-1) is preferably one represented by formula (a4-2) or (a4-3).

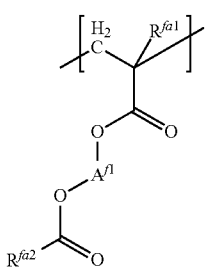

(a4-2)

In formula, $R^{fa1}$ represents a hydrogen atom or a methyl group.

$A^{f1}$ represents a C1-C6 alkanediyl group.

$R^{fa2}$ represents a C1-C10 monovalent hydrocarbon group having a fluorine atom.

The alkanediyl groups represented by $A^{f1}$ may be a linear chain or branched chain. Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,3-diyl group, a butane-1,3-diyl group, a 1-methylbutane-1,2-diyl group, or a 2-methylbutane-1,4-diyl group. Examples of the substituents which such alkanediyl group can have include a hydroxy group or a C1-C6 alkoxy group.

The monovalent hydrocarbon group represented by $R^{f2}$ includes monovalent saturated hydrocarbon groups and monovalent aromatic hydrocarbon groups. The monovalent saturated hydrocarbon groups may be a chain or cyclic saturated hydrocarbon group, or a combined group of them.

The monovalent saturated hydrocarbon groups are preferably an alkyl group or a monovalent alicyclic hydrocarbon group.

Examples of the alkyl group include a methyl group, an ethyl group, n-propyl group, isopropyl group, n-butyl group, sec-butyl group, a tert-butyl group, a pentyl group, a hexyl group and 2-ethylhexyl group.

The monovalent alicyclic hydrocarbon groups may be monocyclic or polycyclic groups. Examples of monovalent monocyclic hydrocarbon groups include a cyclopropyl group, a cyclobutyl group, a cyclopentyl group, a cyclohexyl group, a methylcyclohexyl group, a dimethylcyclohexyl group, a cycloheptyl group, a cyclooctyl group, a cycloheptyl group and a cyclodecyl group.

Examples of monovalent polycyclic hydrocarbon groups include a decahydronaphthyl group, an adamantyl group, a norbornyl group, and an isobornyl group.

Examples of the combined group of the above-mentioned hydrocarbon group include a 2-alkyladamantane-2-yl group, a 1-(adamantane-1-yl)alkane-1-yl group, and a methylnorbornyl group.

Examples of monovalent hydrocarbon groups having a fluorine atom for $R^{f2}$ include monovalent fluoroalkyl groups and monovalent fluorine atom-containing alicyclic hydrocarbon groups.

Specific examples of monovalent fluoroalkyl groups include a fluoromethyl group, a trifluoromethyl group, 1,1-difluoroethyl group, 2,2-difluoroethyl group, 2,2,2-trifluoroethyl group, perfluoroethyl group, 1,1,2,2-tetrafluoropropyl group, 1,1,2,2,3,3-hexafluoropropyl group, perfluoroethylmethyl group, 1-(trifluoromethyl)-1,2,2,2-tetrafluoroethyl group, perfluoropropyl group, 1,1,2,2-tetrafluorobutyl group, 1,1,2,2,3,3-hexafluorobutyl group, 1,1,2,2,3,3,4,4-octafluorobutyl group, perfluorobutyl group, 1,1-bis(trifluoro)methyl-2,2,2-trifluoroethyl group, 2-(perfluoropropyl)ethyl group, 1,1,2,2,3,3,4,4-octafluoropentyl group, perfluoropentyl group, 1,1,2,2,3,3,4,4,5,5-decafluoropentyl group, 1,1-bis(trifluoromethyl)-2,2,3,3,3-pentafluoropropyl group, 2-(perfluorobutyl)ethyl group, 1,1,2,2,3,3,4,4,5,5-decafluorohexyl group, 1,1,2,2,3,3,4,4,5,5,6,6-dodecafluorohexyl group, a perfluoropentylmethyl group and a perfluorohexyl group.

Specific examples of monovalent fluorine-containing alicyclic hydrocarbon groups include fluorocycloalkyl groups such as a perfluorocyclohexyl group and a perfluoroadamantyl group.

In formula (a4-2), $A^{f1}$ is preferably a C2-C4 alkylene group, and more preferably an ethylene group. $R^{fa2}$ is preferably a C1-C6 fluoroalkyl group.

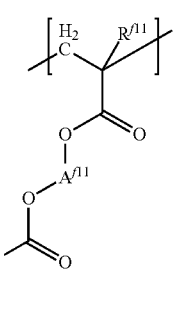

(a4-3)

In formula, $R^{f11}$ represents a hydrogen atom or a methyl group.

$A^{f11}$ represents a C1-C6 alkanediyl group.

$A^{f13}$ represents a C1-C18 divalent saturated hydrocarbon group which can have a fluorine atom.

$X^{f12}$ represents a carbonyloxy group or an oxycarbonyl group.

$A^{f14}$ represents a C1-C17 divalent saturated hydrocarbon group which can have a fluorine atom, provided that one or both of $A^{f13}$ and $A^{f14}$ represents a fluorine-containing saturated hydrocarbon group.

Examples of the alkanediyl group represented by $A^{f11}$ include those as referred to for $A^{f12}$.

As to $A^{f13}$, the divalent saturated hydrocarbon group includes chain saturated hydrocarbon groups, cyclic saturated hydrocarbon groups and combined groups of these groups.

As to $A^{f13}$, the divalent saturated hydrocarbon group which can have a fluorine atom is preferably a divalent saturated chain hydrocarbon group which can have a fluorine atom, more preferably a perfluoroalkanediyl group.

Examples of the divalent aliphatic hydrocarbon group which can have a fluorine atom include an alkanediyl group such as a methyl group, an ethylene group, a propanediyl group, a butanediyl group and pentanediyl group; and a perfluoroalkanediyl group such as a difluoromethylene group, a perfluoroethylene group, a perfluoropropanediyl group, a perfluorobutanediyl group and perfluoropentanediyl group.

The divalent cyclic hydrocarbon group which can have a fluorine atom may be a divalent monocyclic or polycyclic group.

Examples of the divalent monocyclic hydrocarbon group which can have a fluorine atom include a cyclohexanediyl group and a perfluorocyclohexanediyl group.

Examples of the divalent polycyclic hydrocarbon group which can have a fluorine atom include an adamantanediyl group, norbornanediyl group, and a perfluoroadamantanediyl group.

In the group represented by $A^{f14}$, the monovalent saturated hydrocarbon group includes chain saturated hydrocarbon groups, cyclic saturated hydrocarbon groups and combined groups of these saturated hydrocarbon groups.

As to $A^{f14}$, the monovalent aliphatic hydrocarbon group which can have a fluorine atom is preferably a monovalent saturated aliphatic hydrocarbon group which can have a fluorine atom, more preferably a perfluoroalkanediyl group.

Examples of the monovalent aliphatic hydrocarbon group which can have a fluorine atom include a trifluoromethyl group, a fluoromethyl group, a methyl group, a perfluoroethyl group, a 1,1,1-trifluoroethyl group, a 1,1,2,2-tetrafluoroethyl group, an ethyl group, a perfluoropropyl group, a 1,1,1,2,2-pentafluoropropyl group, propyl group, a perfluorobutyl group, 1,1,2,2,3,3,4,4-octafluorobutyl group, a butyl group, a perfluoropentyl group, 1,1,1,2,2,3,3,4,4-nonafluoropentyl group, a pentyl group, a hexyl group, a perfluorohexyl group, a heptyl group, a perfluoroheptyl group, an octyl group and a perfluorooctyl group.

The monovalent cyclic hydrocarbon group which can have a fluorine atom may be monocyclic or polycyclic monovalent group.

Examples of the monovalent monocyclic cyclic hydrocarbon group which can have a fluorine atom include a cyclopropyl group, cyclopentyl group, cyclohexyl group, and perfluorocyclohexyl group.

Examples of the monovalent polycyclic hydrocarbon group which can have a fluorine atom include an adamantyl group, a norbornyl group, and a perfluoroadamantyl group.

Examples of the combined groups of the above-mentioned aliphatic hydrocarbon group include a cyclopropylmethyl group, a cyclobutylmethyl group, an adamantylmethyl group, a norbornylmethyl group and a perfluoroadamantylmethyl group.

In formula (a4-3), $A^{f11}$ is preferably an ethylene group.

The divalent aliphatic hydrocarbon group represented by $A^{f13}$ has preferably 6 or less, more preferably 2 to 3, of carbon atoms.

The monovalent aliphatic hydrocarbon group represented by $A^{f14}$ has preferably 3 to 12, more preferably 3 to 10, of carbon atoms.

$A^{f14}$ has preferably a C3-C12 monovalent alicyclic hydrocarbon group, more preferably a cyclopropylmethyl group, a cyclopentyl group, a cyclohexyl group, a norbornyl group or an adamantyl group.

Examples of the structural unit of formula (a4-2) include preferably those represented by formulae (a4-1-1) to (a4-1-22).

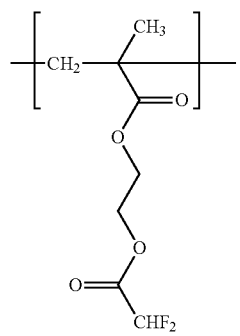
(a4-1-1)

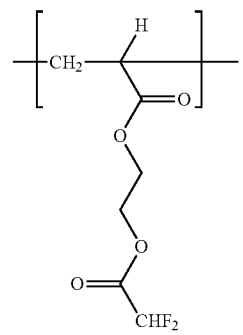
(a4-1-2)

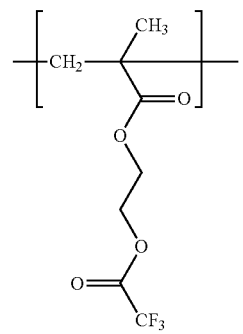
(a4-1-3)

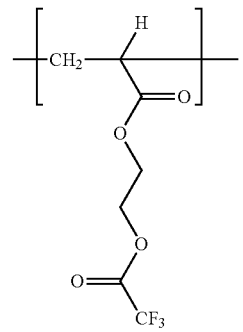
(a4-1-4)

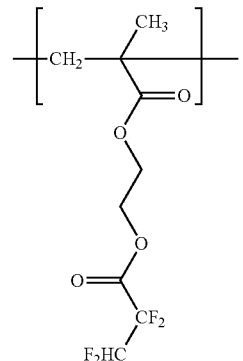
(a4-1-5)

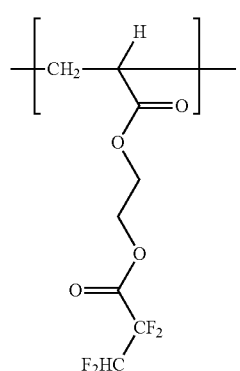
(a4-1-6)
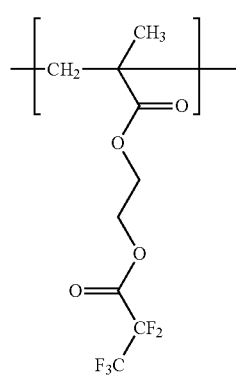
(a4-1-7)
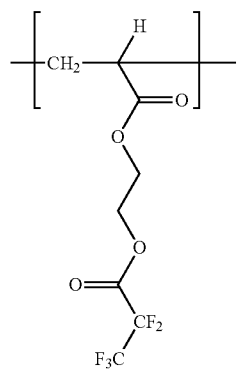
(a4-1-8)
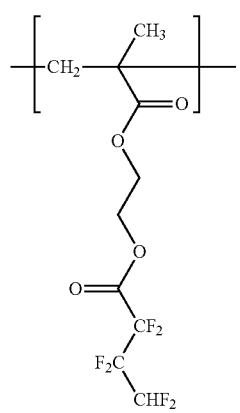
(a4-1-9)
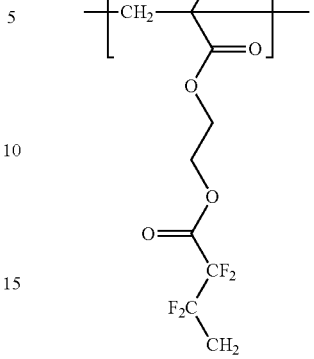
(a4-1-10)
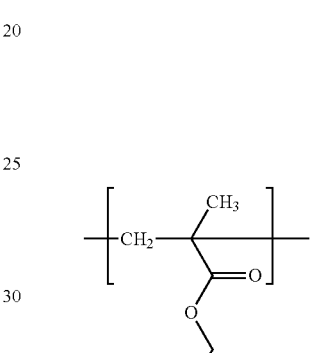
(a4-1-11)
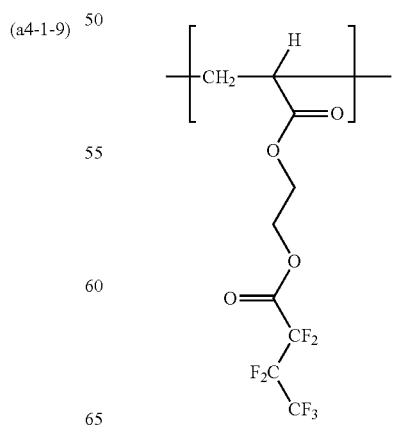
(a4-1-12)

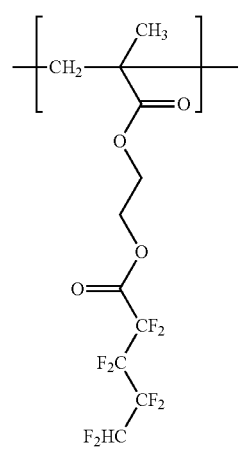
(a4-1-13)
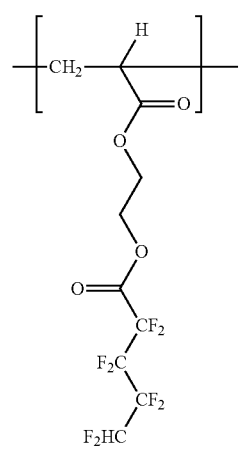
(a4-1-14)
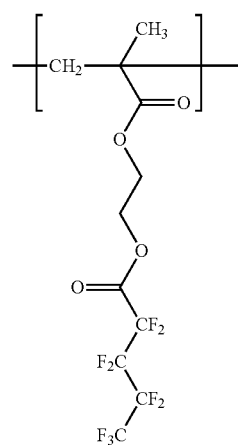
(a4-1-15)
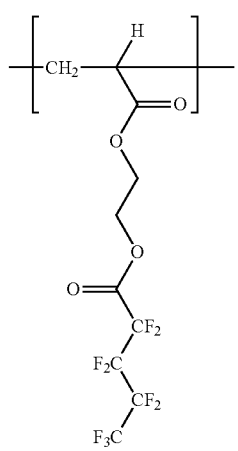
(4a-1-16)
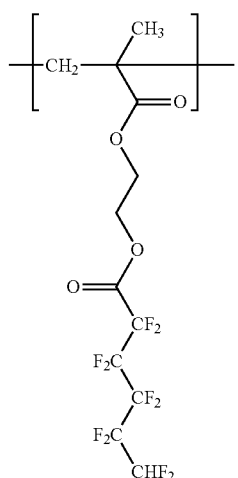
(a4-1-17)
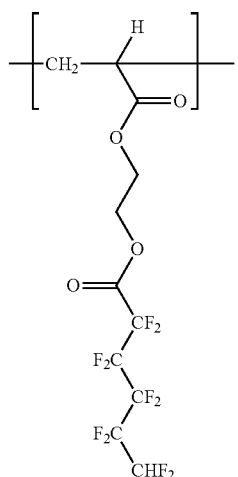
(a4-1-18)

(a4-1-19) 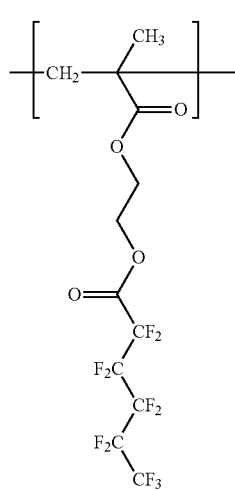
(a4-1-20) 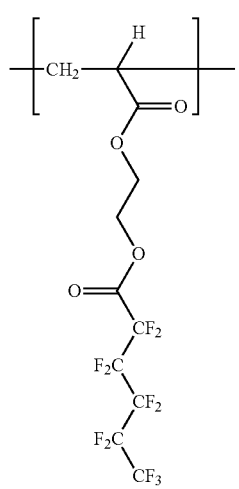
(a4-1-21) 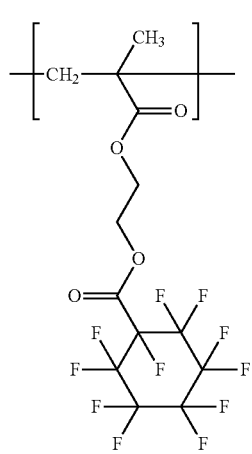
(a4-1-22) 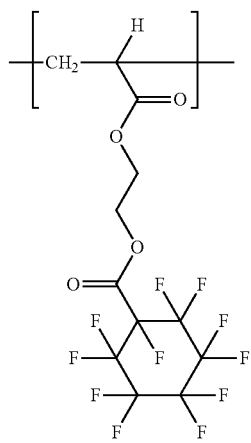
Examples of the structural unit represented by formula (a4-3) include preferably those represented by formulae (a4-1'-1) to (a4-1'-22).
(a4-1'-1) 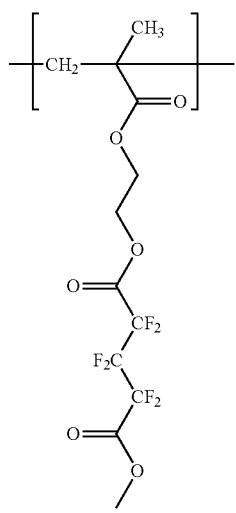
(a4-1'-2) 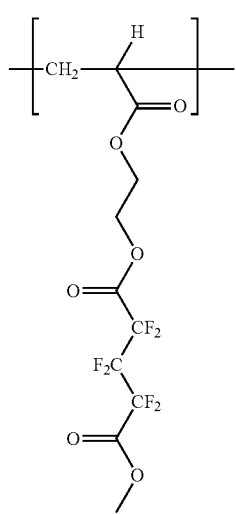

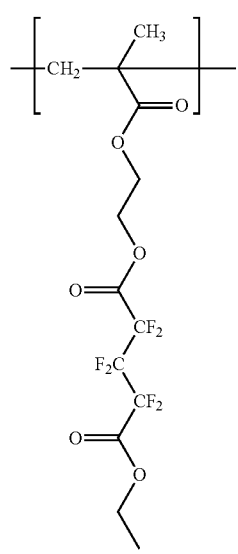
(a4-1'-3)
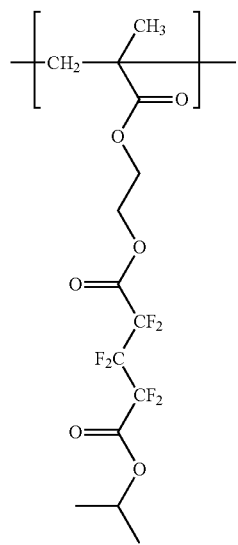
(a4-1'-4)
(a4-1'-5)
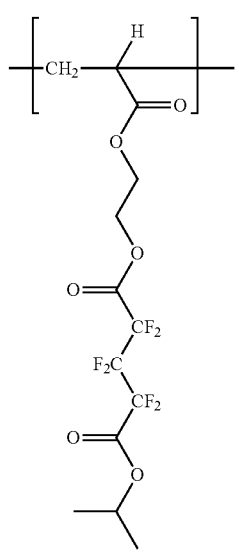
(a4-1'-6)
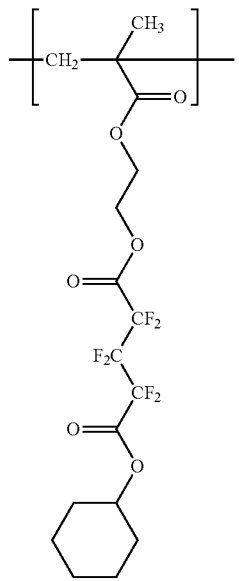
(a4-1'-7)

(a4-1'-8)
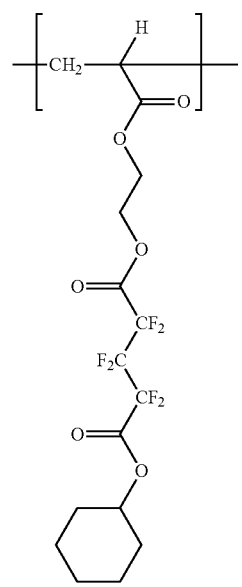
(a4-1'-10)
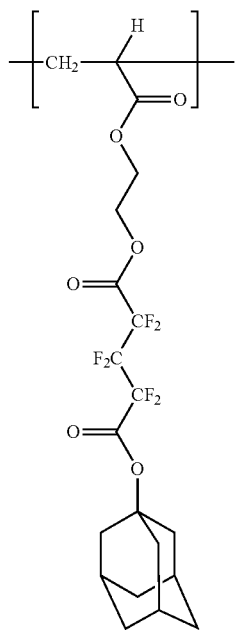
(a4-1'-9)
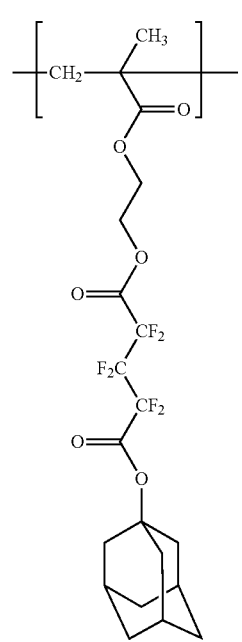
(a4-1'-11)
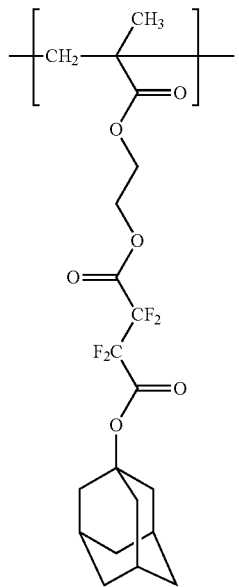

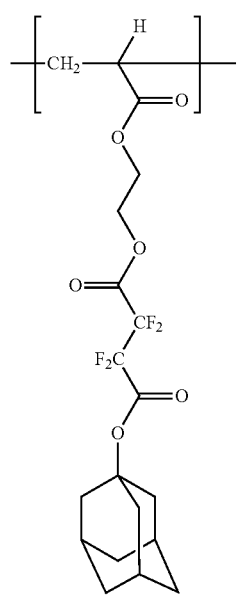
(a4-1'-12)
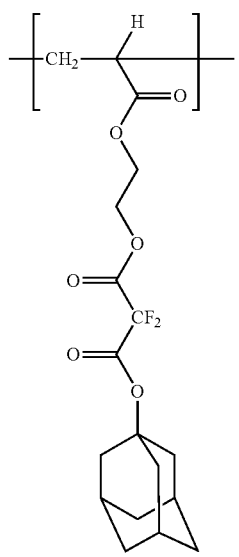
(a4-1'-14)
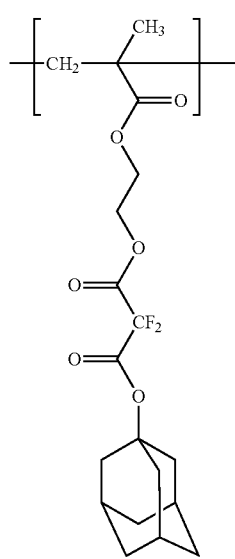
(a4-1'-13)
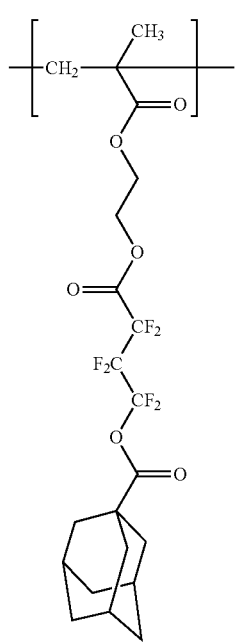
(a4-1'-15)

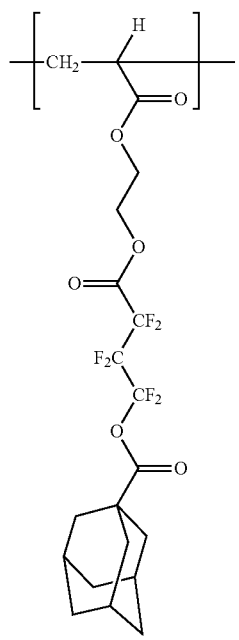
(a4-1'-16)
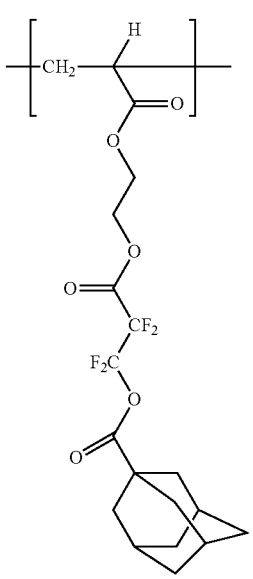
(a4-1'-18)
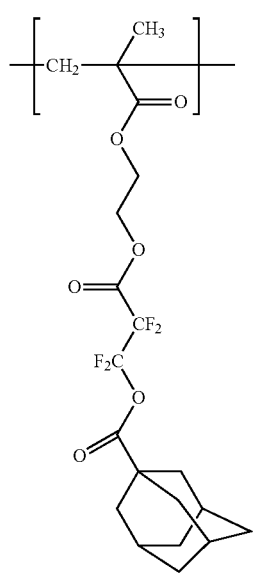
(a4-1'-17)
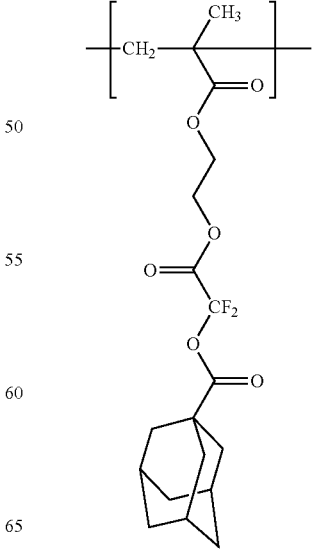
(a4-1'-19)

(a4-1'-20)

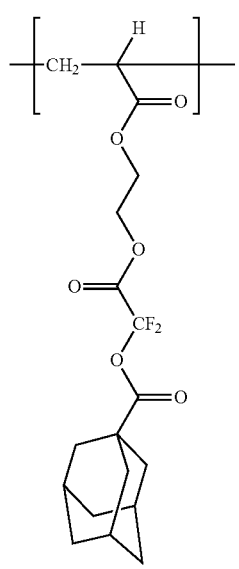

(a4-1'-21)

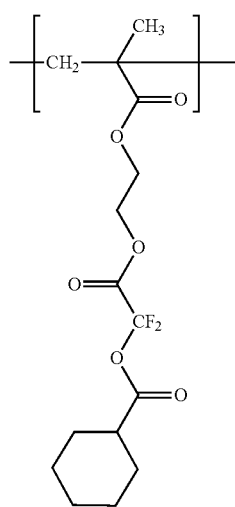

(a4-1'-22)

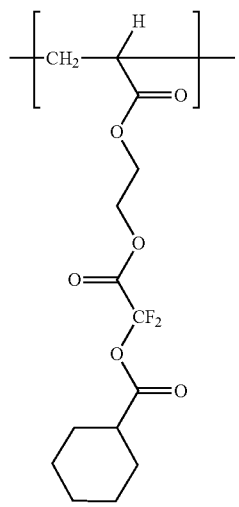

Another example of the structural unit (a4) includes those represented by formula (a4-4).

(a4-4)

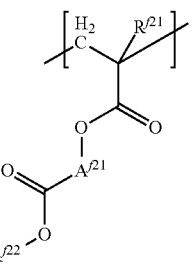

In formula (a4-4), wherein $R^{/21}$ represents a hydrogen atom or a methyl group;

$A^{/21}$ represents —$(CH_2)_{j1}$—, —$(CH_2)_{j2}$—O—$(CH_2)_{j3}$— or —$(CH_2)_{j4}$—CO—O—$(CH_2)_{j5}$— where j1, j2, j3, j4 or j5 each independently represent an integer of 1 to 6; and $R^{/22}$ represents a C1-C10 monovalent hydrocarbon group having a fluorine atom.

For $R^{/22}$, examples of monovalent hydrocarbon group having a fluorine atom include those as referred to for $R^{/2}$.

$R^{/22}$ is preferably a C1-C10 monovalent alkyl group having a fluorine atom or a C3-C10 monovalent alicyclic hydrocarbon group having a fluorine atom, more preferably a C1-C10 monovalent alkyl group having a fluorine atom, and still more preferably a C1-C6 monovalent alkyl group having a fluorine atom.

In formula (a4-4) $A^{/21}$ is preferably —$(CH_2)_{j1}$—, more preferably a methylene or ethylene group, and still more preferably a methylene group.

Examples of the structural unit (a4-4) include preferably the following ones.

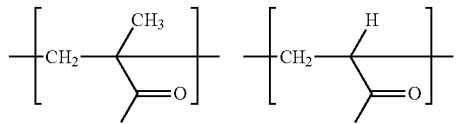

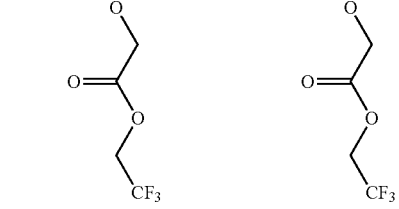

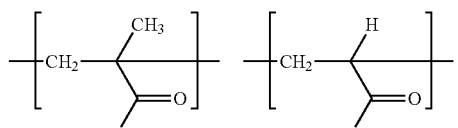

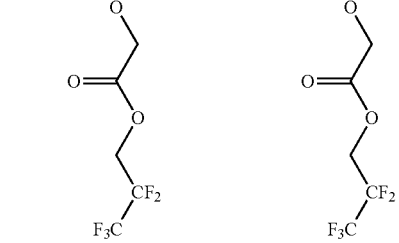

107
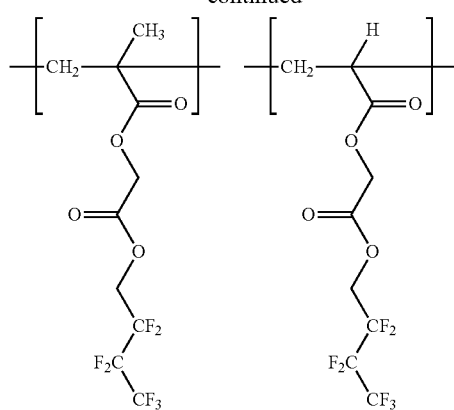
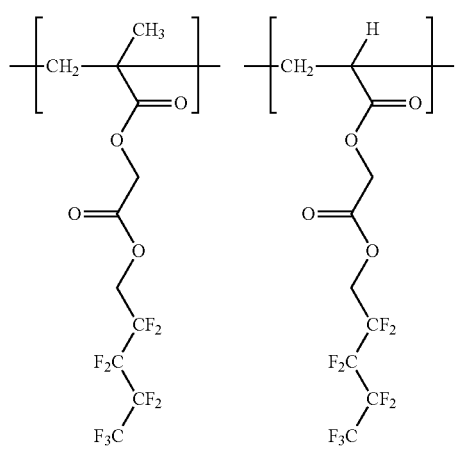
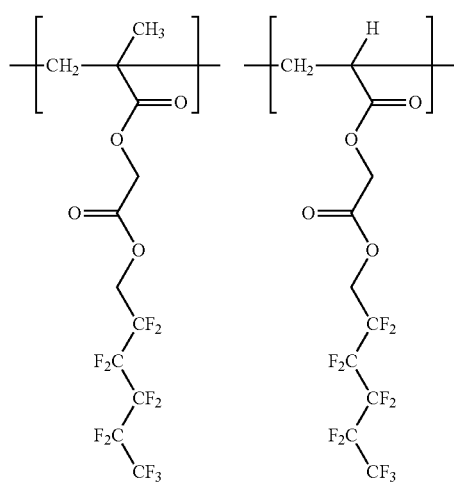
108
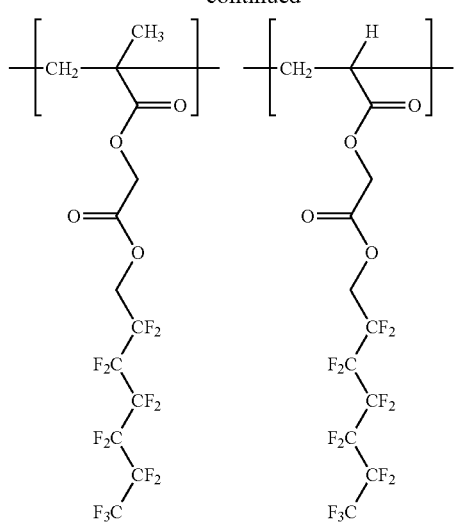
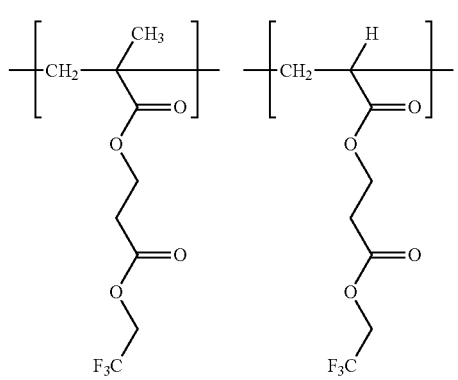
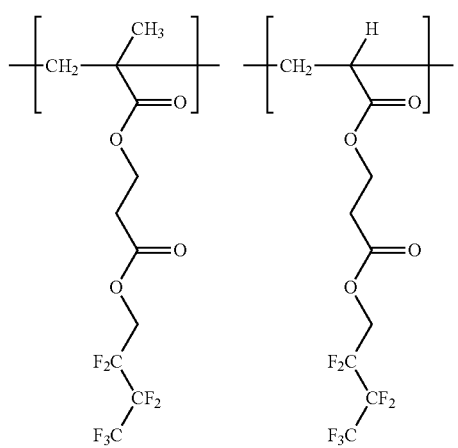

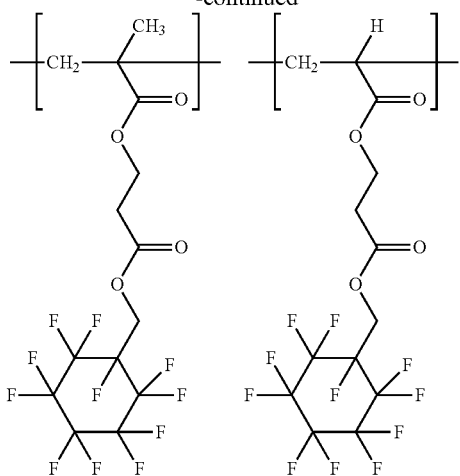

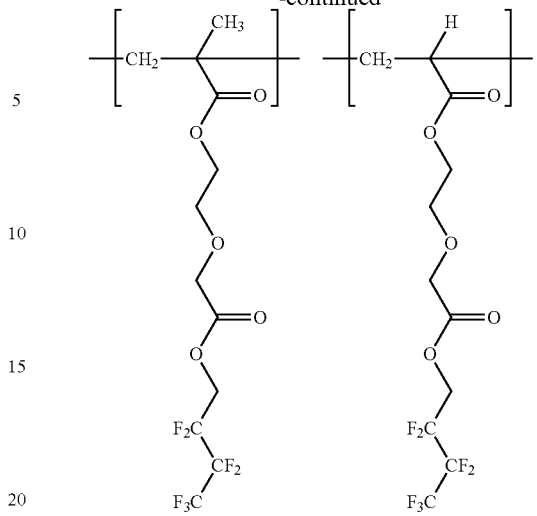

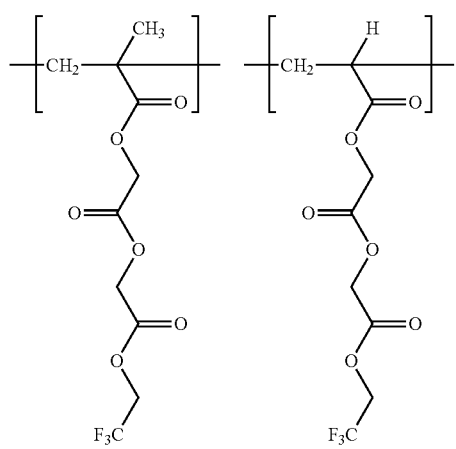

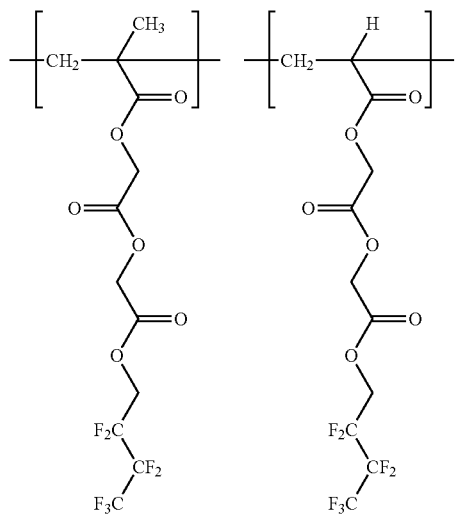

When Resin (A) comprises the structural unit represented by formula (a4), its content is preferably 1 to 20% by mole, more preferably 2 to 15% by mole and still more preferably 3 to 10% by mole based on 100% by mole of all the structural units of the resin.

Examples of another structural unit having no acid-labile group include a structural unit which has a hydrocarbon not being removed therefrom by action of an acid.

Other examples of the structural unit having no acid-labile group include one having an acid-stable hydrocarbon group.

Herein, the term "acid-stable hydrocarbon group" means such a hydrocarbon group that is not removed from the structural unit having the group by action of an acid generated from an acid generator as described later.

The acid-stable hydrocarbon group may be a linear, branched or cyclic hydrocarbon group.

The structural unit which has a hydrocarbon not being removed therefrom by action of an acid can have a linear, branched or cyclic hydrocarbon, preferably an alicyclic hydrocarbon group.

Examples of the structural unit having an acid-stable hydrocarbon group include one represented by formula (a5-1):

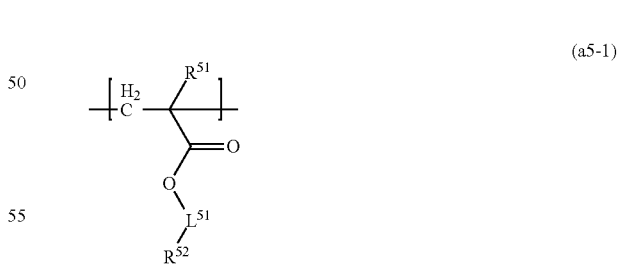

(a5-1)

where $R^{51}$ represents a hydrogen atom or a methyl group;
$R^{52}$ represents a C3-C18 monovalent alicyclic hydrocarbon group which can have a C1-C8 monovalent aliphatic hydrocarbon group as a substituent, provided that the alicyclic hydrocarbon group has no substituent on the carbon atom bonded to $L^{51}$; and
$L^{51}$ represents a single bond or a C1-C18 divalent saturated hydrocarbon group where a methylene group can be replaced by an oxygen atom or carbonyl group.

The alicyclic hydrocarbon group represented by $R^{52}$ may be monocyclic or polycyclic one.

Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the aliphatic hydrocarbon group include an alkyl groups such as a methyl group, an ethyl group, n-propyl group, isopropyl group, n-butyl group, sec-butyl group, tert-butyl group, a pentyl group, a hexyl group, an octyl group and 2-ethylhexyl group.

Examples of the alicyclic hydrocarbon group having a substituent include a 3-hydroxyadamantyl group, and a 3-methyladamantyl group. $R^{52}$ is preferably a C3-C18 unsubstituted alicyclic hydrocarbon group, more preferably an adamantyl group, a norbornyl group or a cyclohexyl group.

Examples of the divalent saturated hydrocarbon group represented by $L^{51}$ include divalent aliphatic hydrocarbon groups and divalent alicyclic hydrocarbon groups, preferably divalent aliphatic hydrocarbon groups.

Examples of divalent aliphatic hydrocarbon groups include alkanediyl groups such as a methylene group, an ethylene group, a propanediyl group, a butanediyl group and a pentanediyl group.

The divalent alicyclic hydrocarbon groups may be monocyclic or polycyclic one.

Examples of divalent monocyclic hydrocarbon groups include cycloalkanediyl groups such as a cyclopentanediyl group and a cyclohexanediyl group. Examples of divalent polycyclic alicyclic hydrocarbon groups include an adamantanediyl group and a norbornanediyl group.

Examples of the divalent hydrocarbon group where a methylene group has been replaced by an oxygen atom or carbonyl group include those represented by formulae (L1-1) to (L1-4).

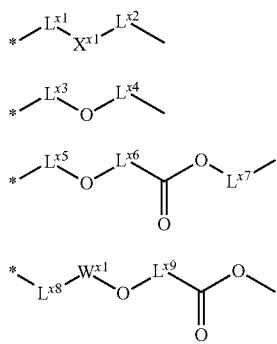

(L1-1)

(L1-2)

(L1-3)

(L1-4)

In these formulae, * represents a binding site to an oxygen atom.

$X^{x1}$ is a carbonyloxy group or an oxycarbonyl group; and $L^{x1}$ is a C1-C16 divalent saturated hydrocarbon group, and $L^{x2}$ is a single bond or a C1-C15 divalent aliphatic saturated hydrocarbon group, provided that the total number of the carbon atoms in $L^{x1}$ and $L^{x2}$ is 16 or less.

$L^{x3}$ is a C1-C17 divalent saturated hydrocarbon group, and $L^{x4}$ is a single bond or a C1-C16 divalent aliphatic saturated hydrocarbon group, provided that the total number of the carbon atoms in $L^{x3}$ and $L^{x4}$ is 17 or less.

$L^{x5}$ is a C1-C15 divalent saturated hydrocarbon group, and $L^{x6}$ and $L^{x7}$ are a single bond or a C1-C14 divalent aliphatic saturated hydrocarbon group, provided that the total number of the carbon atoms in $L^{x5}$, $L^{x6}$ and $L^{x7}$ is 15 or less.

$L^{x8}$ and $L^{x9}$ are each independently a single bond or a Divalent C1-C12 aliphatic saturated hydrocarbon group, and $W^{x1}$ is a C3-C15 divalent cyclic saturated hydrocarbon group, provided that the total number of the carbon atoms in $L^{x8}$, $L^{x9}$ and $W^{x1}$ is 15 or less.

$L^{x1}$ is preferably a C1-C8 divalent saturated hydrocarbon group, more preferably a methylene group or an ethylene group.

$L^{x2}$ is preferably a single bond, or a C1-C8 divalent saturated hydrocarbon group, more preferably a single bond.

$L^{x3}$ is preferably a C1-C8 divalent saturated hydrocarbon group, more preferably a methylene group or an ethylene group.

$L^{x4}$ is preferably a single bond or a C1-C8 divalent saturated hydrocarbon group, more preferably a single bond, a methylene group or an ethylene group.

$L^{x5}$ is preferably a C1-C8 divalent saturated hydrocarbon group, more preferably a methylene group or an ethylene group.

$L^{x6}$ is preferably a single bond or a C1-C8 divalent saturated hydrocarbon group, more preferably a methylene group or an ethylene group.

$L^{x7}$ is preferably a single bond or a C1-C8 divalent saturated hydrocarbon group, more preferably a methylene group or an ethylene group.

$L^{x8}$ is preferably a single bond or a C1-C8 divalent saturated hydrocarbon group, more preferably a single bond or a methylene group.

$L^{x9}$ is preferably a single bond or a C1-C8 divalent saturated hydrocarbon group, more preferably a single bond or a methylene group.

$W^{x1}$ is a preferably C3-C10 divalent cyclic saturated hydrocarbon group, more preferably a cyclohexanediyl group or an adamantanediyl group.

Examples of the divalent hydrocarbon group represented by formula (L1-1) include the following ones.

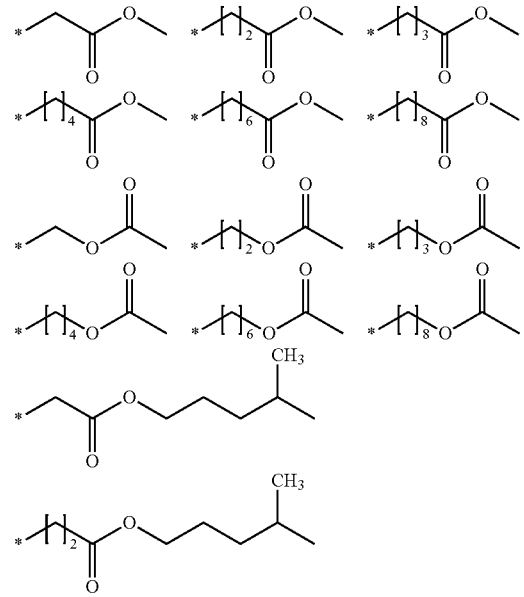

-continued

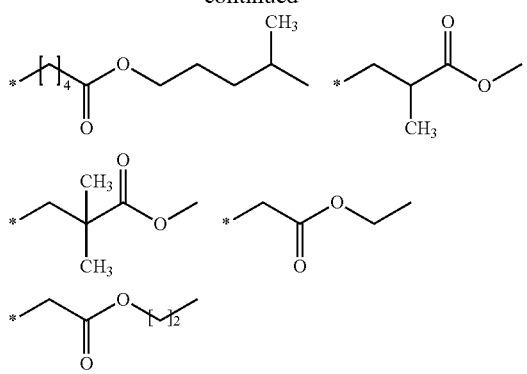

In these formulae, * represents a binding site to an oxygen atom.

Examples of the divalent hydrocarbon group represented by formula (L1-2) include the following ones.

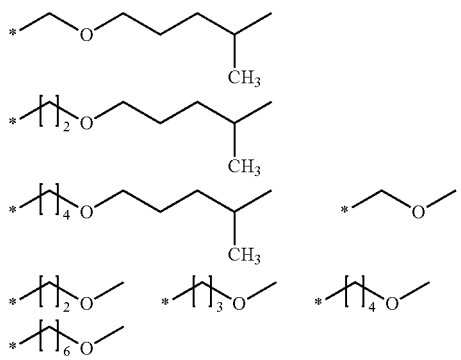

In these formulae, * represents a binding site to an oxygen atom.

Examples of the divalent hydrocarbon group represented by formula (L1-3) include the following ones.

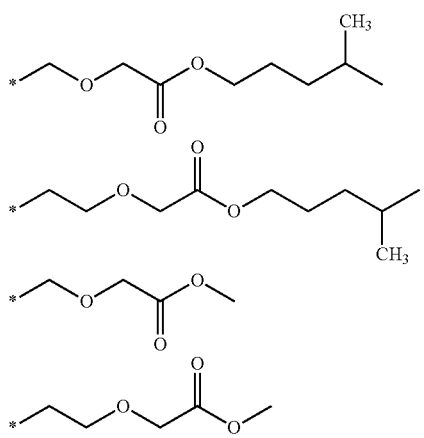

In these formulae, * represents a binding site to an oxygen atom.

Examples of the divalent hydrocarbon group represented by formula (L1-4) include the following ones.

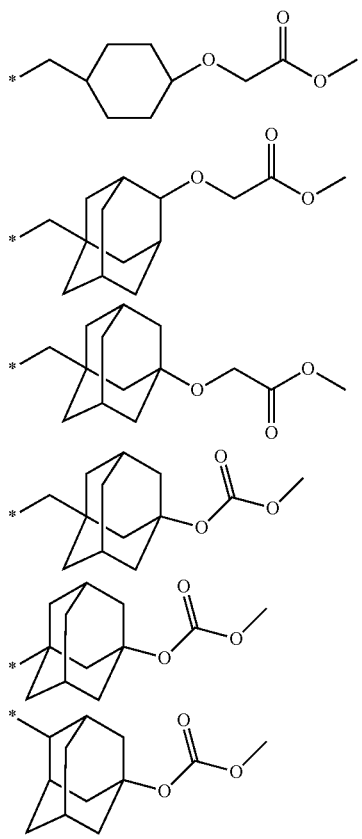

In these formulae, * represents a binding site to an oxygen atom. $L^{51}$ is preferably a single bond or a group represented by formula (L1-1).

Examples of the structural unit represented by formula (a5-1) include the following ones and those where a methyl group has been replaced by a hydrogen atom in each formula.

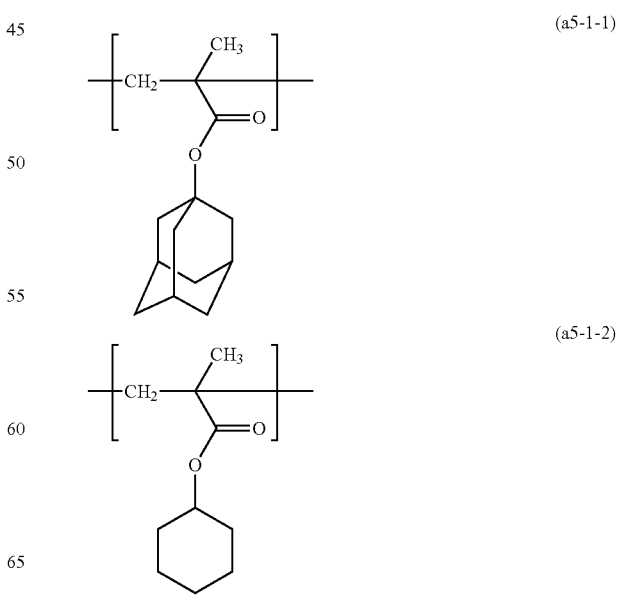

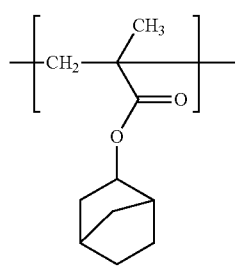
(a5-1-3)
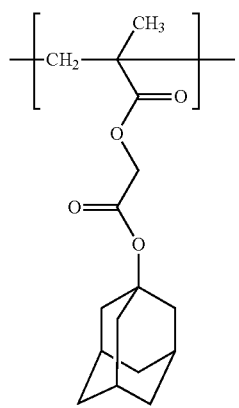
(a5-1-4)
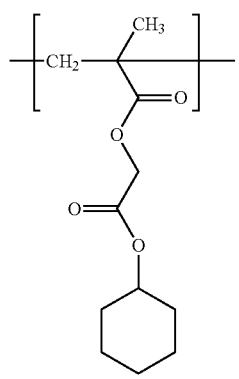
(a5-1-5)
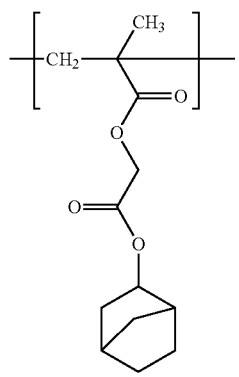
(a5-1-6)
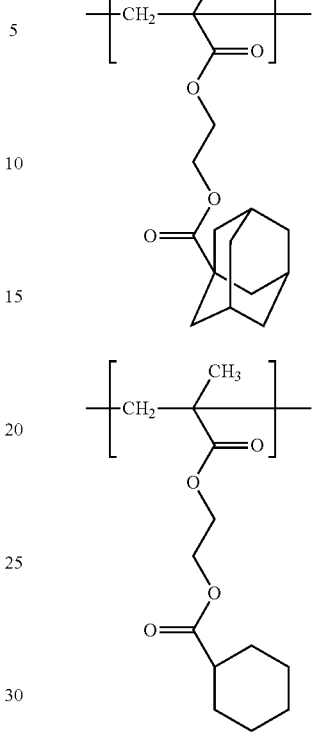
(a5-1-7)
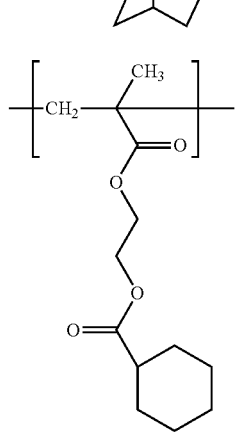
(a5-1-8)
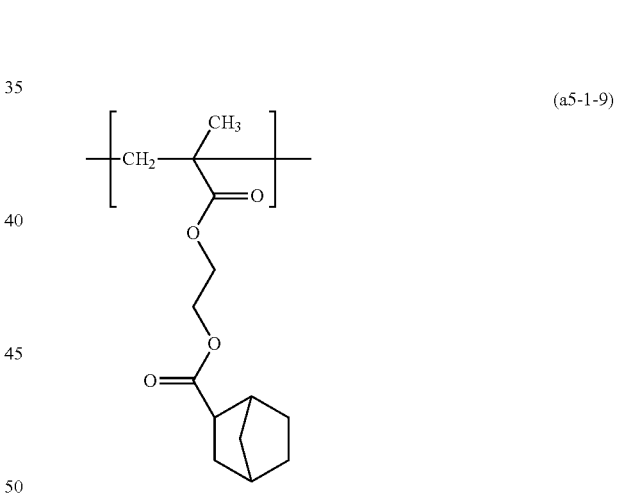
(a5-1-9)
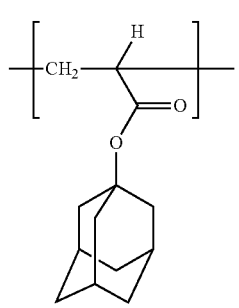
(a5-1-10)

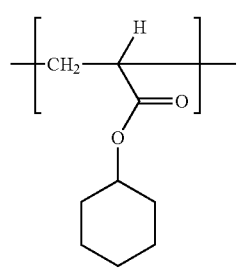 (a5-1-11)
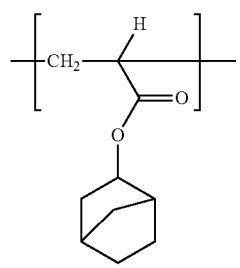 (a5-1-12)
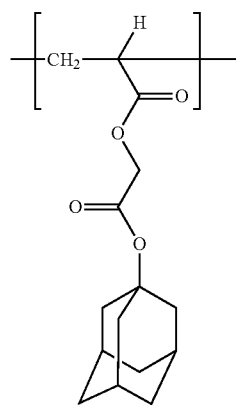 (a5-1-13)
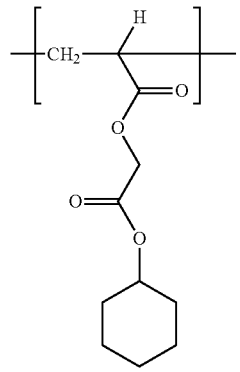 (a5-1-14)
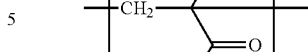 (a5-1-15)
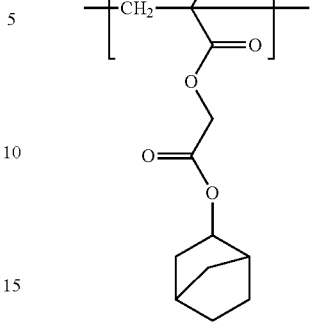
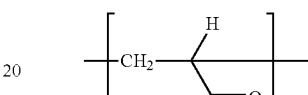 (a5-1-16)
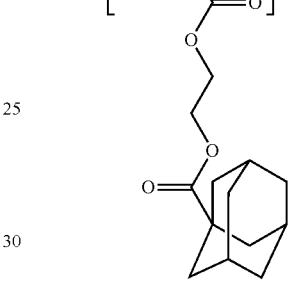
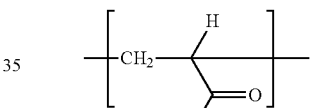 (a5-1-17)
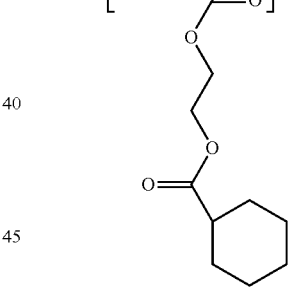
 (a5-1-18)
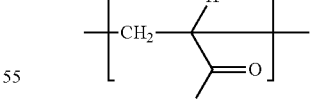
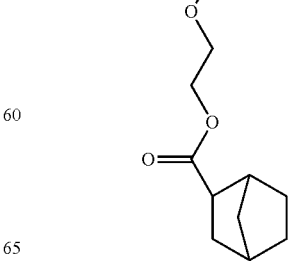

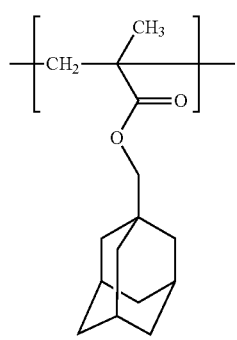 (a5-1-19)
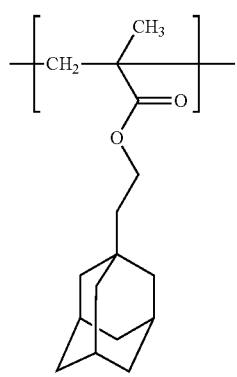 (a5-1-20)
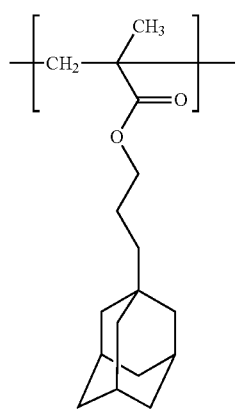 (a5-1-21)
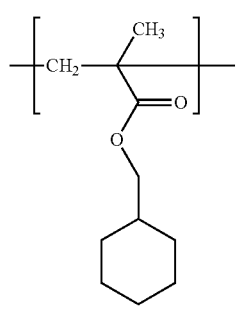 (a5-1-22)
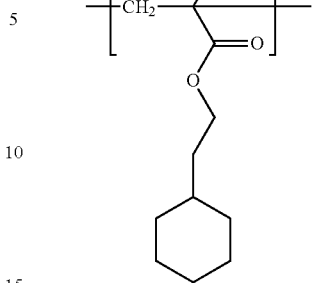 (a5-1-23)
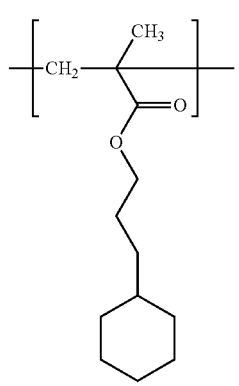 (a5-1-24)
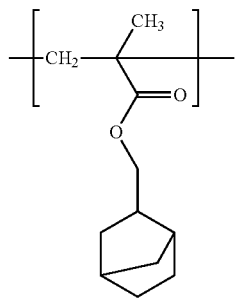 (a5-1-25)
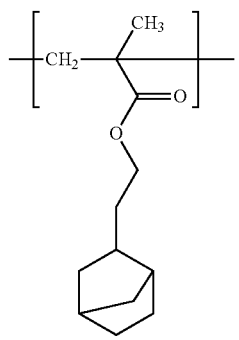 (a5-1-26)

(a5-1-27)

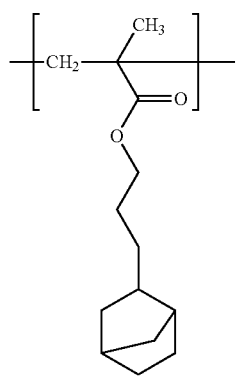

Resin (A) may further comprise another structural unit examples of which include one known to skilled in the art.

Resin (A) comprises preferably the structural unit (a1) and the structural unit (s), that is a copolymer of Monomer (a1) and a monomer from which the structural unit (s) is derived.

In Resin (A), the structural unit (a1) is one of the structural unit (a1-1) and the structural unit (a1-2) which preferably comprises a cyclohexyl group or a cyclopentyl group. Preferably, Resin (A) comprises the structural unit (a1-1) and the structural unit (a1-2), or the structural unit (a1-1) as the structural unit (a1).

The structural unit (s) is preferably one of the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4).

Resin (A) comprises preferably the structural unit (a1) derived from a structural unit having an adamantyl group, preferably structural unit (a1-1). The content of the structural unit having an adamantyl group is preferably 15% by mole or more of the total amount of the structural unit (a1). The more is the structural unit having an adamantyl group, the more improved is the resistance of the photoresist film to dry etching.

Resin (A) can be produced according to known polymerization methods such as radical polymerization.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

<Another Resin>

The composition of the disclosure may comprise another resin than Resin (A).

Examples of another resin include resin which consists of the structural units (s).

Another resin than Resin (A) comprises preferably a structural unit (a4), more preferably a structural unit (a4) having a fluorine atom.

In another resin, its content of the structural unit (a4) is preferably 40% or more by mole, more preferably 45% or more by mole, still more preferably 50% or more by mole, and further more preferably 80% or more, by mole based on 100% by mole of all the structural units of the resin.

Another resin may further comprise another structural unit such as the structural unit (a2), the structural unit (a3) and another structural unit known in the art.

Another resin usually has 8000 or more of the weight-average molecular weight, preferably 10000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

The content of another resin is preferably 1 to 60 weight parts, more preferably 1 to 60 weight parts, and still more preferably 1 to 50 weight parts, and further still more preferably 1 to 40 weight parts, relative to 100 parts of Resin (A). Its content may be in the range of 2 to 30 weight parts relative to 100 parts of Resin (A).

The total content of the resins in the photoresist composition of the disclosure is usually 80% by mass or more based on sum of solid component, and usually 99% by mass or less.

In this specification, "solid component" means components other than solvent in the photoresist composition.

The photoresist composition of the disclosure may comprise a solvent.

The amount of the solvent is usually 90% by weight or more, preferably 92% by weight or more preferably 94% by weight or more based on total amount of the photoresist composition of the disclosure.

The amount of the solvent is usually 99.9% by weight or less and preferably 99% by weight or less based on total amount of the photoresist composition of the disclosure. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. The photoresist composition may comprise two or more solvents.

The photoresist compositions of the disclosure may further comprise a quencher such as a basic compound. The "quencher" has the property that it can trap an acid, especially an acid generated from the acid generator by applying radiation thereto.

Examples of the quencher include a basic compound, such as a basic nitrogen-containing organic compound, and a salt which generates an acid having acidity weaker than an acid generator.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2 tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

Herein, the acidity in the salts is shown by the acid dissociation constant (pKa).

The acid dissociation constant of acid generated from the salt for a quencher is usually a salt of −3<pKa.

The salt for a quencher is preferably a salt of −1<pKa<7, and more preferably a salt of 0<pKa<5.

Specific examples of the salt for a quencher include the following ones, the salt of formula (D), and salts recited in US2012/328986A1, US2011/171576A1, US2011/201823A1, JP2011-39502A1, and US2011/200935A1.

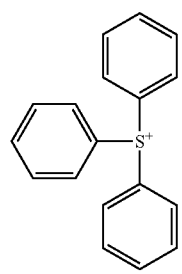

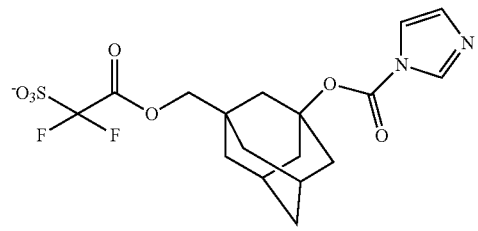

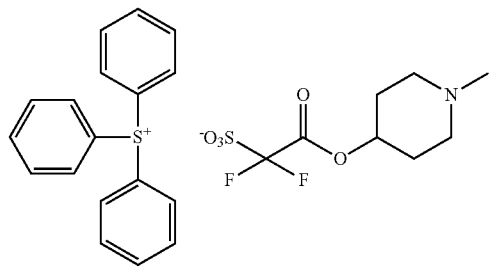

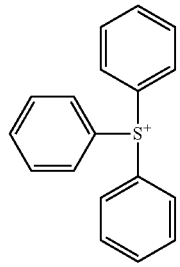

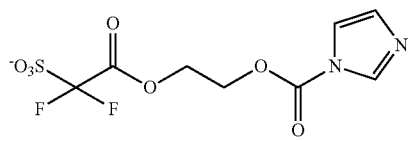

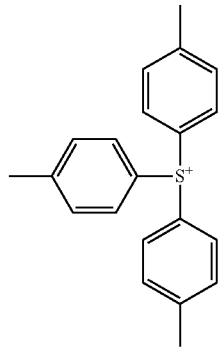

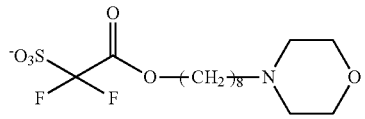

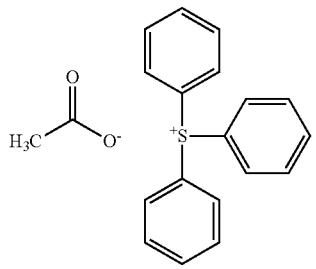

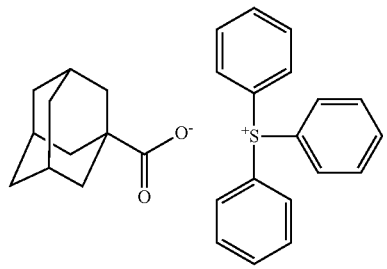

-continued

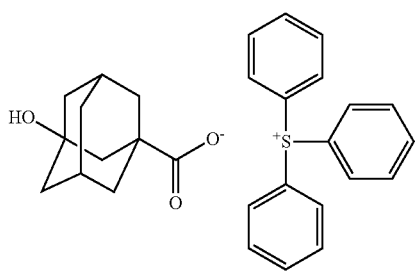

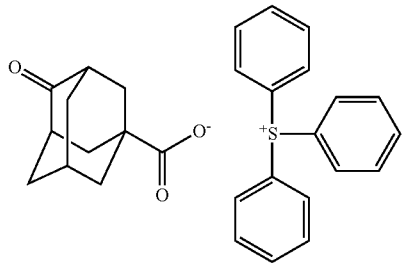

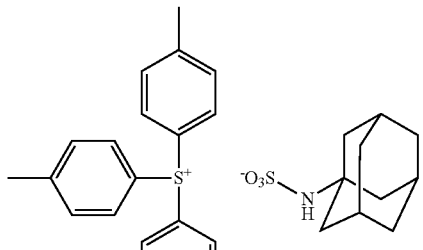

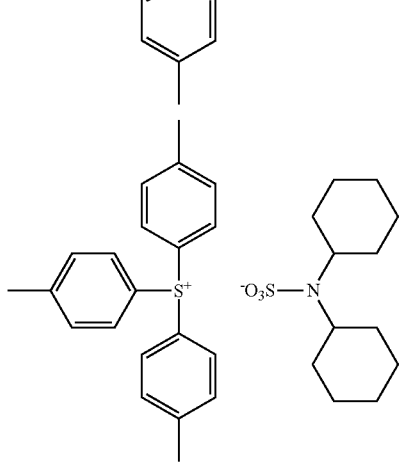

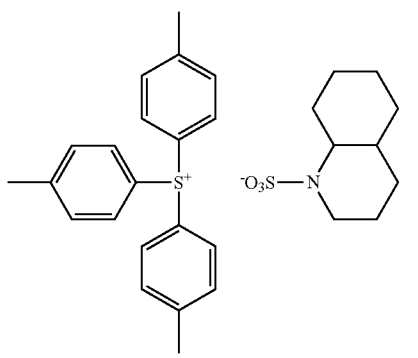

-continued

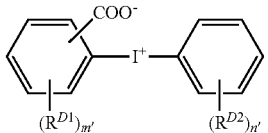

(D)

In formula (D), $R^{D1}$ and $R^{D2}$ respectively represent a C1-C12 monovalent hydrocarbon group, a C1-C6 alkoxy group, a C2-C7 acyl group, a C2-C7 acyloxy group, a C2-C7 alkoxycarbonyl group, a nitro group or a halogen atom.

The symbols m' and n' each independently represent an integer of 0 to 4, preferably an integer of 0 to 2, and more preferably 0. The hydrocarbon group represented by $R^{D1}$ and $R^{D2}$ includes a C1-C12 alkyl group, a C3-C12 monovalent alicyclic hydrocarbon group, a C6-C12 monovalent aromatic hydrocarbon group, and any combination of them.

Examples of the monovalent hydrocarbon group include C1-C12 alkyl groups such as a methyl group, an ethyl group, propyl group, a butyl group, a pentyl group, a hexyl group, a heptyl group, an octyl group, a nonyl group.

Examples of the alicyclic hydrocarbon group, which may be a monocyclic or polycyclic one, include C3-C12 cycloalkyl groups such as a cyclopropyl group, a cyclobutyl group, a cyclopentyl group, a cyclohexyl group, and norbonyl group and adamantyl group.

Examples of the aromatic hydrocarbon group include C6-C12 aryl group such as a phenyl group and a naphthyl group.

Examples of alkoxy groups include a methoxy group and an ethoxy group. Examples of acyl groups include an acetyl group, a propanoyl group, a benzoyl group and a cyclohexanecarbonyl group.

Examples of acyloxy group include groups where an oxy group [—O—] is attached to any one of the acyl groups as mentioned above.

Examples of alkoxycarbonyl group include groups where a carbonyl group [—CO—] is attached to any one of the alkoxy groups as mentioned above. Examples of halogen atoms include fluorine atoms, a chlorine atom, and a bromine atom.

Examples of the compounds of formula (D) include the following ones.

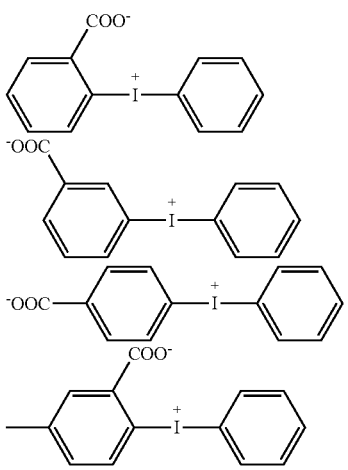

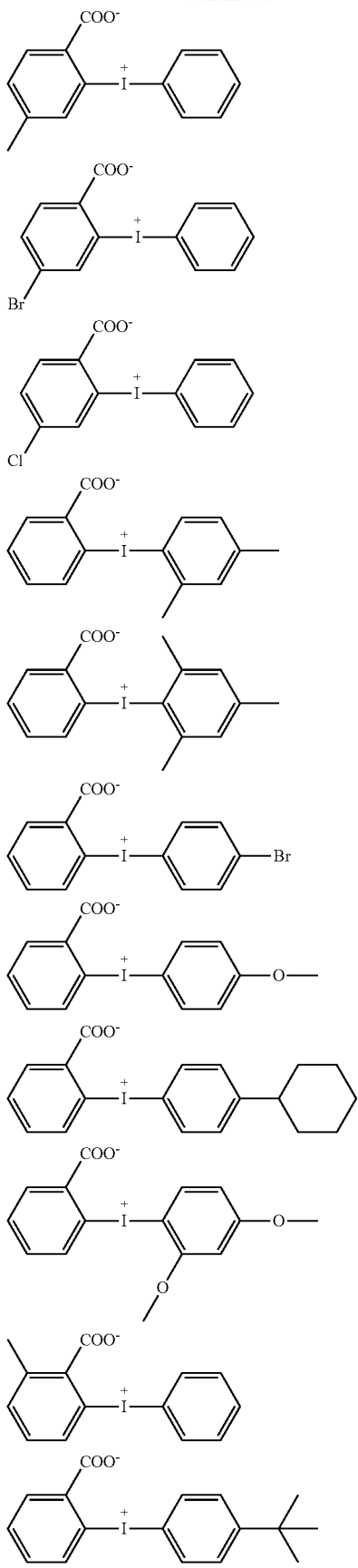
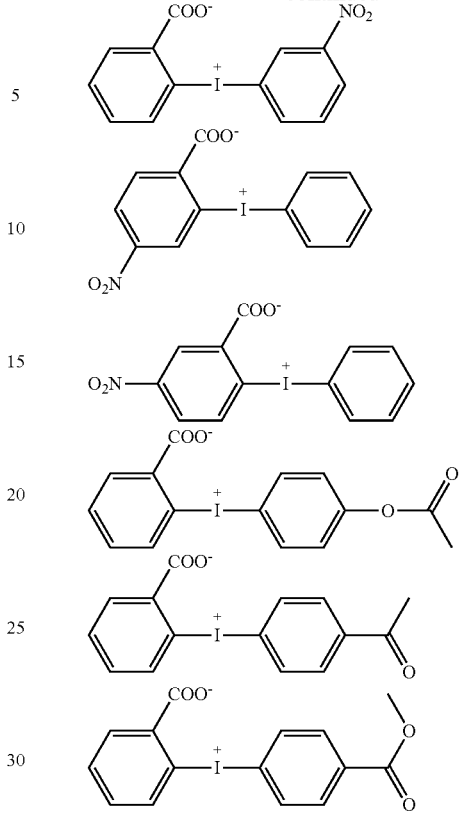

The compound represented by formula (D) can be produced according to the method recited in Tetrahedron Vol. 45, No. 19, p6281-6296.

The compound is available on the market.

The content of quencher is preferably 0.01 to 5% by mass, more preferably 0.01 to 4% by mass, still more preferably 0.01 to 3% by mass, and further more preferably 0.01 to 1% by mass, based on sum of solid component.

The photoresist compositions of the disclosure may comprise, if necessary, a small amount of various additives such as a sensitizer, a dissolution inhibitor, other polymers, a surfactant, a stabilizer and a dye as long as the effect of the present invention is not prevented.

The photoresist compositions of the disclosure can usually be prepared by mixing, in a solvent, Resin (A) and the salt represented by formula (I), and if necessary another resin, a quencher, and/or additives at a suitable ratio for the composition, optionally followed by filtrating the mixture with a filter having 0.003 μm to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

A photoresist pattern can be produced by the following steps (1) to (5):

(1) a step of applying the photoresist composition of the disclosure on a substrate,
(2) a step of forming a composition film by conducting drying,
(3) a step of exposing the composition film to radiation,
(4) a step of baking the exposed composition film, and
(5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 µm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the disclosure, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the disclosure, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethyleether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the disclosure is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the disclosure.

The "%" and "part(s)" used to represent the content of any component and the amount of any material used in the following examples and comparative examples are on a mass basis unless otherwise specifically noted.

The weight-average molecular weight of any material used in the following examples was determined with gel permeation chromatography under the following condition.
Equipment: HLC-8120 GPC type, manufactured by TOSOH CORPORATION
Column: Three of TSKgel Multipore HXL-M with guard column, manufactured by TOSOH CORPORATION
Solvent: tetrahydrofuran
Flow rate: 1.0 mL/min.
Detector: RI Detector
Column temperature: 40° C.
Injection volume: 100 µL
Standard reference material: Standard polystyrene (manufactured by TOSOH CORPORATION)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Here, the values at the peaks of the spectrum are referred to as "MASS."

Example 1

-continued

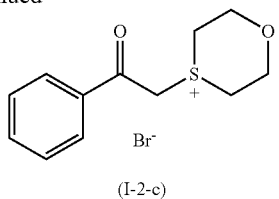

(I-2-c)

To a reactor, 10 parts of the compound represented by formula (I-2-a) and 25 parts of acetone were added and then they were stirred at 23° C. for 30 minutes.

Into the obtained mixture, 5.23 parts of the compound represented by formula (I-2-b) was dropped over 5 minutes and then stirred at 23° C. for 30 minutes, and further at 50° C. for 6 hours.

Then the mixture was filtrated to obtain 1.75 parts of the salt represented by formula (I-2-c).

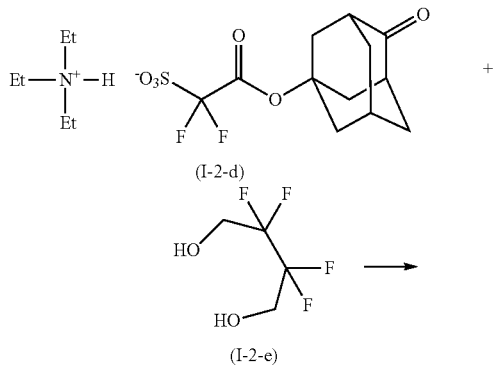

To a reactor, 130 parts of compounds represented by formula (I-2-d), 73.83 parts of compounds represented by formula (I-2-e) and 780 parts of chloroform were added and stirred at 23° C. for 30 minutes. Into the obtained mixture, 0.46 parts of sulfuric acid was dropped, and further refluxed while being stirred at 62° C. for 24 hours, followed by cooling to 23° C.

To the obtained reaction mixture, 2.3 parts of trimethylamine was added to obtain a solution which contained 151.55 parts of salt represented by formula (I-2-f). The concentration of the salt in the solution was 17.2%.

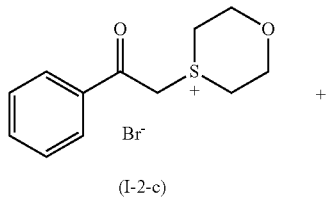

(I-2-c)

-continued

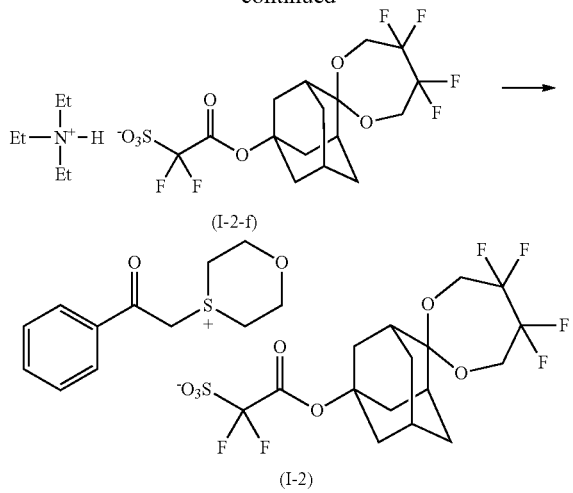

To a reactor, 3.3 parts of the salt represented by formula (I-2-c) and the solution which contained 5.16 parts of salt represented by formula (I-2-f) were added and stirred at 23° C. for one hour.

For washing the obtained reaction mixture, 10 parts of ion exchanged water was added thereto and stirred, followed by separating the chloroform layer therefrom: The washing step was conducted five times.

Then the chloroform layer was concentrated. To the obtained residue, 30 parts tert-butylmethylether was added and stirred at 23° C. for 30 minutes, followed by being filtrated to obtain 5.53 parts of the salt represented by formula (I-2).

MASS (ESI (+) Spectrum): M+ 223.1
MASS (ESI (−) Spectrum): M− 467.1

Example 2

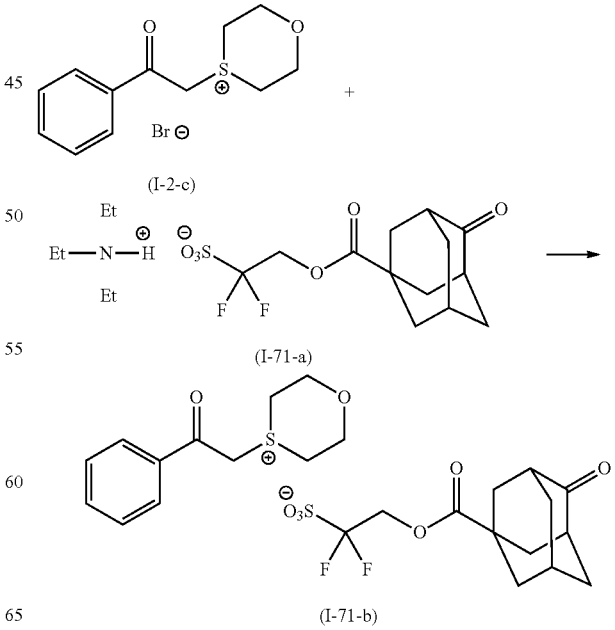

To a reactor, 3.98 parts of salt represented by formula (I-71-a), which had been prepared according to a method recited in Examples of JP2011-116747A1., 3.3 parts of the salt represented by formula (I-2-c), 60 parts of chloroform and 30 parts of ion exchanged water were added and stirred at 23° C. for 12 hours.

The organic layer was separated from the obtained reaction mixture. Then 30 parts of ion exchanged water was added to the organic layer and stirred at 23° C. for 30 minutes, followed by separating the organic layer therefrom: The washing step was conducted twice.

Then the chloroform layer was concentrated. To the obtained residue, 30 parts tert-butylmethylether was added and stirred, followed by removing its supernatant therefrom. The obtained residue was concentrated to obtain 2.95 parts of the salt represented by formula (I-71-b).

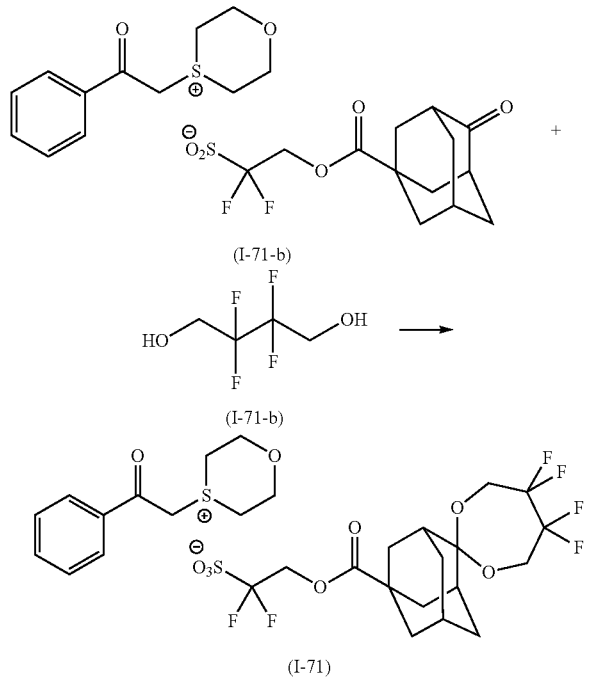

To a reactor, 2.39 parts of the salt represented by formula (I-71-b) and 20 parts of 1,2-dichloroethane were added and stirred at 23° C. for 30 minutes. Then thereto 2.77 parts of the compound represented by formula (I-71-c) and 0.15 parts of p-toluenesulfonic acid were added and further refluxed while being stirred at 100° C. for 3 hours, followed by cooling to 23° C.

To the obtained reaction mixture, 60 parts of chloroform and 17.7 parts of 8.7% aqueous sodium hydrogencarbonate solution were added and then stirred at 23° C. for 30 minutes, followed by separating an organic layer therefrom.

To the collected organic layer, 60 parts of ion exchanged water was added and stirred at 23° C. for 30 minutes, followed by separating the organic layer therefrom: The washing step was conducted five times.

To the obtained organic layer, 0.5 parts of active carbon was added and stirred at 23° C. for 30 minutes, followed by being filtrated.

The filtrate was concentrated to obtain 2.01 parts of salt represented by formula (I-71).

MASS (ESI (+) Spectrum): M$^+$ 223.1
MASS (ESI (−) Spectrum): M$^-$ 481.1

Example 3

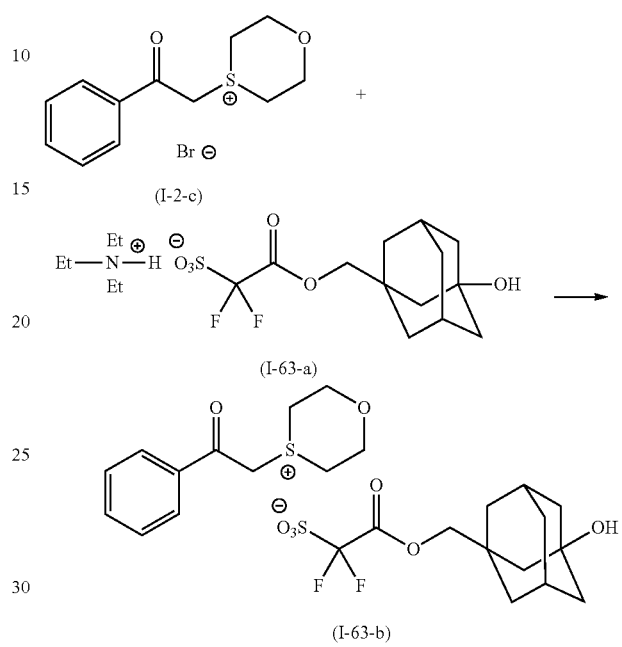

To a reactor, 4 parts of the salt represented by formula (I-63-a), 60 parts of chloroform, 3.3 parts of the salt represented by formula (I-2-c) and 30 parts of ion exchanged water were added and then they were stirred at 23° C. for 12 hours.

Then an organic layer was separated from the obtained reaction mixture, 30 parts of ion exchanged water was added to the organic layer and stirred at 23° C. for 30 minutes, followed by separating the organic layer therefrom: The washing step was conducted twice. Then the organic layer was concentrated. To the obtained residue, 30 parts tert-butylmethylether was added and stirred, followed by removing its supernatant therefrom. The obtained residue was concentrated to obtain 3.66 parts of the salt represented by formula (I-63-b).

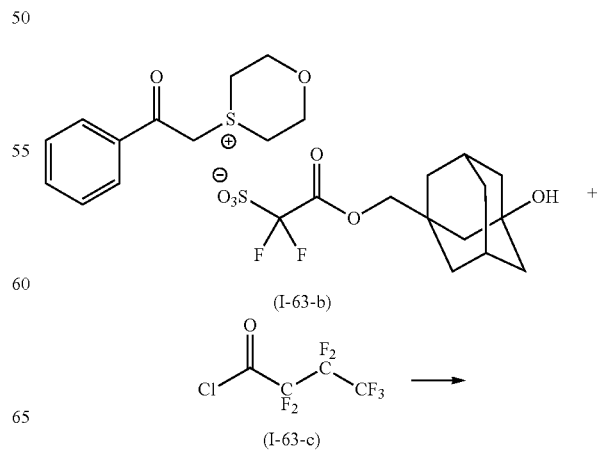

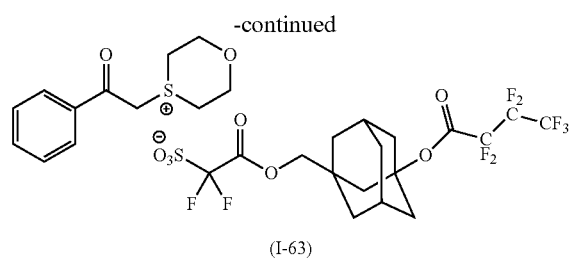

(I-63)

To a reactor, 2.8 parts of the salt represented by formula (I-63-b), 30 parts of chloroform and 0.85 parts of N-methylpyrrolidine were added, and stirred at 0° C. for 30 minutes.

Then thereto 1.74 parts of the compound represented by formula (I-63-c) was added and stirred at 0° C. for 3 hours.

To the obtained mixture, 100 parts of chloroform and 40 parts of 5% aqueous oxalic acid solution were added and stirred, followed by separating an organic layer therefrom.

Then 50 parts of ion exchanged water was added to the organic layer and stirred, followed by separating an organic layer therefrom:

The washing step was conducted five times.

To the obtained organic layer, 1 part of active carbon was added and stirred at 23° C. for 30 minutes, followed by being filtrated. The filtrate was concentrated. To the concentrate, 10 parts of acetonitrile was added to dissolve it, followed by being concentrated. Then 20 parts of ethyl acetate was added thereto and stirred, followed by removing its supernatant therefrom. To the obtained residue, 20 parts tert-butylmethylether was added and stirred, followed by removing its supernatant therefrom. The residue was dissolved in chloroform and concentrated to obtain 2.66 parts of salt represented by formula (I-63).

MASS (ESI (+) Spectrum): M⁺ 223.1
MASS (ESI (−) Spectrum): M⁻ 535.1

Example 4

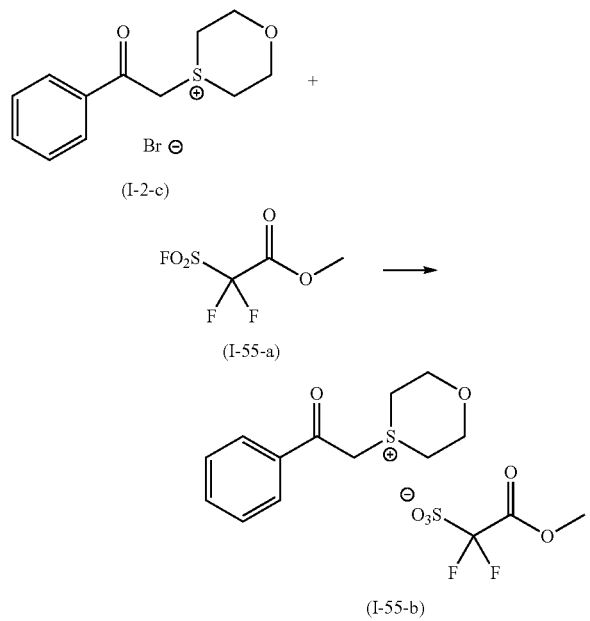

To a reactor, 4.94 part of the salt represented by formula (I-2-c), 57.1 parts of chloroform, 19.9 parts of ion-exchanged water and 3.02 parts of triethylamine were added, and stirred at 23° C. for 30 minutes, followed by cooling to 25° C.

Into the obtained mixture, dropped was a mixture of 2.61 parts of chloroform and 2.61 parts of the compound represented by formula (I-55-a) over 30 minutes at 5° C. and then stirred at 23° C. for one hour. An organic layer was separated from the obtained reaction mixture and 33 parts of 5% aqueous oxalic acid solution were added to the separated layer and stirred at 23° C. for 30 minutes, followed by separating an organic layer therefrom: The washing step was conducted three times.

The washed layer was concentrated to obtain 3.52 parts of the salt represented by formula (I-55-b).

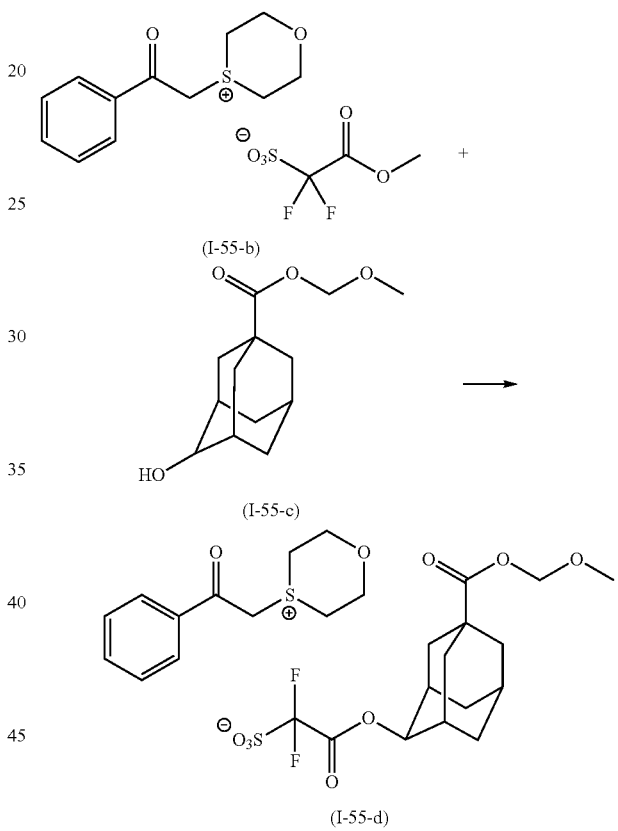

To a reactor, 3.03 parts of the salt represented by formula (I-55-b) was dissolved in 30 parts of chloroform, 2.66 parts of the compound represented by formula (I-55-c), the purity of which was 97.1%, was added thereto, and then 0.05 parts of lithium amide was added and stirred at 23° C. for 30 minutes.

Then to the obtained mixture, 5 parts of molecular sieve [5A: product of WAKO pure chemical, CO., Ltd.] was added and stirred upon heating at 60° C. for 8 hours, followed by cooling to 23° C. Then it is filtrated to collect its filtrate. To the filtrate, 25 parts of ion exchanged water was added and stirred, followed by separating an organic layer therefrom: The washing step was conducted twice.

To the obtained organic layer, 0.5 part of active carbon was added and stirred, followed by being filtrated. The filtrate was concentrated. To the concentrate, 20 parts of acetonitrile was added to dissolve it, followed by being concentrated.

Then 30 parts of tert-methylbutylether were added thereto and stirred, followed by removing its supernatant therefrom. The residue was concentrated. To the obtained concentrate, 20 parts of ethyl acetate was added and stirred, followed by removing its supernatant therefrom, followed by concentrating to obtain 3.63 parts of salt represented by formula (I-55-d).

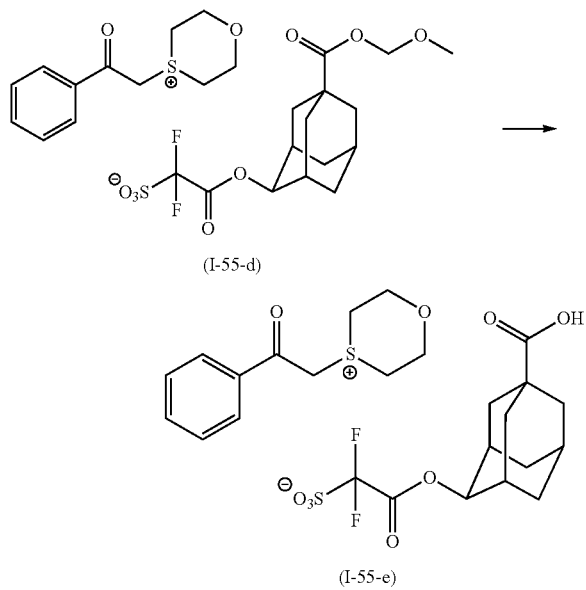

(I-55-d)

To a reactor, added was a mixture of 3.1 parts of the salt represented by formula (I-55-d), 20 parts of chloroform, 3.85 parts of 1N aqueous hydrogen chloride solution and 3.85 parts of methanol, and stirred at 23° C. for 15 hours. Then 20 parts of 1N aqueous sodium hydrogen carbonate solution was added thereto and stirred, followed by separating an organic layer therefrom. To the organic layer, 20 parts of ion exchanged water was added and stirred, followed by separating an organic layer therefrom: The washing step was conducted three times.

To the obtained organic layer, 0.5 part of active carbon was added and stirred, followed by being filtrated. The filtrate was concentrated to obtain 2.44 parts of salt represented by formula (I-55-e).

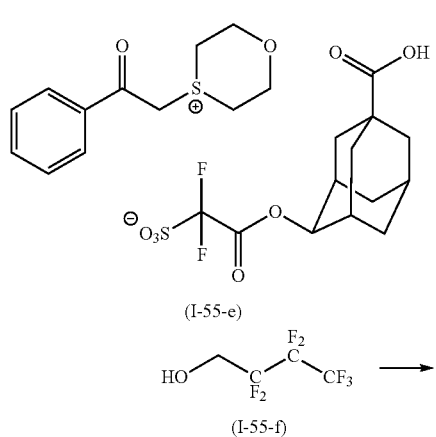

(I-55-e)

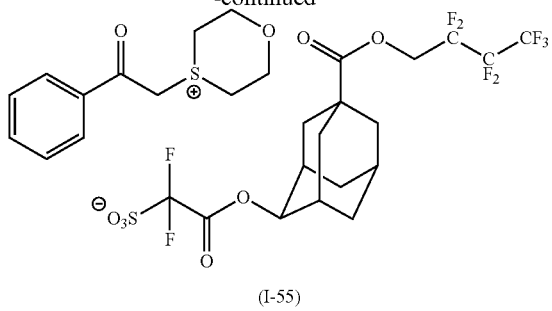

(I-55)

To a reactor, 1.45 parts of the salt represented by formula (I-55-e), 10 parts of acetonitrile and 0.45 parts of carbonyldiimidazole were added, and stirred at 50° C. for 2 hours, followed by cooling to 40° C. Thereinto dropped was a solution which contained 0.5 parts of the compound represented by formula (I-55-f) dissolved in 5 parts of acetonitrile, and the reaction was carried out at 40° C. for 3 hours, followed by cooling to 23° C. To the reaction mixture, 20 parts of chloroform and 20 parts of ion exchanged water were added and stirred, followed by separating an organic layer therefrom. Washing the organic layer with 20 parts of ion exchanged water was repeated until the removed aqueous layer became neutral.

To the obtained organic layer, 0.5 part of active carbon was added and stirred, followed by being filtrated. Then the filtrate was concentrated. To the concentrate, 10 parts of ethyl acetate was added thereto and stirred, followed by removing its supernatant therefrom.

To the obtained residue, 10 parts tert-butylmethylether was added and stirred, followed by removing its supernatant therefrom.

The obtained residue was dissolved in chloroform and concentrated to obtain 0.99 parts of the salt represented by formula (I-55).

MASS (ESI (+) Spectrum): M$^+$ 223.1

MASS (ESI (−) Spectrum): M$^-$ 535.1

Synthesis Example 1

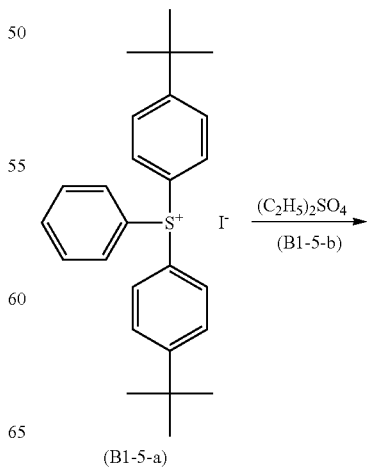

(B1-5-a)

-continued

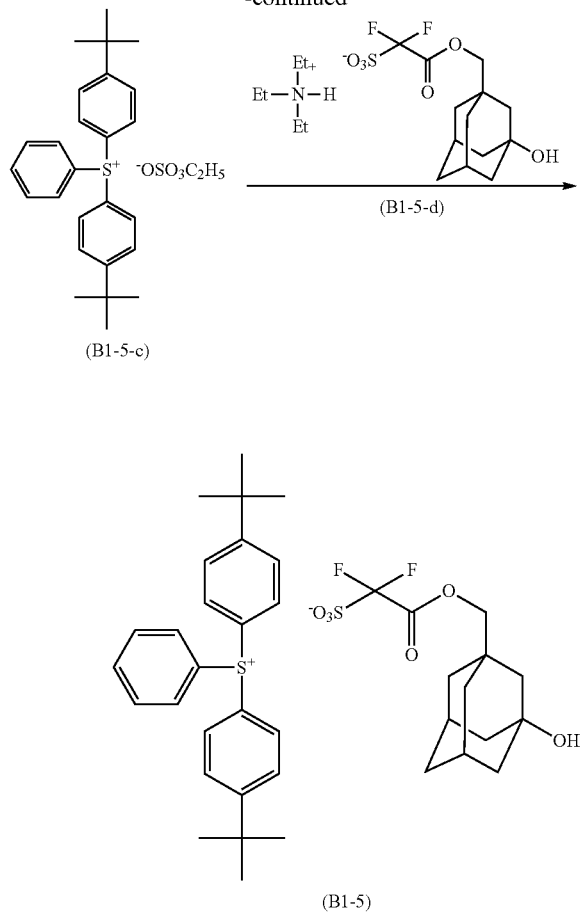

To a reactor, 50.49 parts of the salt represented by formula (B1-5-a) and 252.44 parts of chloroform were added and they were stirred at 23° C. for 30 minutes. Then 16.27 parts of the salt represented by formula (B1-5-b) were dropped thereto and then stirred at 23° C. for an hour to obtain a solution containing the salt represented by formula (B1-5-c).

To the obtained solution, 48.8 parts of the salt represented by formula (B1-5-d) and 84.15 parts of ion-exchanged water were added then stirred at 23° C. for 12 hours to obtain a reaction solution with two separated phases. Then chloroform layer was separated therefrom, and 84.15 parts of ion-exchanged water were added thereto for washing: This washing step was conducted 5 times.

To the washed chloroform layer, 3.88 parts of active carbon were added and then they were stirred, followed by conducting filtration.

The collected filtrate was concentrated. To the obtained residue, 125.87 parts of acetonitrile was added and stirred, followed by being concentrated.

To the obtained residue, 20.62 parts of acetonitrile and 309.30 parts of tert-butylmethylether were added and stirred at 23° C. for 30 minutes, followed by removing its supernatant therefrom. Then To the residue, 200 parts of n-heptane were added and stirred at 23° C. for 30 minutes, followed by being filtrated to obtain 61.54 parts of the salt represented by formula (B1-5).

MASS (ESI(+) Spectrum): $M^+$ 375.2

MASS (ESI(−) Spectrum): $M^-$ 339.1

Synthesis Example 2

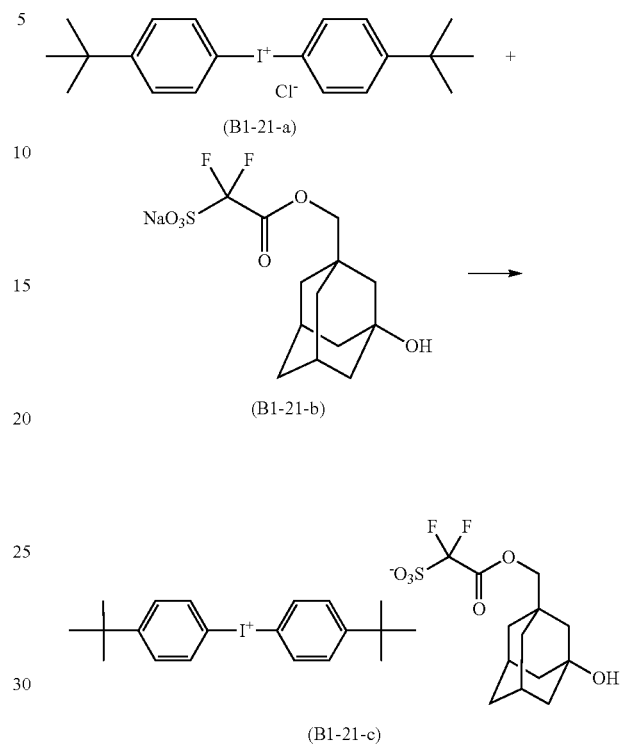

In a reactor, 30.00 parts of the salt represented by formula (B1-21-b) which had been produced according to the method described in JP 2008-209917A1, 35.50 parts of the salt represented by formula (B1-21-a), 100 parts of chloroform and 50 parts of ion-exchanged water were fed and stirred at 23° C. for 15 hours. From the obtained reaction mixture which had two phases, a chloroform layer was collected with separation.

The chloroform layer was washed with 30 parts of ion-exchanged water for washing: This washing was conducted five times.

The washed chloroform layer was concentrated. To the obtained residue, 100 parts of tert-butylmethylether was added and then stirred at 23° C. for 30 minutes, followed by being filtrated to obtain 48.57 parts of the salt represented by formula (B1-21-c).

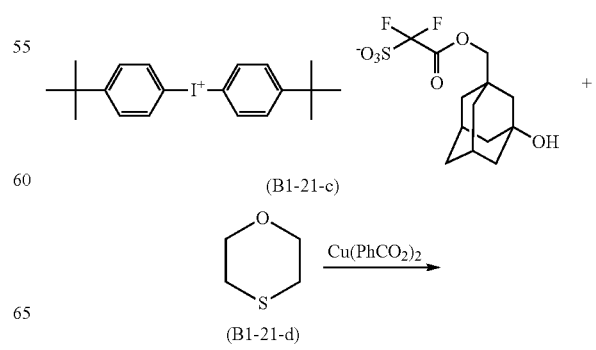

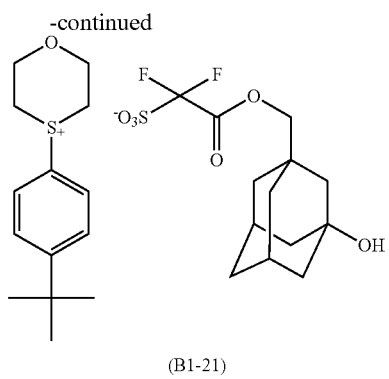

(B1-21)

Into a reactor, 20.00 parts of the salt represented by formula (B1-21-c), 2.84 parts of the compound represented by formula (B1-21-d) and 250 parts of monochlorobenzene were fed and then they were stirred at 23° C. for 30 minutes.

To the resultant mixture, 0.21 part of copper (II) dibenzoate was added. The resultant mixture was stirred at 100° C. for 1 hour.

The mixture was concentrated, and then 200 parts of chloroform and 50 parts of ion-exchanged water were added to the obtained residue, followed by being stirred at 23° C. for 30 minutes. Then the organic layer was collected by separation. The organic layer was washed with 50 parts of ion-exchanged water and then they were stirred at 23° C. for 30 minutes, followed by collecting an organic layer by separation: This washing was conducted five times.

The washed organic layer was concentrated. To the residue, 53.51 parts of acetonitrile was added, and the resultant mixture was concentrated. To the residue, 113.05 parts of tert-butylmethylether was added and then they were stirred, followed by being filtrated to obtain 10.47 parts of the salt represented by formula (B1-21).

MASS (ESI(+) Spectrum): M⁺ 237.1
MASS (ESI(−) Spectrum): M⁻ 339.1

Synthesis Example 3

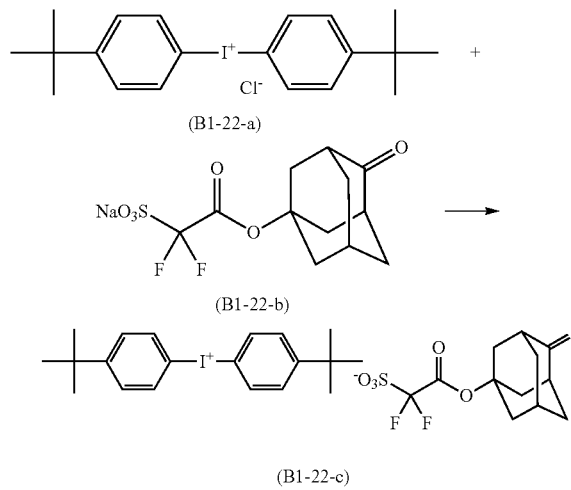

Into a reactor, 11.26 parts of the salt represented by formula (B1-22-a), 10.00 parts of the compound represented by formula (B1-22-b), 50 parts of chloroform and 25 parts of ion-exchanged water were fed and then they were stirred at 23° C. for 15 hours.

From the obtained reaction mixture which had two phases, a chloroform layer was collected with separation.

The chloroform layer was washed with 15 parts of ion-exchanged water for washing: This washing was conducted five times.

The washed chloroform layer was concentrated. To the obtained residue, 50 parts of tert-butylmethylether was added and then stirred at 23° C. for 30 minutes, followed by being filtrated to obtain 11.75 parts of the salt represented by formula (B1-22-c).

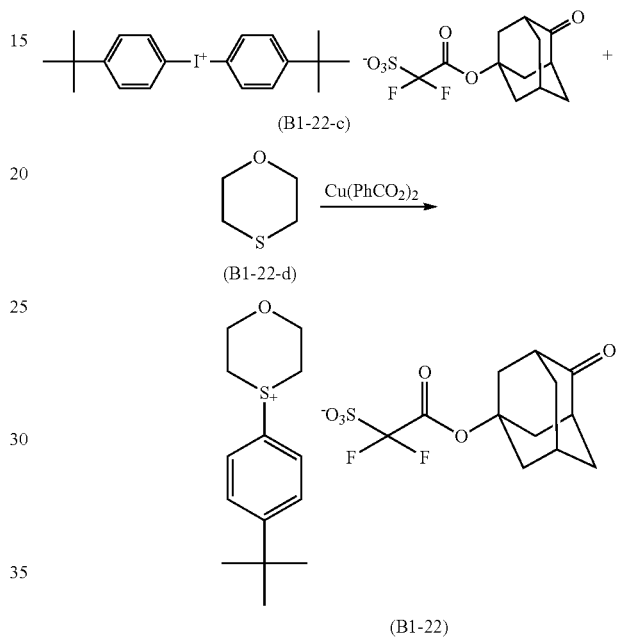

Into a reactor, 11.71 parts of the salt represented by formula (B1-22-c), 1.70 parts of the compound represented by formula (B1-22-d) and 46.84 parts of monochlorobenzene were fed and then they were stirred at 23° C. for 30 minutes.

To the resultant mixture, 0.12 part of copper (II) dibenzoate were added. The resultant mixture was stirred at 100° C. for 30 minutes.

The mixture was concentrated, and then 50 parts of chloroform and 12.50 parts of ion-exchanged water were added to the obtained residue, followed by being stirred at 23° C. for 30 minutes. Then the organic layer was collected by separation. The organic layer was washed with 12.50 parts of ion-exchanged water and then they were stirred at 23° C. for 30 minutes, followed by collecting an organic layer by separation: This washing was conducted eight times.

The washed organic layer was concentrated. To the residue, 50 parts of tert-butylmethylether was added, followed by being filtrated to obtain 6.84 parts of the salt represented by formula (B1-22).

MASS (ESI(+) Spectrum): M⁺ 237.1
MASS (ESI(−) Spectrum): M⁻ 323.0

Compounds used as monomers in the following Synthesis Examples are shown as follow.

(a1-1-3)
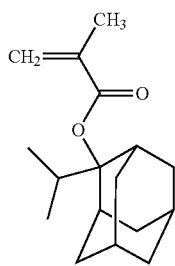

(a1-2-9)
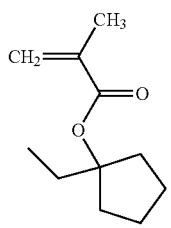

(a2-1-1)
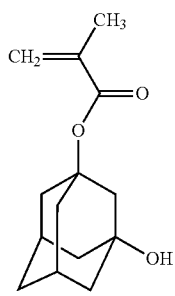

(a3-4-2)
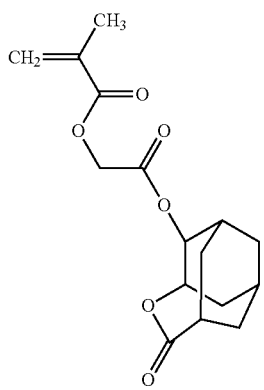

(a4-0-1)
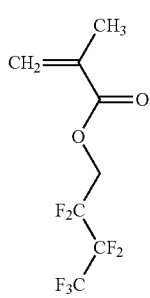

(a4-1-7)
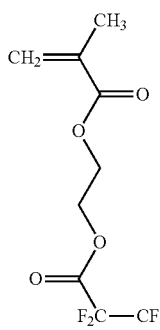

(a5-1-1)
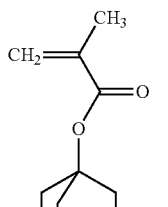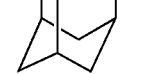

Here, each of the compounds is referred as to "monomer (X)" where "X" is the symbol of the formula representing the monomer.

Synthesis Example 5

There were mixed monomers (a1-1-3), (a1-2-9), (a2-1-1) and (a3-4-2) in a molar ratio of 40/11/4/45 (monomer (a1-1-3)/monomer (a1-2-9)/monomer (a2-1-1)/monomer (a3-4-2)) as well as propyleneglycolmonomethylether acetate in 1.5 times part based on total parts of all monomers to prepare a mixture. To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 75° C. for about 5 hours.

The reaction mixture was poured into a large amount of a mixture of methanol and water to cause precipitation. The precipitate was collected by filtration.

Then the filtrates were dissolved in propyleneglycolmonomethylether acetate and the resultant solution was poured into a large amount of a mixture of methanol and water to cause precipitation, followed by being filtrated: This operation was conducted twice for purification.

As a result, a resin having a weight-average molecular weight of about $8.2 \times 10^3$ was obtained in yield of 68%. This resin is called as Resin A1. Resin A1 had the following structural units.

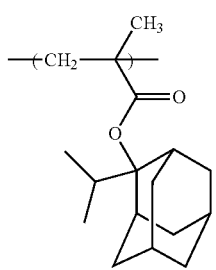 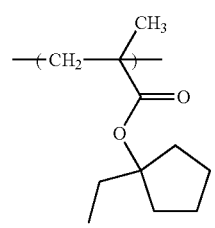

145

-continued

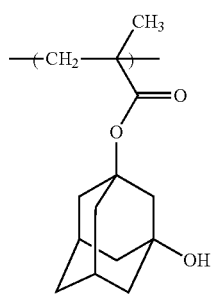
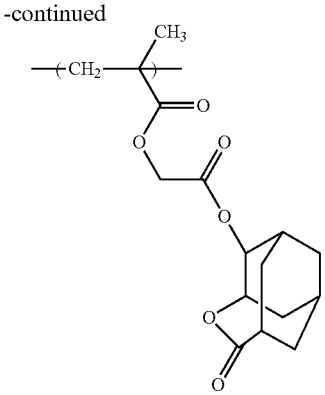

Synthesis Example 6

There were mixed monomer (a4-1-7) and 1,4-dioxane in 1.5 times part based on total parts of all monomers to prepare a mixture. To the mixture, azobisisobutyronitrile as an initiator in the ratio of 0.7 mol % based on all monomer molar amount and azobis(2,4-dimethylvaleronitrile) as an initiator in the ratio of 2.1 mol % based on all monomer molar amount were added, and the obtained mixture was heated at 75° C. for about 5 hours.

The reaction mixture was poured into a large amount of a mixture of methanol and water to cause precipitation. The precipitate was collected by filtration.

Then the reaction mixture was poured into a large amount of a mixture of methanol and water to cause precipitation. The precipitate was collected by filtration: This operation was conducted twice for purification.

As a result, a resin having a weight-average molecular weight of about $1.8 \times 10^4$ was obtained in yield of 77%. This resin is called as resin X1. Resin X1 had the following structural unit.

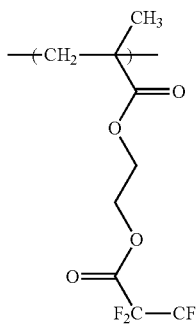

Synthesis Example 7

There were mixed monomers (a5-1-1) and (a4-0-1) in a molar ratio of 75/25 [monomers (a5-1-1)/monomer (a4-0-1)] as well as methylisobutylketone in 1.2 times part based on total parts of all monomers to prepare a mixture.

To the mixture, azobis(2,4-dimethylvaleronitrile) as an initiator in the ratio of 2 mol % based on all monomer molar amount was added, and the obtained mixture was heated at 70° C. for about 5 hours.

The reaction mixture was poured into a large amount of a mixture of methanol and water to cause precipitation.

146

As a result, a resin having a weight-average molecular weight of about $1.7 \times 10^4$ was obtained in yield of 87%. This resin is called as resin X2. Resin X2 had the following structural units.

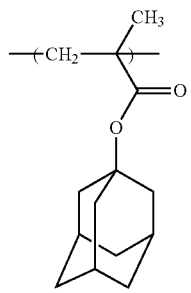
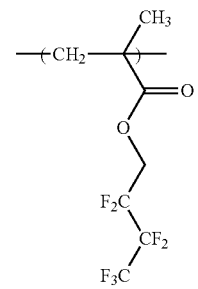

Examples 5 to 14 and Comparative Examples 1 to 3

<Production of Photoresist Compositions>

The following components as listed in Table 4 were mixed and dissolved in the solvent as mentioned below, and then filtrated through a fluororesin filter having pore diameter of 0.2 μm, to prepare photoresist compositions.

TABLE 4

| Comp. No. | Resin (kind/ amount (part)) | Salt of formula (I) (kind/ amount (part)) | Acid generator (kind/ amount (part)) | Quencher (kind/ amount (part)) | PB (° C.)/ PEB (° C.) |
|---|---|---|---|---|---|
| Comp. 1 | A1/10 | I-2/1.50 | None | D1/0.1 | 90/85 |
| Comp. 2 | A1/10 | I-2/0.8 | B1-5/0.15 B1-22/0.40 | D1/0.1 | 90/85 |
| Comp. 3 | A1/10 | I-2/0.8 | B1-21/0.35 B1-22/0.30 | D1/0.1 | 90/85 |
| Comp. 4 | A1/10 X1/0.7 | I-2/0.4 | B1-21/0.55 B1-22/0.40 | D1/0.1 | 90/85 |
| Comp. 5 | A1/10 X1/0.7 | I-2/1.5 | None | D1/0.1 | 90/85 |
| Comp. 6 | A1/10 X2/0.7 | I-2/1.5 | None | D1/0.1 | 90/85 |
| Comp. 7 | A1/10 X1/0.3 | I-2/0.8 | B1-21/0.35 B1-22/0.30 | D1/0.1 | 90/85 |
| Comp. 8 | A1/10 X1/0.3 | I-71/0.8 | B1-21/0.35 B1-22/0.30 | D1/0.1 | 90/85 |
| Comp. 9 | A1/10 X1/0.3 | I-63/0.8 | B1-21/0.35 B1-22/0.30 | D1/0.1 | 90/85 |
| Comp. 10 | A1/10 X1/0.3 | I-55/0.8 | B1-21/0.35 B1-22/0.30 | D1/0.1 | 90/85 |
| Comp. 11 | A1/10 | I-63/1.50 | None | D1/0.1 | 90/85 |
| Comp. 12 | A1/10 | I-55/1.50 | None | D1/0.1 | 90/85 |
| Compar. Comp. 1 | A1/10 | None | B1-x1/1.5 | D1/0.1 | 90/85 |
| Compar. Comp. 2 | A1/10 | None | B1-x2/1.5 | D1/0.1 | 90/85 |
| Compar. Comp. 3 | A1/10 | None | B1-x3/1.5 | D1/0.1 | 90/85 |

In Table 4, each of symbols represents the following component:
<Resin>
A1: Resin A1, X1: Resin X1, X2: Resin X2,
<Salt of Formula (I)>
I-2: The compound represented by formula (I-2)
I-71: The compound represented by formula (I-71)
I-63: The compound represented by formula (I-63)
I-55: The compound represented by formula (I-55)

147

<Acid Generator>
B1-5: Salt represented by formula (B1-5)
B1-21: Salt represented by formula (B1-21)
B1-22: Salt represented by formula (B1-22)
B1-X1: Salt represented by formula (B1-X1)
B1-X2: Salt represented by formula (B1-X2)
B1-X3: Salt represented by formula (B1-X3)

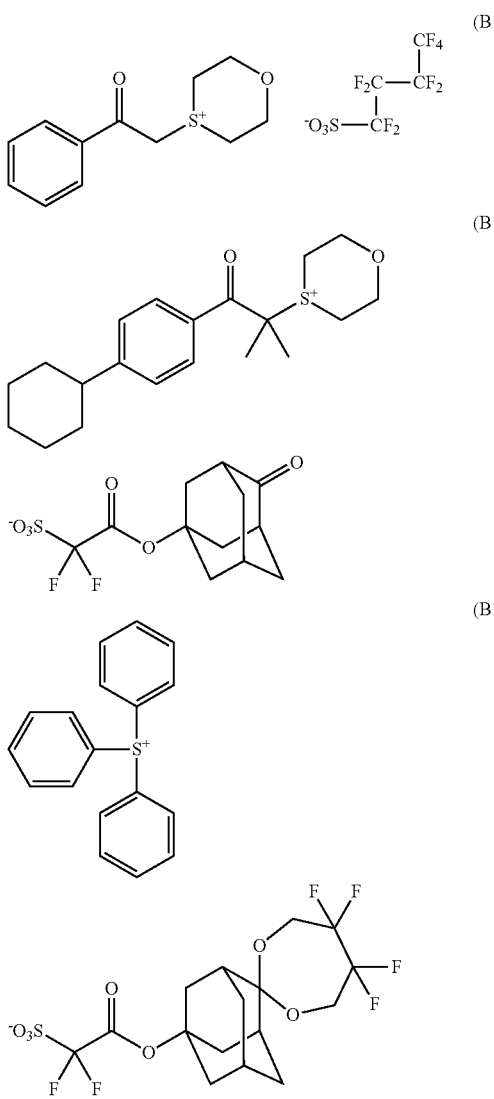

<Quencher>
D1: The compound of the following formula:

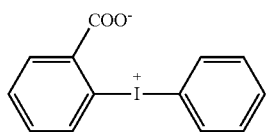

<Solvent>
Mixture of the Following Solvents

| propyleneglycolmonomethylether acetate | 265 parts |
| propyleneglycolmonomethylether | 20 parts |

148

| -continued | |
|---|---|
| 2-heptanone | 20 parts |
| γ-butyrolactone | 3.5 parts |

<Evaluation>

I. Focal Margin [DOF]

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 100 nm after drying. The silicon wafers thus coated with the respective photoresist compositions were each prebaked on a direct hotplate at a temperature shown in the column "PB" in Table 4 for 60 seconds. Using an ArF excimer stepper for immersion exposure ("XT: 1900Gi" manufactured by ASML, NA=1.35, Annular $\sigma_{out}$=0.85, $\sigma_{in}$=0.65, X-Y polarization), each wafer thus formed with the respective resist film was subjected to exposure with the exposure quantity being varied stepwise. For the exposure, a photomask for forming a trench pattern, which has 120 nm of its pitch and 40 nm of width in trench pattern, was used. Ultrapure water was used as an immersion medium.

After the exposure, each wafer was subjected to post-exposure baking on a hotplate at a temperature shown in the column "PEB" in Table 4 for 60 seconds and then to development in the manner of dynamic dispense method at 23° C. for 20 seconds with butyl acetate (manufactured by Tokyo Chemical Industries, Co., Ltd) to make a negative type photoresist pattern.

In this evaluation, effective sensitivity [ES] was expressed as the exposure quantity that the width in trench pattern became 40 nm after development.

The photoresist patterns were obtained in the manner as mentioned above, at the exposure quantity of ES, with the focal point distance being varied stepwise.

The focal point distances at the exposure were measured when the width in trench pattern was within 40 nm±5%, i.e., between 38 nm and 42 nm.

The difference between the max value and the minimum value as to the focal point distances was calculated. Each of the differences is also shown in parentheses in a column of "DOF".

II. CD Uniformity [CDU]

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 85 nm after drying.

The silicon wafers thus coated with the respective photoresist compositions were each prebaked on a direct hotplate at a temperature shown in the column "PB" in Table 4 for 60 seconds. Using an ArF excimer stepper for immersion exposure ("XT: 1900Gi" manufactured by ASML, NA=1.35, ¾ Annular, X-Y polarization), each wafer thus formed with the respective resist film was subjected to exposure with the exposure quantity being varied stepwise. For the exposure, a photomask for forming a contact hole pattern, which has 90 nm of its hole pitch and 55 nm of hole diameter, was used. Ultrapure water was used as an immersion medium.

After the exposure, each wafer was subjected to post-exposure baking on a hotplate at a temperature shown in the column "PEB" in Table 4 for 60 seconds and then to development in the manner of dynamic dispense method at 23° C. for 20 seconds with butyl acetate (manufactured by Tokyo Chemical Industries, Co., Ltd) to make a photoresist pattern.

In this evaluation, effective sensitivity [ES] was expressed as the exposure quantity that the hole diameter became 50 nm after development.

The photoresist patterns obtained with the exposure at ES using the above-mentioned photomask were observed with a scanning electron microscope.

The hole diameter of the contact hole pattern was determined by measuring a distance between across two points on its circle, which distance corresponds to its diameter, at 24 sites of the circle. The average of the measured values was regarded as the average hole diameter.

The standard deviation [CDU] was calculated under the condition that the average diameter of four hundred holes about the patterns obtained with the exposure at ES using a photomask with a hole diameter of 50 nm was regarded to as population.

When the standard deviation was 2 nm or less, DOF was evaluated as good. When the difference was larger than 2 nm, DOF was evaluated as bad. In Table 5, good DOF is represented by "○", bad DOF is represented by "x", and each of the standard deviation is shown in parentheses recited in a column of "CDU".

The results of evaluation were marked as follow, and listed in Table 5.

TABLE 5

| Ex. No. | Composition | DOF (nm) | CDU |
|---|---|---|---|
| Ex. 5 | Comp. 1 | 105 | ○ (1.86 nm) |
| Ex. 6 | Comp. 2 | 90 | ○ (1.90 nm) |
| Ex. 7 | Comp. 3 | 105 | ○ (1.83 nm) |
| Ex. 8 | Comp. 4 | 90 | ○ (1.88 nm) |
| Ex. 9 | Comp. 5 | 105 | ○ (1.87 nm) |
| Ex. 10 | Comp. 6 | 105 | ○ (1.85 nm) |
| Ex. 11 | Comp. 7 | 105 | ○ (1.82 nm) |
| Ex. 12 | Comp. 8 | 105 | ○ (1.84 nm) |
| Ex. 13 | Comp. 9 | 90 | ○ (1.92 nm) |
| Ex. 14 | Comp. 10 | 90 | ○ (1.94 nm) |
| Comp. Ex. 1 | Compar. Comp. 1 | 15 | X (3.12 nm) |
| Comp. Ex. 2 | Compar. Comp. 2 | 60 | X (2.06 nm) |
| Comp. Ex. 3 | Compar. Comp. 3 | 45 | X (2.68 nm) |

III. Evaluations as to Positive Photoresist Patterns

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 4 for 60 seconds. Using an ArF excimer stepper for immersion exposure ("XT: 1900Gi" manufactured by ASML, NA=1.35, ¾ Annular, X-Y polarization), each wafer thus formed with the respective resist film was subjected to exposure with the exposure quantity being varied stepwise. For the exposure, a photomask for forming a contact hole pattern, which has 100 nm of its pitch and 70 nm of hole diameter was used. Ultrapure water was used as an immersion medium.

After the exposure, each wafer was subjected to post-exposure baking on a hotplate at a temperature shown in the column "PEB" in Table 4 for 60 seconds and then to paddle development at 23° C. for 20 seconds with 2.38% aqueous tetramethylammonium hydroxide solution (manufactured by Tokyo Chemical Industries, Co., Ltd) to make a photoresist pattern.

In this evaluation in which the pattern was formed using a mask with 70 nm in hole diameter, the effective sensitivity [ES] was expressed as the exposure quantity that the hole diameter became 55 nm after development.

The photoresist patterns were obtained in the manner as mentioned above, at the exposure quantity of ES, with the focal point distance being varied stepwise.

The focal point distances at the exposure were measured when the hole diameter was within 55 nm±5%, i.e., between 52.5 nm and 57.5 nm.

The difference between the max value and the minimum value as to the focal point distances was calculated. Each of the differences is also shown in parentheses in a column of "DOF".

When the difference was 200 nm or more, DOF was evaluated as good.

When the difference was less than 200 nm, DOF was evaluated as bad. In Table 6, good DOF is represented by "○", bad DOF is represented by "x", and each of the differences is shown in parentheses recited in a column of "DOF".

The hole diameter of the contact hole pattern was determined by measuring a distance between across two points on its circle, which distance corresponds to its diameter, at 24 sites of the circle. The average of the measured values was regarded as the average hole diameter.

The standard deviation [CDU] was calculated under the condition that the average diameter of four hundred holes about the patterns obtained with the exposure at ES using the above-mentioned photomask was regarded to as population.

When the standard deviation was 2 nm or less, CDU was evaluated as good. When the difference was larger than 2 nm, CDU was evaluated as bad. In Table 6, good CDU is represented by "○", bad CDU is represented by "x", and each of the standard deviation is shown in parentheses recited in a column of "CDU".

The results of evaluation were marked as follow, and listed in Table 6.

TABLE 6

| Ex. No. | Composition | DOF | CDU |
|---|---|---|---|
| Ex. 15 | Comp. 7 | ○ (210 nm) | ○ (1.75 nm) |
| Ex. 16 | Comp. 8 | ○ (210 nm) | ○ (1.78 nm) |
| Ex. 17 | Comp. 9 | ○ (240 nm) | ○ (1.68 nm) |
| Ex. 18 | Comp. 10 | ○ (240 nm) | ○ (1.67 nm) |
| Ex. 19 | Comp. 11 | ○ (240 nm) | ○ (1.67 nm) |
| Ex. 20 | Comp. 12 | ○ (240 nm) | ○ (1.69 nm) |
| Comp. Ex. 4 | Compar. Comp. 1 | X (90 nm) | (2.48 nm) |
| Comp. Ex. 5 | Compar. Comp. 2 | X (180 nm) | X (2.06 nm) |
| Comp. Ex. 6 | Compar. Comp. 3 | X (180 nm) | X (2.11 nm) |

The photoresist composition of the disclosure can show an excellent CD uniformity or DOF when a photoresist pattern is made from it.

What is claimed is:

1. A photoresist composition comprising:
an acid generator which comprises, a salt represented by formula (I):

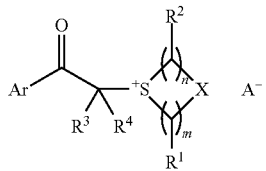
(I)

in which X represents an oxygen atom, a sulfur atom or —N(SO2R⁵)—;

R⁵ represents a C1-C12 alkyl group which can have a fluorine atom and in which a methylene group can be replaced by an oxygen atom or a carbonyl group, a C3-C12 cycloalkyl group which can have a fluorine atom, or a C6-C12 aromatic hydrocarbon group which can have a fluorine atom;

Ar represents a C6-C36 aromatic hydrocarbon group which can have a substituent or a C4-C36 heteroaromatic hydrocarbon group which can have a substituent;

R¹ and R² each independently represent a hydrogen atom, a hydroxy group, or a C1-C12 hydrocarbon group in which a methylene group can be replaced by an oxygen atom or a carbonyl group;

"m" and "n" each independently represent 1 or 2;

R³ and R⁴ each independently represent a hydrogen atom; and

A⁻ represents an organic anion represented by formula (a-2), formula (I—Ba) or formula (I-Bb):

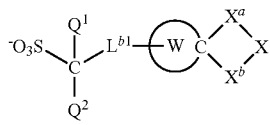
(a-2)

in which $X^a$ and $X^b$ each independently represent an oxygen atom or a sulfur atom;

$X^1$ represents a divalent C1-C12 saturated hydrocarbon group which has a fluorine atom;

the ring W represents a ring represented by formula (a-1-1), formula (a-1-2) or formula (a-1-3):

(a-1-1)

(a-1-2)

(a-1-3)

in which ring a methylene group can be replaced by an oxygen atom, a sulfur atom, a carbonyl group or a sulfonyl group and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of them:

$L^{b1}$ represents a group represented by *—CO—O—(CH$_2$)$_t$— where t represents an integer of 0 to 6 and * represents a binding site to —C(Q¹)(Q²)-; and Q¹ and Q² each independently represent a fluorine atom or a C1-C6 perfluroalkyl group,

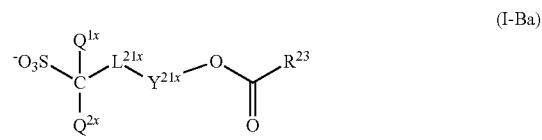
(I-Ba)

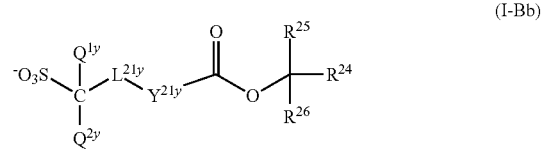
(I-Bb)

in which $Q^{1x}, Q^{2x}, Q^{1y}$ and $Q^{2y}$ each independently represent a fluorine atom or a C1-C6 perfluroalkyl group;

$L^{21x}$ and $L^{21y}$ each independently represent a single bond or a C1-C17 alkanediyl group in which a methylene group can be replaced by an oxygen atom or a carbonyl group;

$R^{23}$ represents a C1-C6 fluoroalkyl group;

$Y^{21x}$ and $Y^{21y}$ each independently represent a C3-C18 divalent alicyclic hydrocarbon group in which a methylene group can be replaced by an oxygen atom or a carbonyl group;

$R^{24}$ represents a C1-C05 fluoroalkyl group, and $R^{25}$ and $R^{26}$ each independently represent a hydrogen atom or a fluorine atom; and a salt consisting of a cation represented by formula (b2-1) and an anion represented by (B1):

(b2-1)

in which $R^{b4}$, $R^{b5}$ and $R^{b6}$ independently represent a C1-C30 aliphatic hydrocarbon group which can have a substituent selected from the group consisting of a hydroxy group, a C1-C12 alkoxy group, a C3-C12 alicyclic hydrocarbon group and a C6-C18 aromatic hydrocarbon group, a C3-C36 alicyclic hydrocarbon group which can have a substituent selected from the group consisting of a C1-C18 aliphatic hydrocarbon group, a C2-C4 acyl group and a glycidyloxy group, or a C6-C36 aromatic hydrocarbon group which can have a substituent selected from the group consisting of a hydroxy group, a C1-C18 aliphatic hydrocarbon group and a C1-C12 alkoxy group, and in in which $R^{b4}$ and $R^{b5}$ can be bonded to form a ring together with the adjacent S+, and a methylene group in the ring may be replaced by —CO—, —O— or —SO—;

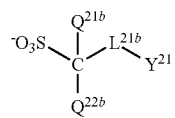

(B1)

wherein $Q^{21b}$ and $Q^{22b}$ independently each represent a fluorine atom or a C1-C6 perfluoroalkyl group;

$L^{21b}$ represents a C1-C24 divalent hydrocarbon group where a methylene group can be replaced by an oxygen atom or a carbonyl group and where a hydrogen atom can be replaced by a fluorine atom or a hydroxy group; and $Y^{21}$ represents a C3-C18 alicyclic hydrocarbon group where a methylene group can be replaced by an oxygen atom, a carbonyl group or a sulfonyl group and where a hydrogen atom can be replaced by a fluorine atom or a hydroxy group; and a resin having an acid-labile group which comprises a structural unit represented by formulae (a3-4);

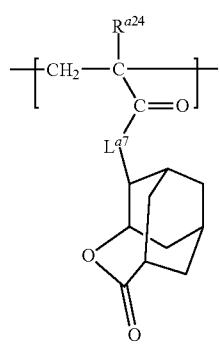

(a3-4)

in which $R^{a24}$ represents a hydrogen atom, a halogen atom other than a fluorine atom, or a C1-C6 alkyl group which can have a halogen atom other than a fluorine atom, $L^{a7}$ represents —O—, $^{*1}$—O-$L^{a8}$-O—, $^{*1}$—O-$L^{a8}$-CO—O-$L^{a9}$-CO—O— or $^{*1}$—O-$L^{a8}$-CO—O-$L^{a9}$-O— in which $L^{a8}$ and $La^{a9}$ each independently represents a C1-C6 divalent alkanediyl group, and $^{*1}$ represents a binding site to —CO—.

2. The photoresist composition according to claim 1, further comprising a salt which generates an acid having an acidity weaker than an acid generated from said acid generator.

3. A process for producing a photoresist pattern comprising the following steps (1) to (5):

(1) a step of applying the photoresist composition according to claim 1 on a substrate, 2) a step of forming a composition film by conducting drying, (3) a step of exposing the composition film to radiation, (4) a step of baking the exposed composition film, and (5) a step of developing the baked composition film.

4. The photoresist composition according to claim 1, further comprising another resin which comprises a structural unit having a halogen atom.

* * * * *